US007575785B2

(12) United States Patent
Lietzau et al.

(10) Patent No.: US 7,575,785 B2
(45) Date of Patent: Aug. 18, 2009

(54) CYCLOPENTA[A]NAPHTHALINE DERIVATIVES

(75) Inventors: Lars Lietzau, Darmstadt (DE); Matthias Bremer, Darmstadt (DE); Melanie Klasen-Memmer, Heuchelheim (DE)

(73) Assignee: Merck Patent GmbH, Darmstadt (DE)

( * ) Notice: Subject to any disclaimer, the term of this patent is extended or adjusted under 35 U.S.C. 154(b) by 170 days.

(21) Appl. No.: 10/568,783

(22) PCT Filed: Aug. 2, 2004

(86) PCT No.: PCT/EP2004/008632

§ 371 (c)(1), (2), (4) Date: Feb. 21, 2006

(87) PCT Pub. No.: WO2005/021682

PCT Pub. Date: Mar. 10, 2005

(65) Prior Publication Data

US 2006/0202163 A1 Sep. 14, 2006

(30) Foreign Application Priority Data

Aug. 22, 2003 (DE) ................................ 103 38 711

(51) Int. Cl.

*C09K 19/32* (2006.01)
*C09K 19/30* (2006.01)
*C07C 23/28* (2006.01)
*C07C 25/22* (2006.01)
*C07C 49/697* (2006.01)

(52) U.S. Cl. .............. 428/1.1; 252/299.62; 252/299.63; 568/633; 568/634; 570/183; 570/187

(58) Field of Classification Search ............ 252/299.62, 252/299.63, 299.61; 428/1.1; 570/185, 183, 570/187; 568/633, 634

See application file for complete search history.

(56) References Cited

U.S. PATENT DOCUMENTS

| | | | | |
|---|---|---|---|---|
| 6,548,710 | B2 * | 4/2003 | Woudenberg | 568/323 |
| 6,737,125 | B2 * | 5/2004 | Hornung et al. | 428/1.1 |
| 6,759,103 | B2 * | 7/2004 | Hornung et al. | 428/1.1 |
| 7,291,366 | B2 * | 11/2007 | Lietzau et al. | 428/1.1 |
| 2003/0091756 | A1 | 5/2003 | Hornung et al. | |
| 2003/0108684 | A1 | 6/2003 | Hornung et al. | |

FOREIGN PATENT DOCUMENTS

| | | |
|---|---|---|
| DE | 4434974 | 4/1996 |
| DE | 4434975 | 4/1996 |
| WO | WO 2004020375 | 3/2004 |

OTHER PUBLICATIONS

Caplus 1955: 8181.*

Butera et al., "Computer-Assisted Design and Synthesis of Novel Aldose Redutase Inhibitors", J. Med. Chme., 1989, 32, 757-765.*

Caplus 1989: 172853.*

* cited by examiner

*Primary Examiner*—Shean C Wu

(74) *Attorney, Agent, or Firm*—Millen, White, Zelano & Branigan, P.C.

(57) ABSTRACT

The present invention relates to cyclopenta[a]naphthalene derivatives of the general formulae I to V

I

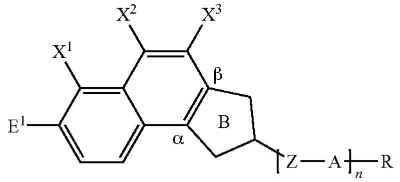

II

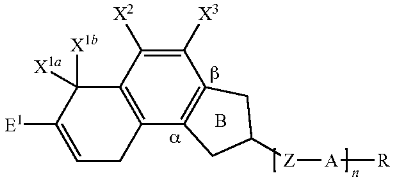

III

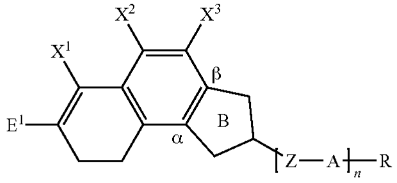

IV

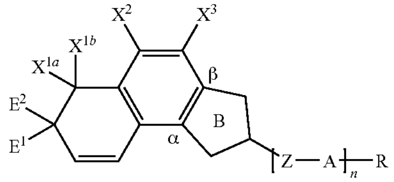

V

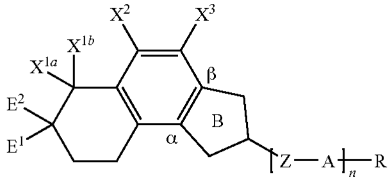

in which B, Z, A, n, R, $X^1$, $X^{1a}$, $X^{1b}$, $X^2$, $X^3$, $E^1$ and $E^2$ are as defined in the claims, to the use thereof in liquid-crystalline media, to liquid-crystalline media comprising at least one of these cyclopenta[a]naphthalene derivatives, and to electro-optical display elements containing these liquid-crystalline media.

19 Claims, No Drawings

CYCLOPENTA[A]NAPHTHALINE DERIVATIVES

The present invention relates to cyclopenta[a]naphthalene derivatives, to liquid-crystalline media comprising these derivatives, and to electro-optical display elements containing these liquid-crystalline media. In particular, the invention relates to cyclopenta[a]naphthalene derivatives of negative dielectric anisotropy.

Liquid crystals have found widespread use since the first commercially usable liquid-crystalline compounds were found about 30 years ago. Known areas of application are, in particular, displays for watches and pocket calculators, and large display panels as used in railway stations, airports and sports arenas. Further areas of application are displays of portable computers and navigation systems and video applications. For the last-mentioned applications in particular, high demands are made of the response times and contrast of the images.

The spatial arrangement of the molecules in a liquid crystal has the effect that many of its properties are direction-dependent. Of particular importance for use in liquid-crystal displays are the optical, dielectric and elastomechanical anisotropies. Depending on whether the molecules are oriented with their longitudinal axes perpendicular or parallel to the two plates of a capacitor, the latter has a different capacitance; in other words, the dielectric constant $\epsilon$ of the liquid-crystalline medium has different values for the two orientations. Substances whose dielectric constant is greater when the longitudinal axes of the molecules are oriented perpendicular to the capacitor plates than when they are oriented parallel are referred to as dielectrically positive. In other words, if the dielectric constant $\epsilon_{\parallel}$ parallel to the longitudinal axes of the molecules is greater than the dielectric constant $\epsilon_{\perp}$ perpendicular to the longitudinal axes of the molecules, the dielectric anisotropy $\Delta\epsilon=\epsilon_{\parallel}\epsilon_{\perp}$ is greater than zero. Most liquid crystals used in conventional displays fall into this group.

Both the polarisability of the molecule and the permanent dipole moment play a role for the dielectric anisotropy. On application of a voltage to the display, the longitudinal axis of the molecules orients itself in such a way that the larger of the dielectric constants becomes effective. The strength of the interaction with the electric field depends on the difference between the two constants. In the case of small differences, higher switching voltages are necessary than in the case of large differences. The introduction of suitable polar groups, such as, for example, nitrile groups or fluorine, into the liquid-crystal molecules enables a broad range of working voltages to be achieved.

In the case of the liquid-crystalline molecules used in conventional liquid-crystal displays, the dipole moment oriented along the longitudinal axis of the molecules is larger than the dipole moment oriented perpendicular to the longitudinal axis of the molecules. The orientation of the larger dipole moment along the longitudinal axis of the molecule also determines the orientation of the molecule in a liquid-crystal display in the field-free state. In the most widespread TN ("twisted nematic") cells, a liquid-crystalline layer with a thickness of only from about 5 to 10 μm is arranged between two plane-parallel glass plates, onto each of which an electrically conductive, transparent layer of tin oxide or indium tin oxide (ITO) has been vapour-deposited as electrode. A likewise transparent alignment layer, usually consisting of a plastic (for example polyimides), is located between these films and the liquid-crystalline layer. This alignment layer serves to bring the longitudinal axes of the adjacent liquid-crystalline molecules into a preferential direction through surface forces in such a way that, in the voltage-free state, they lie uniformly on the inside of the display surface with the same alignment in a flat manner or with the same small tilt angle. Two polarisation films which only enable linear-polarised light to enter and escape are adhesively bonded to the outside of the display in a certain arrangement.

By means of liquid crystals in which the larger dipole moment is oriented parallel to the longitudinal axis of the molecule, very high-performance displays have already been developed. In most cases here, mixtures of from 5 to 20 components are used in order to achieve a sufficiently broad temperature range of the mesophase and short response times and low threshold voltages. However, difficulties are still caused by the strong viewing-angle dependence in liquid-crystal displays as are used, for example, for laptops. The best imaging quality can be achieved if the surface of the display is perpendicular to the viewing direction of the observer. If the display is tilted relative to the observation direction, the imaging quality deteriorates drastically under certain circumstances. For greater comfort, attempts are being made to maximise the angle through which the display can be tilted from the viewing direction of an observer without significantly reducing the imaging quality. Attempts have recently been made to improve the viewing-angle dependence using liquid-crystalline compounds whose dipole moment perpendicular to the longitudinal axis of the molecules is larger than that parallel to the longitudinal axis of the molecule. The dielectric anisotropy $\Delta\epsilon$ is negative. In the field-free state, these molecules are oriented perpendicular to the glass surface of the display. By achieving a plurality of domains, it has been possible to achieve an improvement in the viewing-angle dependence using liquid-crystalline media of negative dielectric anisotropy. This technology can also be used to achieve shorter response times in displays and better contrast values. Displays of this type are known as VA-TFT ("vertically aligned") displays.

DE 44 34 975 A1 discloses tricyclic compounds of the general formula

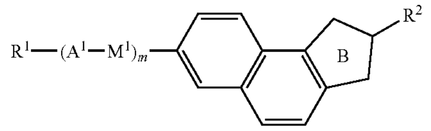

in which the symbols and indices are defined as follows:

$R^1$ is —F, —CN, —Cl, —$CF_3$ or has, independently of $R^2$, one of the meanings mentioned for $R^2$;

$R^2$ is H or a straight-chain or branched alkyl radical having from 1 to 20 carbon atoms (with or without an asymmetrical carbon atom), in which, in addition, one or more —$CH_2$— groups (but not those bonded directly to the five-membered ring) may be replaced by —O—, —S—, —CH═CH—, —C≡C—, cyclo-propane-1,2-diyl, —$Si(CH_3)_2$—, 1,4-phenylene, 1,4-cyclohexylene, 1,3-cyclo-pentylene, 1,3-cyclobutylene or 1,3-dioxane-2,5-diyl, with the proviso that oxygen atoms and sulfur atoms must not be bonded directly, and in which, in addition, one or more H atoms of the alkyl radical may be substituted by F, Cl, Br or $OR^3$ (where $R^3$═H or straight-chain $C_1$-$C_6$-alkyl), or an optically active or racemic group;

Ring B is

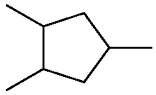 , 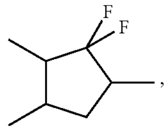 , 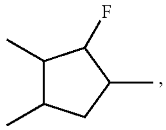 ,

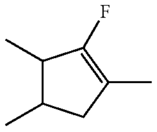 or 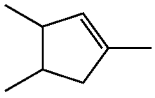 ;

$A^1$ is 1,4-phenylene, 1,4-cyclohexylene, pyridine-2,5-diyl, pyrimidine-2,5-diyl, 1,3,4-thiadiazole-2,5-diyl, 1,3-thiazole-2,5-diyl, 1,3-thiazole-2,4-diyl, in which, in addition, one or more hydrogens may be substituted by F;

$M^1$ is a single bond, $-C{\equiv}C-$, $-CH_2CH_2-$, $-O-CO-$, $-CO-O-$, $-CO-$, $-OCH_2-$, $-CH_2O-$ or $-O-CO-O-$; and m is zero or one.

US Patent Application US 2003/0108684 A1 furthermore discloses tricyclic compounds of the general formula

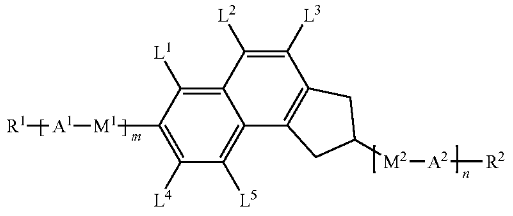

in which the symbols and indices are defined as follows:

$R^1$ is H, F, $CF_3$, $OCF_3$, $OCF_2H$, $OCFH_2$, an alkyl radical or an alkoxy radical or an alkenyl radical or an alkenyloxy radical; $R^2$ is H or an alkyl radical or an alkoxy radical or an alkenyl radical or an alkenyloxy ad; $M^1$ is $-C(=O)O-$, $-OC(=O)-$, $-CH_2O-$, $-OCH_2-$, $-OCF_2-$, $-CF_2O-$, $-C{\equiv}C-$, $-CH_2CH_2-$, $-CF_2CF_2-$, $-CF{=}CFC(=O)O-$ or a single bond; $M^2$ is $-C(=O)O-$, $-OC(=O)-$, $-CH_2O-$, $-OCH_2-$, $-CH_2CH_2-$, $-CF_2CF_2-$ or a single bond; $A^1$ and $A^2$ are phenylene-1,4-diyl or cyclohexane-1,4-diyl, each of which is unsubstituted or mono- or disubstituted by F, or cyclohexene-1,4-diyl or 1,3-dioxane-2,5-diyl, each of which is unsubstituted or monosubstituted by F; m and n are 0 or 1, where m+n=0 or 1; $L^1$, $L^2$, $L^3$, $L^4$ and $L^5$ are, independently of one another, H or F, where at least one of $L^1$, $L^2$, $L^3$, $L^4$ and $L^5$ is F, $L^1$, $L^2$ and $L^3$ are H if $L^5$ is F, and $L^4$ and $L^5$ are H if $L^3$ is F. The five-membered ring fused to the naphthalene structure has (with the exception of two intermediates containing a cyclopentanone ring which are formed in the synthesis of the above-mentioned compounds) no further substituents apart from the $-(-M^2-A^2-)_n-R^2$ radical and also contains no further endocyclic double bonds.

However, the dielectric anisotropy $\Delta\epsilon$ of the compounds disclosed in these two documents is not sufficient to ensure satisfactory properties, in particular sufficiently low characteristic voltages, for example in VA-TFT displays.

Development in the area of liquid-crystalline materials is far from complete. In order to improve the properties of liquid-crystalline display elements, attempts are constantly being made to develop novel compounds which enable such displays to be optimised.

An object of the present invention is therefore to provide compounds having advantageous properties for use in liquid-crystalline media. They should preferably have negative dielectric anisotropy, which makes them particularly suitable for use in liquid-crystalline media for VA displays.

This object is achieved in accordance with the invention by a cyclopenta-[a]naphthalene derivative of one of the general formulae I, II, III, IV and V

I

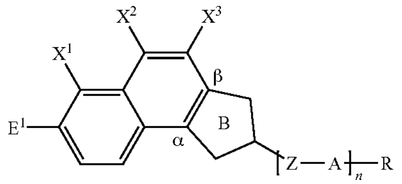

II

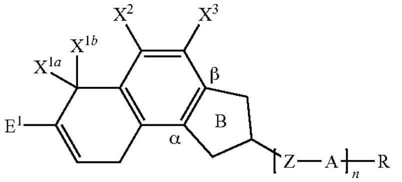

III

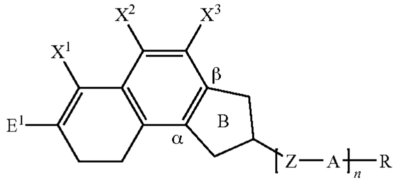

IV

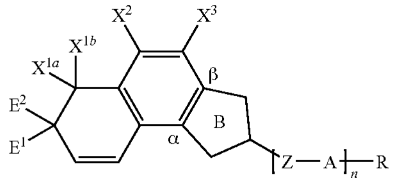

V

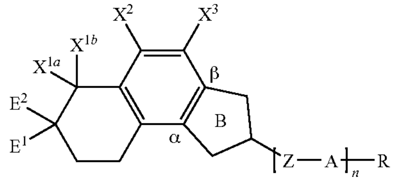

in which:

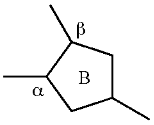

is a

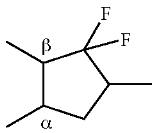 , b

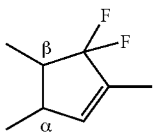 ,

-continued c

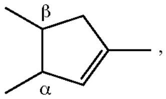

, d

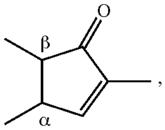

, e

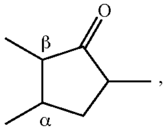

, f

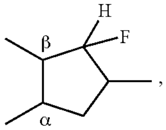

, g

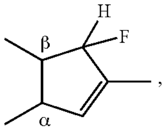

, h

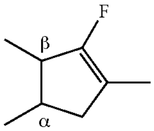

, or i

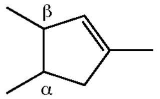

;

A is in each case, independently of one another, 1,4-phenylene, in which =CH— may be replaced once or twice by =N—, and which may be monosubstituted to tetrasubstituted, independently of one another, by halogen (—F, —Cl, —Br —I), —CN, $—CH_3$, $—CH_2F$, $—CHF_2$, $—CF_3$, $—OCH_3$, $—OCH_2F$, $—OCHF_2$ or $—OCF_3$, 1,4-cyclohexylene, 1,4-cyclohexenylene or 1,4-cyclohexadienylene, in which $—CH_2—$ may in each case be replaced once or twice, independently of one another, by —O— or —S— in such a way that heteroatoms are not linked directly, and which all may be monosubstituted or poly-substituted by halogen;

Z is in each case, independently of one another, a single bond, a double bond, $—CF_2O—$, $—OCF_2—$, $—CH_2CH_2—$, $—CF_2CF_2—$, $—CF_2—CH_2—$, $—CH_2—CF_2—$, —CHF—CHF—, —C(O)O—, —OC(O)—, $—CH_2O—$, $—OCH_2—$, —CF═CH—, —CH═CF—, —CF═CF—, —CH═CH— or —C≡C—;

R is hydrogen, an alkyl, alkoxy, alkenyl or alkynyl radical having from 1 to 15 or 2 to 15 carbon atoms respectively which is unsubstituted, monosubstituted by $—CF_3$ or at least monosubstituted by halogen, where, in addition, one or more $CH_2$ groups in these radicals may each, independently of one another, be replaced by —O—, —S—, —CO—, —COO—, —OCO— or —OCO—O— in such a way that heteroatoms are not linked directly, halogen, —CN, —SCN, —NCS, $—SF_5$, $—CF_3$, $—OCF_3$, $—OCHF_2$ or $—OCH_2F$;

$X^1$, $X^{1a}$, $X^{1b}$, $X^2$ and $X^3$ are each, independently of one another, hydrogen, an alkyl, alkoxy, alkenyl or alkynyl radical having from 1 to 15 or 2 to 15 carbon atoms respectively which is unsubstituted or at least monosubstituted by halogen, where, in addition, one or more $CH_2$ groups in these radicals may each, independently of one another, be replaced by —O—, —S—, —CO—, —COO—, —OCO— or —OCO—O— in such a way that heteroatoms are not linked directly, halogen, —CN, $—SF_5$, —SCN, —NCS, $—CF_3$, $—OCF_3$, $—OCHF_2$ or $—OCH_2F$;

$E^1$ and $E^2$ are each, independently of one another, hydrogen, an alkyl, alkoxy, alkenyl or alkynyl radical having from 1 to 15 or 2 to 15 carbon atoms respectively which is unsubstituted or at least mono-substituted by halogen, where, in addition, one or more $CH_2$ groups in these radicals may each, independently of one another, be replaced by —O—, —S—, —CO—, —COO—, —OCO— or —OCO—O— in such a way that heteroatoms are not linked directly, halogen, —CN, —SCN, —NCS, $—SF_5$, $—CF_3$, $—OCF_3$, $—OCHF_2$, $—OCH_2F$ or $-(Z-A-)_n-R$; and n is 0, 1, 2 or 3;

where in the formula I, ring B does not stand for the formula C if $X^1$, $X^2$ and $X^3$ are simultaneously hydrogen, and in the formula I, ring B does not stand for the formula e if $X^2$ and $X^3$ are simultaneously fluorine or if $E^1$ is hydrogen and simultaneously $X^1$ and $X^2$ are fluorine.

Preference is given to cyclopenta[a]naphthalene derivatives of the general formulae I, III and V, and particular preference is given to cyclopenta[a]-naphthalene derivatives of the general formulae I and V.

The compounds all have negative $\Delta\epsilon$ and are therefore suitable, in particular, for use in VA-TFT displays. The compounds according to the invention preferably have a $\Delta\epsilon$ of $<-2$ and particularly preferably a $\Delta\epsilon$ of $<-5$. The dielectric anisotropy of the compounds according to the invention enables satisfactorily low characteristic voltages to be achieved, in particular in VA-TFT displays. The compounds exhibit very good compatibility with the usual substances used in liquid-crystal mixtures for displays.

Furthermore, the compounds of the formulae I to V according to the invention have values for the optical anisotropy An which are particularly suitable for use in VA-TFT displays. The compounds according to the invention preferably have a $\Delta n$ of greater than 0.02 and less than 0.20, particularly preferably less than 0.15.

The other physical, physicochemical or electro-optical parameters of the compounds according to the invention are also advantageous for use of the compounds in liquid-crystalline media. The compounds have, in particular, a sufficient breadth of the nematic phase and good low-temperature and long-term stability as well as sufficiently high clearing points and good viscosities and response times.

It is preferred for at least one of the radicals $X^1$, $X^2$ and $X^3$ or $X^{1a}$, $X^{1b}$, $X^2$ and $X^3$ on the naphthalene structure of the formula I, II, III, IV or V to be other than hydrogen.

It is furthermore preferred for ring B to have at least one electronegative substituent (—F or =O). These substituents on ring B are oriented in the same direction, i.e. the same side of the molecule, as the radicals $X^1$, $X^{1a}$, $X^{1b}$, $X^2$ and $X^3$.

The substituents $X^1$, $X^{1a}$, $X^{1b}$, $X^2$ and $X^3$, preferably $CF_3$, fluorine and/or chlorine substituents, in particular fluorine substituents, in the naphthalene structure and the electronegative atoms in ring B generate a dipole moment perpendicular to the longitudinal axis of the molecules, which can, if desired, be further strengthened by suitable substituents in the wing units $-(Z-A-)_n-R$. In the field-free state, the compounds of the formulae I to V orient themselves with their longitudinal axis of the molecules perpendicular to the treated or coated glass surface of the display.

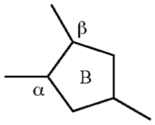

is preferably

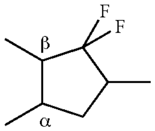

a

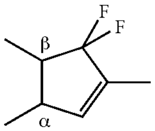

b

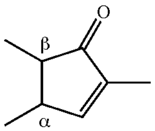

d

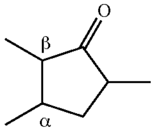

e

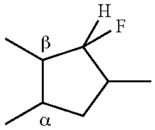

f

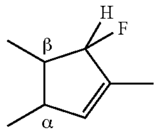

, or g

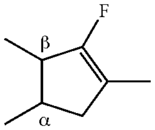

h particularly preferably the fluorine-substituted rings a, b, f, g and h, in particular ring a.

In the general formulae I to V, A are preferably, independently of one another (i.e. if n>1, so that a plurality of identical or different rings A are present), optionally substituted 1,4-phenylene, optionally substituted 1,4-cyclohexylene in which $-CH_2-$ may be replaced once or twice by —O—, or optionally substituted 1,4-cyclohexenylene.

A are particularly preferably, independently of one another,

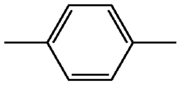
, 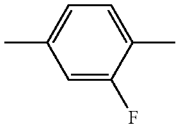
, 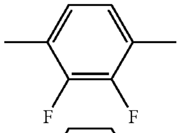
, 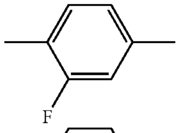
, 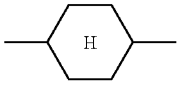
, 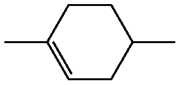
, 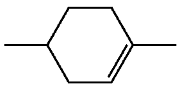
, 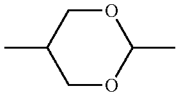
, 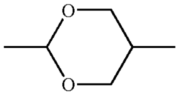
, 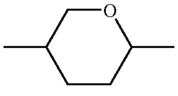
or 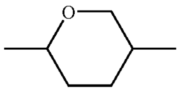
.

A are very particularly preferably 1,4-cyclohexylene rings and/or optionally mono- or poly-fluorine-substituted 1,4-phenylene rings.

If $E^1$ and/or $E^2$ are $-(Z-A-)_n-R$, A are preferably 1,4-cyclohexylene rings or optionally fluorine-substituted 1,4-phenylene rings.

Preferred groups Z in the compounds of the general formulae I to V are each, independently of one another, a single bond, $-CF_2O-$, $-OCF_2-$, $-CF_2CF_2-$, —CH═CH—, —CF═CH—, —CH═CF— or —CF═CF—, particularly preferably a single bond, $-CF_2O-$, $-OCF_2-$, $-CF_2CF_2-$, —CF═CH—, —CH═CF— or —CF═CF—. If $E^1$ and/or $E^2$ are $-(Z-A-)_n-R$, Z is in particular in each case a single bond.

R, $E^1$, $E^2$, $X^1$, $X^{1a}$, $X^{1b}$, $X^2$ and $X^3$ in the general formulae I to V may each, independently of one another, be an alkyl radical—i.e. an aliphatic saturated hydrocarbon radical—and/or an alkoxy radical (alkyloxy radical)—i.e. an aliphatic saturated hydrocarbon radical having a terminal O atom—having from 1 to 15 carbon atoms, which is straight-chain or branched. It is preferably straight-chain, has 1, 2, 3, 4, 5, 6 or 7 carbon atoms and accordingly is preferably methyl, ethyl, propyl, butyl, pentyl, hexyl, heptyl, methoxy, ethoxy, propoxy, butoxy, pentoxy, hexoxy or heptoxy.

R, $E^1$, $E^2$, $X^1$, $X^{1a}$, $X^{1b}$, $X^2$ and $X^3$ may each, independently of one another, be oxaalkyl—i.e. one of the non-terminal $CH_2$ groups in the alkyl radical has been replaced by —O——preferably straight-chain 2-oxapropyl (=methoxymethyl), 2-(=ethoxymethyl) or 3-oxabutyl (=methoxyethyl), 2-, 3- or 4-oxapentyl, 2-, 3-, 4- or 5-oxahexyl or 2-, 3-, 4-, 5- or 6-oxaheptyl. Correspondingly, R, $E^1$, $E^2$, $X^1$, $X^{1a}$, $X^{1b}$, $X^2$ and $X^3$ may also, independently of one another, be thioalkyl radicals, i.e. alkyl radicals in which a $CH_2$ group has been replaced by —S—.

R, $E^1$, $E^2$, $X^1$, $X^{1a}$, $X^{1b}$, $X^2$ and $X^3$ may furthermore each, independently of one another, be an alkenyl radical—i.e. an aliphatic hydrocarbon radical containing at least one C═C double bond—having from 2 to 15 carbon atoms, which is straight-chain or branched and contains at least one C—C double bond. It is preferably straight-chain and has from 2 to 7 carbon atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, or hept-1-, -2-, -3-, -4-, -5- or -6-enyl. If the two carbon atoms of the C—C double bond are substituted, the alkenyl radical may be in the form of the E- and/or Z-isomer (trans/cis). The respective E-isomers are generally preferred.

R, $E^1$, $E^2$, $X^1$, $X^{1a}$, $X^{1b}$, $X^2$ and $X^3$ may also, independently of one another, be an alkynyl radical having from 2 to 15 carbon atoms, which is straight-chain or branched and contains at least one C—C triple bond.

R, $E^1$, $E^2$, $X^1$, $X^{1a}$, $X^{1b}$, $X^2$ and $X^3$ may each, independently of one another, be an alkyl radical having from 1 to 15 carbon atoms in which one $CH_2$ group has been replaced by —O— and one has been replaced by —CO—, these preferably being adjacent. This thus contains an acyloxy group —CO—O— or an oxycarbonyl group —O—CO—. This radical is preferably straight-chain and has from 2 to 6 carbon atoms. Replacement of a $CH_2$ group by —CO— with formation of a keto group is also possible. The corresponding radical likewise preferably has from 2 to 6 carbon atoms.

R, $E^1$, $E^2$, $X^1$, $X^{1a}$, $X^{1b}$, $X^2$ and $X^3$ may each, independently of one another, be an alkyl radical having from 1 to 15 carbon atoms in which one $CH_2$ group has been replaced by unsubstituted or substituted —CH═CH— and an adjacent $CH_2$ group has been replaced by CO or CO—O or O—CO, where this may be straight-chain or branched. The radical is preferably straight-chain and has from 4 to 13 carbon atoms.

R, $E^1$ and $E^2$ may each, independently of one another, be an alkyl radical having from 1 to 15 carbon atoms or alkenyl radical having from 2 to 15 carbon atoms, each of which is monosubstituted by —CN or —$CF_3$, these preferably being straight-chain. Substitution by —CN or —$CF_3$ is possible in any desired position.

R, $E^1$, $E^2$, $X^1$, $X^{1a}$, $X^{1b}$, $X^2$ and $X^3$ may each, independently of one another, be an alkyl radical in which two or more $CH_2$ groups have been replaced by —O— and/or —CO—O—, where this may be straight-chain or branched. It is preferably branched and has from 3 to 12 carbon atoms.

R, $E^1$, $E^2$, $X^1$, $X^{1a}$, $X^{1b}$, $X^2$ and $X^3$ may each, independently of one another, be an alkyl radical or alkoxy radical having from 1 to 15 carbon atoms or alkenyl radical having from 2 to 15 carbon atoms, each of which is at least monosubstituted by halogen, where these radicals are preferably straight-chain and halogen is preferably —F or —Cl. In the case of polysubstitution, halogen is preferably —F. The resultant radicals also include perfluorinated radicals, such as —$CF_3$ and —$OCF_3$. In the case of monosubstitution, the fluorine or chlorine substituent can be in any desired position, but is preferably in the ω-position.

R in the general formulae I to V is particularly preferably an alkyl radical, alkoxy radical or alkenyl radical having from 1 to 7 or 2 to 7 carbon atoms respectively.

$E^1$ and $E^2$ in the general formulae I to V are preferably, independently of one another, hydrogen, an alkyl radical, alkoxy radical or alkenyl radical having from 1 to 7 or 2 to 7 carbon atoms respectively, a halogen or $-(-Z-A-)_n-R$, in which n is 1, Z is a single bond, A is 1,4-cyclohexylene or optionally fluorine-substituted 1,4-phenylene, and R is alkyl, alkoxy or alkenyl having from 1 to 7 or 2 to 7 carbon atoms respectively, particularly preferably hydrogen, an alkyl radical or alkoxy radical having from 1 to 7 carbon atoms, fluorine, chlorine, 4-alkyl-substituted 1,4-phenylene or 4-alkyl-substituted 1,4-cyclohexylene, and in particular fluorine.

$X^1$, $X^{1a}$, $X^{1b}$, $X^2$ and $X^3$ in the general formulae I to V are preferably, independently of one another, hydrogen, an alkyl radical, alkoxy radical or alkenyl radical having from 1 to 7 or 2 to 7 carbon atoms respectively which is at least monosubstituted by halogen, or a halogen. It is particularly preferred here for at least one of $X^1$, $X^2$ and $X^3$ or $X^{1a}$, $X^{1b}$, $X^2$ and $X^3$ to be —$CF_3$, F or Cl. Very particularly preferably, all of $X^1$, $X^2$ and $X^3$ or $X^{1a}$, $X^{1b}$, $X^2$ and $X^3$ are —$CF_3$, fluorine or chlorine, and in particular all are fluorine.

Preferred compounds of the general formulae I to V contain a total of zero, one or two wing units ZA, i.e. n=0, 1 or 2. If a wing group ZA is present (n=1), it can be bonded to the cyclopentane ring or to the naphthalene structure ($E^1$, $E^2$=-Z-A-R). If n is 2 or 3, the two or three wing groups ZA may be bonded to only one side of the molecule—to the cyclopentane ring or as $E^1$ or $E^2$ to the naphthalene structure—or alternatively to both sides of the molecule—to the cyclopentane ring and as $E^1$ or $E^2$ to the naphthalene structure. n is particularly preferably 0 or 1.

In connection with the present invention, halogen is fluorine, chlorine, bromine or iodine.

The compounds of the general formulae I to V are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can be made here of variants which are known per se, but are not mentioned here in greater detail.

If desired, the starting materials can also be formed in situ by not isolating them from the reaction mixture, but instead immediately converting them further into the compounds of the general formulae I to V.

The syntheses of various polysubstituted naphthalene derivatives which are used to build up the five-membered ring are described by way of example in the examples. The starting substances are obtainable by generally accessible literature procedures or are commercially available. The reactions described should likewise be regarded as known from the literature.

An illustrative synthesis for building up the five-membered ring is shown below. The synthesis can be adapted to the particular desired compounds of the general formulae I to V through the choice of suitable starting materials.

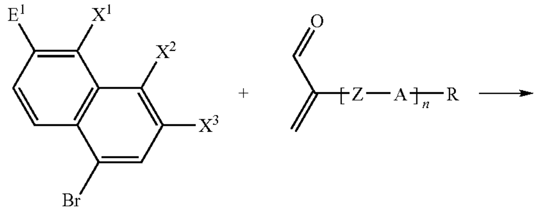

A B

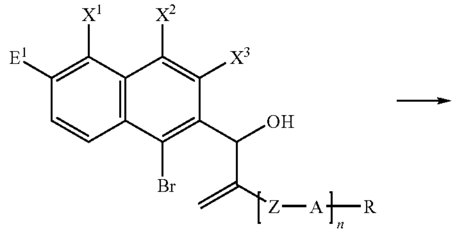

C

-continued

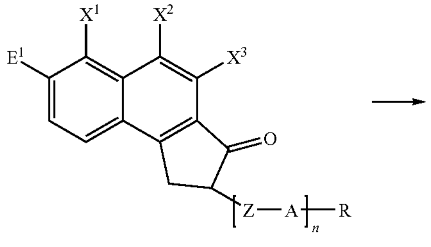

D

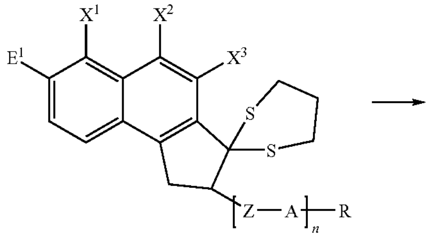

E

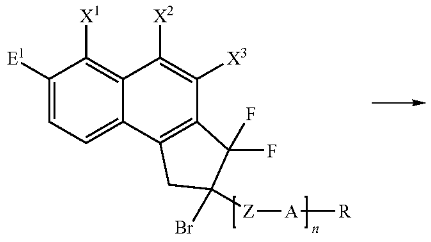

F

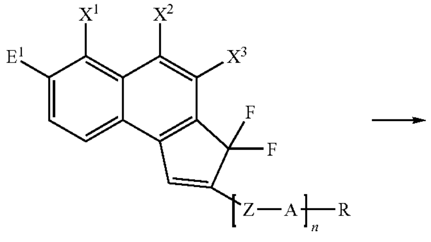

G

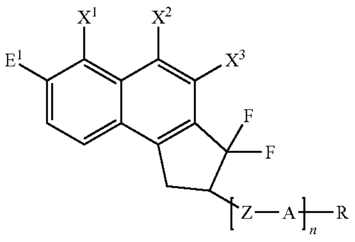

H

Starting from the 4-bromonaphthalene derivative A, reaction with an α,β-unsaturated aldehyde B in the presence of lithium diisopropylamide (LDA) gives compound C. This reacts with palladium catalysis in the presence of triethylamine with ring closure to give the ketone D (=compound Ie). Starting from the ketone D and 1,3-propanedithiol in the presence of $BF_3$/diethyl ether, the corresponding dithiane E is obtained. This is reacted with 1,3-dibromo-5,5-dimethylhydantoin (DBH) and HF in pyridine to give the cyclopenta[a]naphthalene derivative F. Elimination of HBr in the presence of diazabicycloundecene (DBU) gives the cyclopenta[a]naphthalene derivative G (=compound Ib). The cyclopenta[a]naphthalene derivative G is hydrogenated on a palladium/carbon catalyst in a hydrogen atmosphere to give the cyclopenta[a]naphthalene derivative H (=compound Ia).

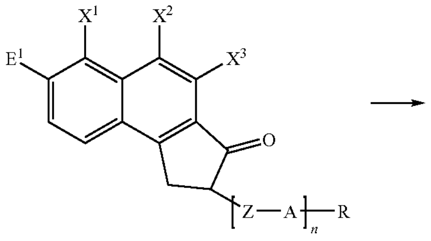

D

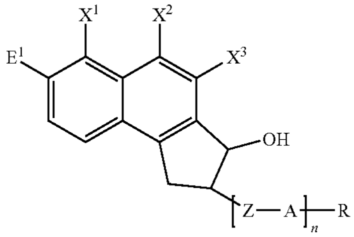

J

J

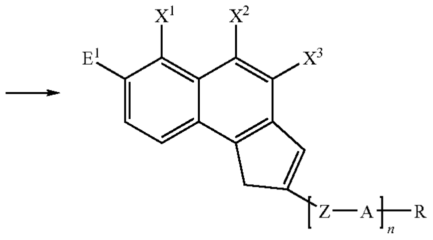

K

J

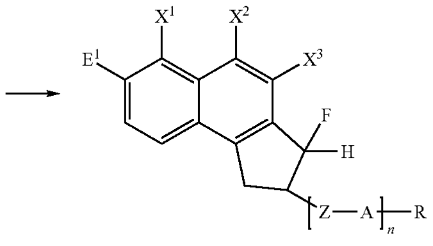

L

Starting from the ketone D (which, in addition, can also be prepared analogously to US 2003/0108684 A1, scheme 4), reduction, for example using $LiAlH_4$, firstly gives access to the alcohol J, from which on the one hand the cyclopenta[a]naphthalene derivative K (=compound Ii) is accessible by subsequent elimination using acid and on the other hand the cyclopenta[a]naphthalene derivative L (=compound If) is accessible using DAST (diaminosulfur trifluoride; cf. M. Hudlicky, Organic Reactions, 35, 1988, 513) analogously to DE 44 34 975 A1.

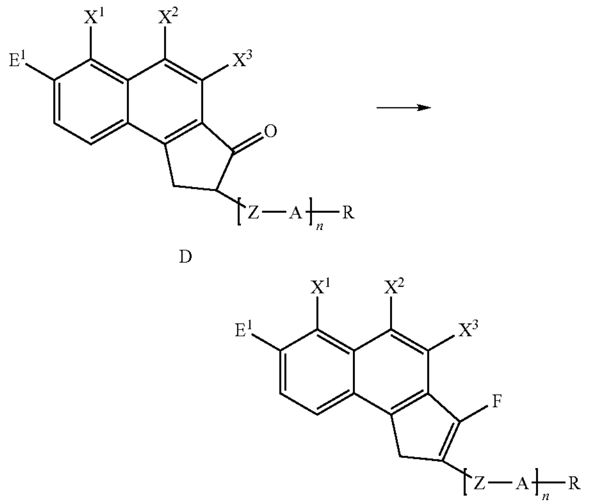

D

M

Starting from the ketone D, the cyclopenta[a]naphthalene derivative M (=compound Ih) is furthermore accessible by reaction with DAST analogously to the process disclosed in DE 44 34 975 A1.

The reactions described should only be regarded as illustrative. The person skilled in the art can carry out corresponding variations of the syntheses described and also follow other suitable synthetic routes in order to obtain compounds of the formulae I to V.

As already mentioned, the compounds of the general formulae I to V can be used in liquid-crystalline media.

The present invention therefore also relates to a liquid-crystalline medium comprising at least two liquid-crystalline compounds, comprising at least one compound of the general formulae I to V.

The present invention also relates to liquid-crystalline media comprising from 2 to 40, preferably from 4 to 30, components as further constituents besides one or more compounds of the formulae I, II, III, IV and/or V according to the invention. These media particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters, of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4',4'-biscyclohexylbiphenyls, phenyl- or cyclohexylpyrimidines, phenyl- or cyclo-hexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids, as well as corresponding compounds in which two carbocyclic and/or heterocyclic rings or ring systems (for example cyclohexyls, phenyls, dioxanes, tetrahydropyrans) are linked via a difluorooxymethylene bridge (—$CF_2O$—). The 1,4-phenylene groups in these compounds may also be mono- or polyfluorinated.

The most important compounds suitable as further constituents of media according to the invention can be characterised by the formulae (VI), (VII), (VIII), (IX) and (X):

R'-L-E-R" (VI)

R'-L-COO-E-R" (VII)

R'-L-OOC-E-R" (VII)

R'-L-$CH_2CH_2$-E-R" (IX)

R'-L—$CF_2O$-E-R" (X)

In the formulae (VI), (VII), (VIII), (IX) and (X), L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -Thp-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl, Thp- is tetrahydropyran-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc or Phe. E is preferably Cyc, Phe or Phe-Cyc. The media according to the invention preferably comprise one or more components selected from the compounds of the formulae (VI), (VII), (VIII), (IX) and (X) in which L and E are selected from the group consisting of Cyc and Phe and simultaneously one or more components selected from the compounds of the formulae (VI), (VII), (VIII), (IX) and (X) in which one of the radicals L and E is selected from the group consisting of Cyc and Phe and the other radical is selected from the group consisting of -Phe-Phe-, -Phe-Cyc-, -Cyc-Cyc-, -G-Phe- and -G-Cyc-, and optionally one or more components selected from the compounds of the formulae (VI), (VII), (VIII), (IX) and (X) in which the radicals L and E are selected from the group consisting of -Phe-Cyc-, -Cyc-Cyc-, -G-Phe- and -G-Cyc-.

In a smaller sub-group of the compounds of the formulae (VI), (VII), (VIII), (IX) and (X), R' and R" are each, independently of one another, alkyl, alkenyl, alkoxy, alkoxyalkyl (oxaalkyl), alkenyloxy or alkanoyloxy having up to 8 carbon atoms. This smaller sub-group is called group A below, and the compounds are referred to by the sub-formulae (VIa), (VIIa), (VIIIa), (IXa) and (Xa). In most of these compounds, R' and R" are different from one another, one of these radicals usually being alkyl, alkenyl, alkoxy or alkoxy-alkyl (oxaalkyl).

In another smaller sub-group of the compounds of the formulae (VI), (VII), (VIII), (IX) and (X), which is known as group B, E is

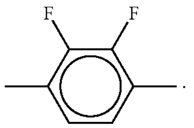

In the compounds of group B, which are referred to by the sub-formulae (VIb), (VIIb), (VIIIb), (IXb) and (Xb), R' and R" are as defined for the compounds of the sub-formulae (VIa) to (Xa) and are preferably alkyl, alkenyl, alkoxy or alkoxyalkyl (oxaalkyl).

In a further smaller sub-group of the compounds of the formulae (VI), (VII), (VIII), (IX) and (X), R" is —CN. This sub-group is referred to below as group C, and the compounds of this sub-group are correspondingly described by sub-formulae (VIc), (VIIc), (VIIIc), (IXc) and (Xc). In the compounds of the sub-formulae (VIc), (VIIc), (VIIIc), (IXc) and (Xc), R' is as defined for the compounds of the sub-formulae (VIa) to (Xa) and is preferably alkyl, alkenyl, alkoxy or alkoxyalkyl (oxaalkyl).

Besides the preferred compounds of groups A, B and C, other compounds of the formulae (VI), (VII), (VIII), (IX) and (X) having other variants of the proposed substituents are also customary. All these substances are obtainable by methods which are known from the literature or analogously thereto.

Besides the compounds of the general formulae I, II, III, IV and/or V according to the invention, the media according to the invention preferably comprise one or more compounds from groups A, B and/or C. The proportions by weight of the compounds from these groups in the media according to the invention are:

group A: from 0 to 90%, preferably from 20 to 90%, in particular from 30 to 90% group B: from 0 to 80%, preferably from 10 to 80%, in particular from 10 to 70% group C: from 0 to 80%, preferably from 5 to 80%, in particular from 5 to 50%.

The media according to the invention preferably comprise from 1 to 40%, particularly preferably from 5 to 30%, of the compounds of the formulae I, II, III, IV and/or V according to the invention. Preference is furthermore given to media comprising more than 40%, in particular from 45 to 90%, of compounds of the formulae I, II, III, IV and/or V according to the invention. The media preferably comprise one, two, three, four or five compounds of the formulae I, II, III, IV and/or V according to the invention.

Examples of the compounds of the formulae (VI), (VII), (VIII), (IX) and (X) are the compounds listed below:

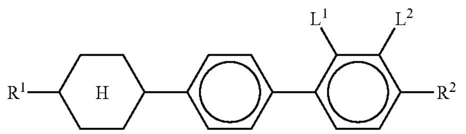

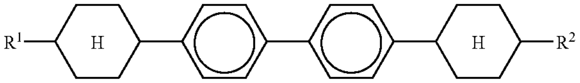

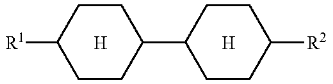

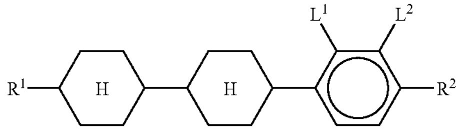

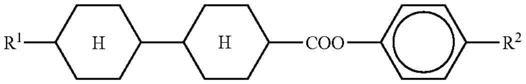

-continued

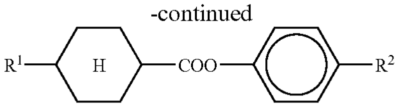

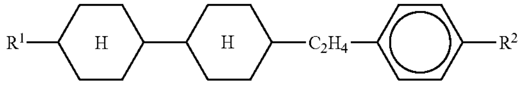

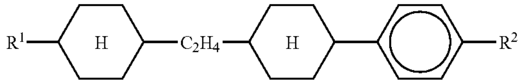

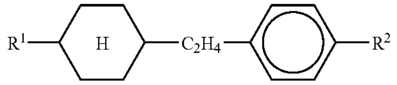

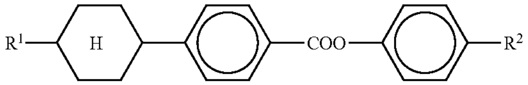

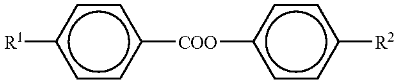

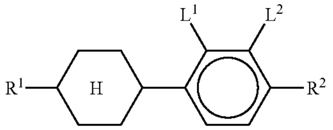

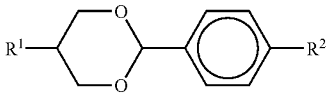

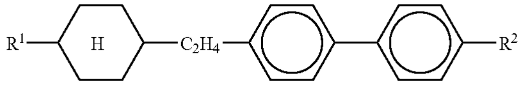

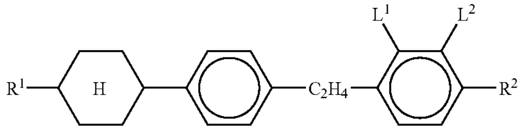

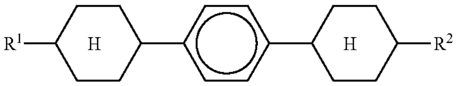

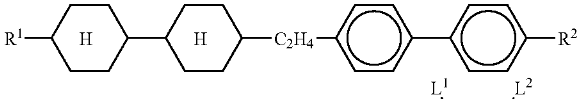

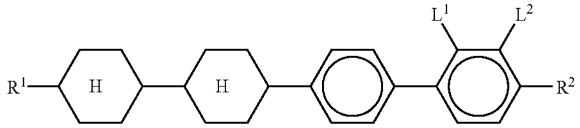

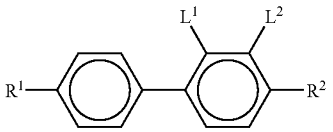

where $R^1$ and $R^2$, independently of one another, are $—C_nH_{2n+1}$ or $—OC_nH_{2n+1}$, and n=1, 2, 3, 4, 5, 6, 7 or 8, and $L^1$ and $L^2$, independently of one another, are —H or —F,

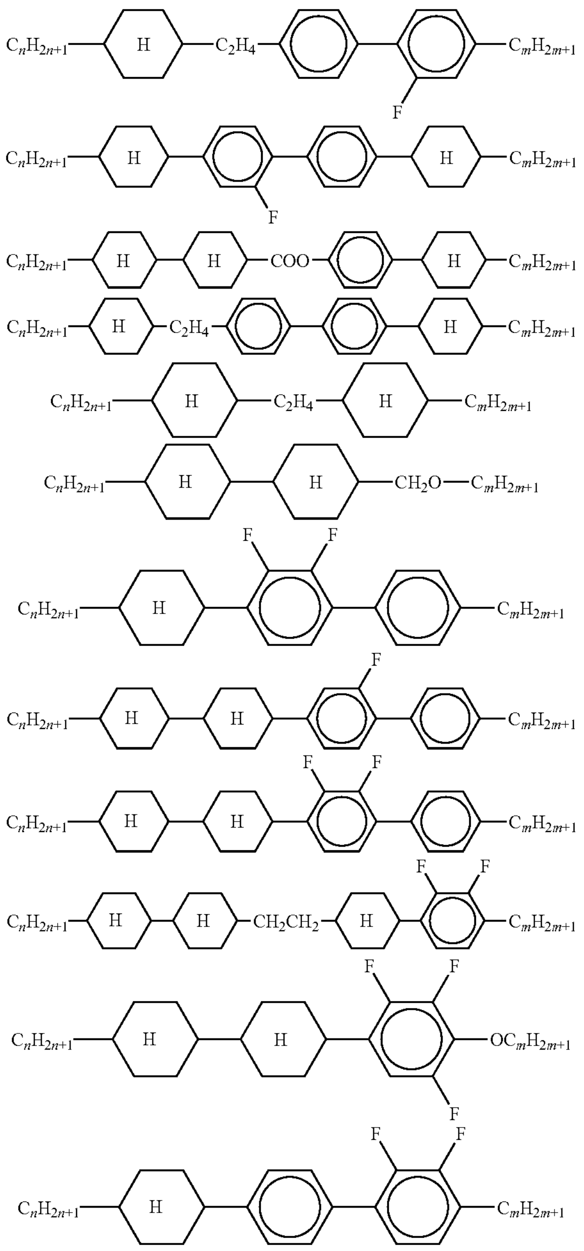

where m and n, independently of one another, are 1, 2, 3, 4, 5, 6, 7 or 8.

The media according to the invention are prepared in a manner conventional per se. In general, the components are dissolved in one another, advantageously at elevated temperature. By means of suitable additives, the liquid-crystalline phases of the present invention can be modified in such a way that they can be used in all types of liquid-crystal display element that have been disclosed hitherto. Additives of this type are known to the person skilled in the art and are described in detail in the literature (H. Kelker/R. Hatz, Handbook of Liquid Crystals, Verlag Chemie, Weinheim, 1980). For example, pleochroic dyes can be used for the preparation of coloured guest-host systems or substances can be added in order to modify the dielectric anisotropy, the viscosity and/or the alignment of the nematic phases.

Owing to their negative Δϵ, the compounds of the formulae I to V are particularly suitable for use in VA-TFT displays.

The present invention therefore also relates to electro-optical liquid-crystal display elements containing a liquid-crystalline medium according to the invention.

The invention is explained in greater detail below with reference to working examples, but without being restricted thereby.

EXAMPLES

The starting substances can be obtained by generally accessible literature procedures or are commercially available. The reactions described are known from the literature.

Example 1

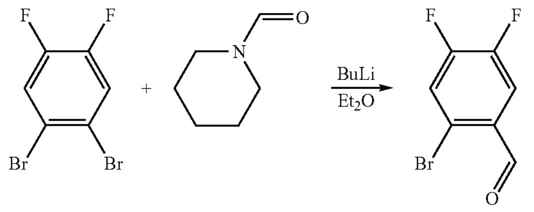

1 2 3

38.8 ml (95.0 mmol) of a 2.5M butyllithium solution in hexane were added at −75° C. to a solution of 25.0 g (92.0 mmol) of the aromatic compound 1 in 200 ml of diethyl ether, and the mixture was stirred for 1 hour. 13.4 ml (120 mmol) of formylpiperidine (2) in 15 ml of diethyl ether were subsequently added at T<−55° C. After a further hour, the batch was warmed to room temperature, water was added, and the mixture was acidified. Extraction, drying, evaporation and chromatography on silica gel gave 14.2 g (70%) of the aldehyde 3.

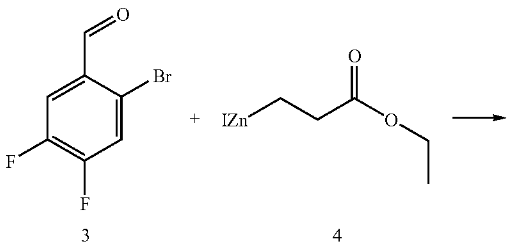

3 4

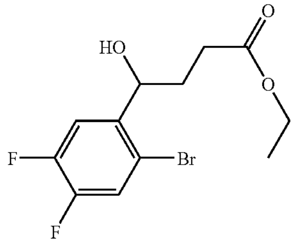

5

200 ml (100 mmol) of a 0.5M solution of the zinc compound 4 in THF were added at −75° C. to a solution of 26.8 g (98.5 mmol) of the aldehyde 3 in 100 ml of THF. After 30 minutes, the cooling was removed. Water was added to the thawed batch, which was then acidified using 1 N HCl solution and extracted with methyl tert-butyl ether. Drying, evaporation and chromatography on silica gel gave 28.6 g (90%) of the hydroxy ester 5.

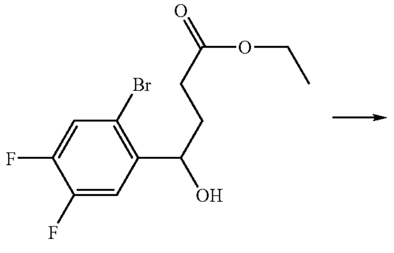

5

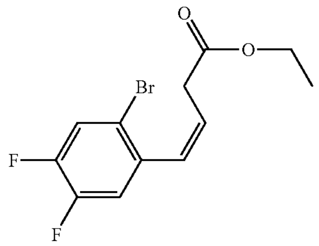

6

20.0 g (61.9 mmol) of the hydroxy ester 5 were dissolved in 200 ml of toluene, 1 g of p-toluenesulfonic acid was added, and the mixture was refluxed until the water separation was complete. Evaporation and filtration through silica gel gave 16.4 g (87%) of the ester 6.

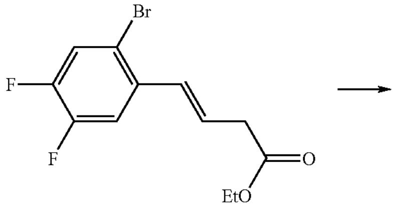

6

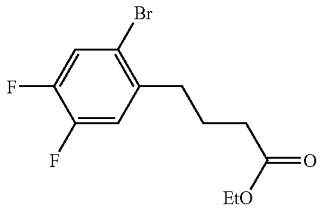

7

15.0 g (49.2 mmol) of the unsaturated ester 6 were hydrogenated on a palladium catalyst (5%/C) in tetrahydrofuran (THF). Yield: 14.5 g (96%) of the ester 7.

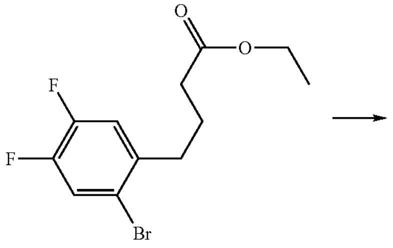

7

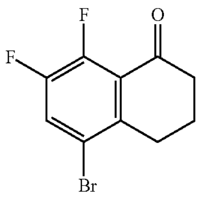

9.0 g (29.3 mmol) of the ester 7 were added at 60° C. to 100 g of polyphosphoric acid. The temperature was subsequently increased to 120° C. for 4 hours. After cooling, the batch was added to ice and extracted with methyl tert-butyl ether. Drying, evaporation and crystallisation gave 4.8 g (63%) of the ketone 8.

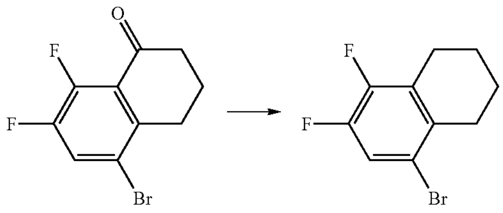

8 9

5.0 g (19.2 mmol) of the oxo compound 8 were dissolved in 40 ml of diethylene glycol dimethyl ether, and 2.3 g (58.5 mmol) of sodium borohydride were added with ice-cooling. 9 ml of boron trifluoride/diethyl ether complex were subsequently added. After 2 hours at room temp., the batch was added to sat. sodium hydrogencarbonate solution. The aqueous phase was extracted with dichloromethane. Drying, evaporation and chromatography on silica gel gave 4.3 g (90%) of the tetrahydronaphthalene 9.

Compounds according to the invention are accessible from compounds 8 and 9 or analogous compounds, as is evident to the person skilled in the art, inter alia from the description and the further examples.

Example 2

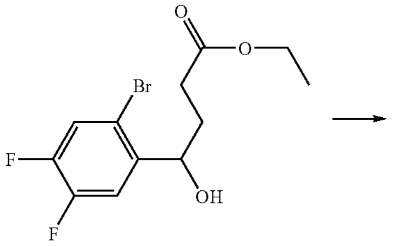

5

-continued

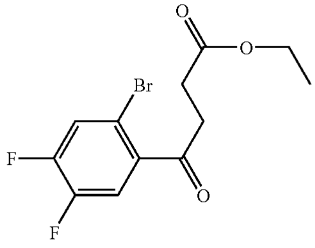

10

A solution of 10.6 g (32.7 mmol) of the hydroxy ester 5 was added at room temp. to a suspension of 40.0 mmol of PCC on 50 g of Celite® in 150 ml of dichloromethane. When the reaction was complete (TLC), the batch was filtered, and the filter cake was washed with methylene chloride. Evaporation and chromatography on silica gel gave 10.1 g (96%) of the oxo ester 10.

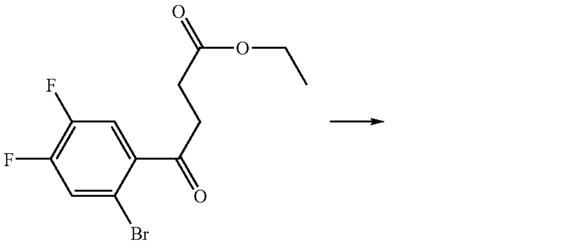

10

11

The ring closure was carried out as described above for compound 7. Yield: 61 %.

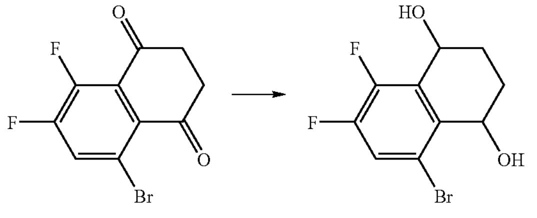

11 12

8.6 g (31.1 mmol) of the dione 11 were dissolved in 150 ml of ethanol, and 2.4 g (65.0 mmol) of sodium borohydride were added in portions. When the reaction was complete (TLC), the batch was hydrolysed using water, the ethanol was removed under reduced pressure, and the residue was taken up in water and extracted with toluene. After evaporation, the product 12 was employed in the next step without further purification.

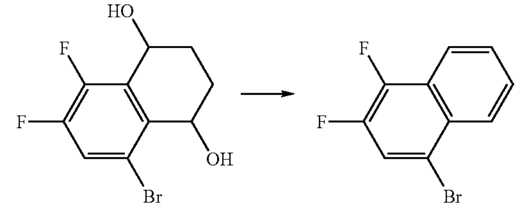

12 13

10.0 g of the crude diol 12 were dissolved in 200 ml of toluene, 1 g of p-toluenesulfonic acid was added, and the mixture was refluxed until the water separation was complete. Evaporation and filtration through silica gel gave 8.0 g (92%) of the naphthalene 13. Compounds according to the invention are accessible therefrom (or from analogous compounds), as is evident to the person skilled in the art, inter alia from the description and the further examples.

Example 3

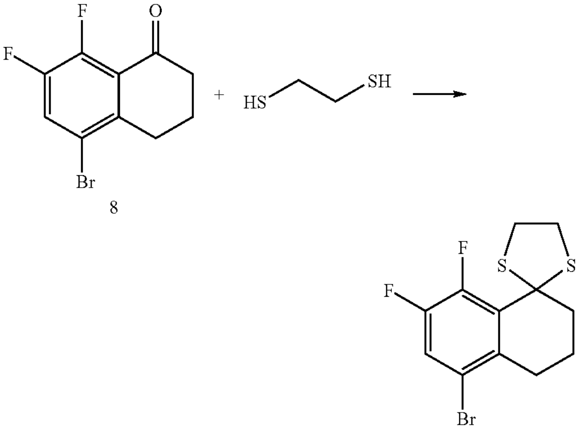

8

14

30 ml of boron trifluoride/diethyl ether complex were added under nitrogen to a solution of 13.1 g (50.0 mmol) of the ketone 8 and 8.4 ml (100 mmol) of the dithiol in 150 ml of dichloromethane, and the mixture was stirred overnight. The batch was added slowly to sat. sodium hydrogencarbonate solution and deacidified. Drying, evaporation and chromatography on silica gel gave 17.2 g (92%) of the protected ketone 14.

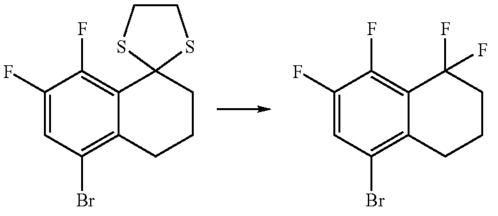

14 15

A solution of 9.3 g (25.0 mmol) of the dithiolane 14 in 60 ml of dichloromethane was added at −75° C. to a suspension of 30.2 g (105.2 mmol) of 1,3-dibromo-5,5-dimethylhydantoin in 60 ml of dichloromethane and 120 ml of a 65% solution of hydrogen fluoride in pyridine. The batch was slowly warmed to 0° C. over the course of 3 hours and added to 1500 ml of ice-cooled 2N sodium hydroxide solution to which 120 ml of 39% sodium hydrogensulfite solution had been added. The pH was adjusted to 8, and the aqueous phase was extracted with methylene chloride. Drying, evaporation and chromatography on silica gel gave 5.2 g (73%) of the fluorinated aromatic compound 15. Compounds according to the invention are accessible therefrom (or from analogous compounds), as is evident to the person skilled in the art, inter alia from the description and the further examples.

Example 4

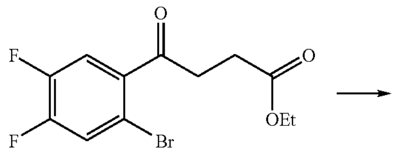

10

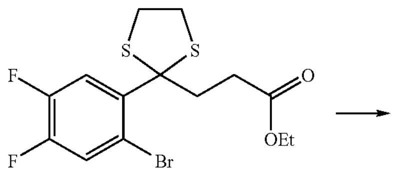

16

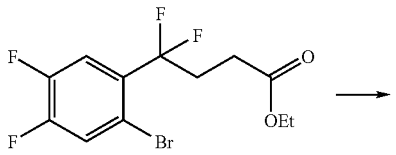

17

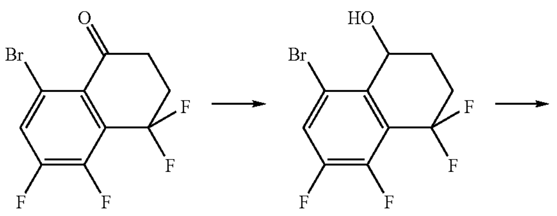

18 19

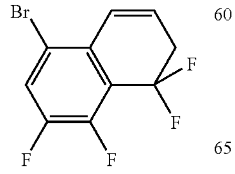

20

The synthesis is carried out in accordance with the reactions described above, with the elimination of water from 19 to give 20 likewise being effected using p-toluenesulfonic acid. Overall yield: 30%.

Example 5

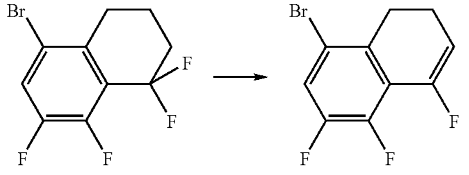

15 22

A solution of 9.0 g (23.6 mmol) of 15 in 50 ml of THF was slowly added to a suspension of 4.5 g (40.1 mmol) of potassium tert-butoxide in 50 ml of THF, and the mixture was subsequently refluxed overnight. The cooled batch was diluted with water and extracted with diethyl ether. Drying, evaporation and chromatography on silica gel gave 7.2 g (85%) of the styrene derivative 22.

Example 6

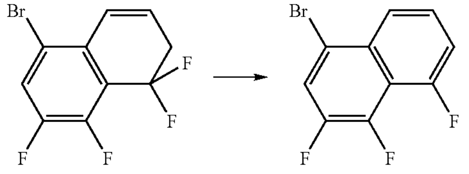

20 21

The reaction was carried out as described above. Yield: 81 %. Compounds according to the invention are accessible from compounds 20, 21 and 22 (or analogous compounds), as is evident to the person skilled in the art, inter alia from the description and the following examples.

Example 7

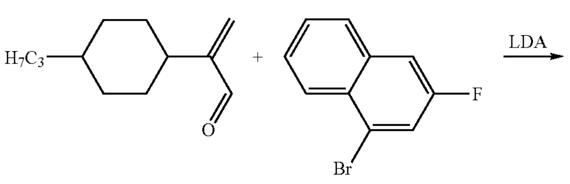

23 24

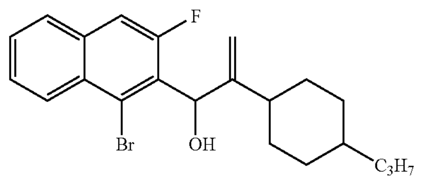

25

A solution of 13.5 g (60.0 mmol) of the bromofluoronaphthalene 24 in 10 ml of THF is added at −75° C. to 27.0 ml of a solution of 2N lithium diisopropylamide (LDA) in cyclohexane/ethylbenzene/THF (52.4 mmol) which has been diluted with 100 ml of THF. After 2 hours at the low temperature, 8.5 g (47.3 mmol) of the aldehyde 23 in 10 ml of THF are added. After 30 minutes, the cooling is removed, and 100 ml of 1 N HCl are added to the batch at 20° C. Extraction of the aqueous phase, drying of the organic phase, evaporation and chromatography gives the allyl alcohol 25.

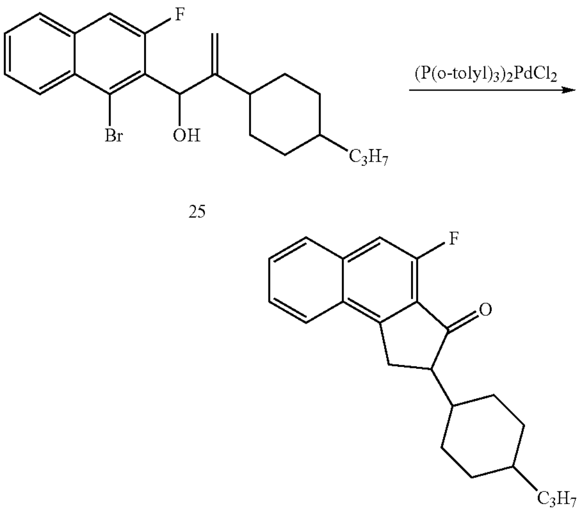

25

26

35.0 g (86.6 mmol) of the allyl alcohol 25, 5.5 g of bis(tri-o-tolylphosphine)-palladium dichloride and 50 ml of triethylamine are dissolved in 390 ml of acetonitrile and heated to 90° C. until the allyl alcohol has completely reacted. The cooled batch is introduced into water. Extraction, drying, evaporation and chromatography gives the ketone 26.

Example 8

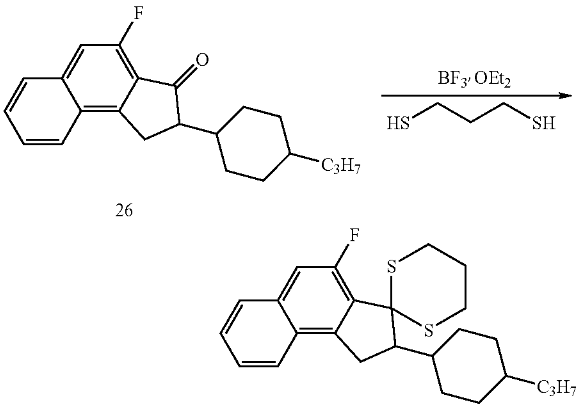

26

27

10.0 g (30.8 mmol) of the ketone 26 and 3.2 ml (31.0 mmol) of propane-dithiol are dissolved in 50 ml of dichloromethane, 7.0 ml of boron trifluoride/diethyl ether complex are added at from 6 to 7° C., and the mixture is subsequently stirred overnight at room temperature. The batch is introduced into 10 ml of saturated sodium hydrogencarbonate solution and stirred until the evolution of gas is complete. After extraction of the aqueous phase, drying of the organic phase, evaporation and filtration through silica gel, the resultant residue is employed in the next step without further purification.

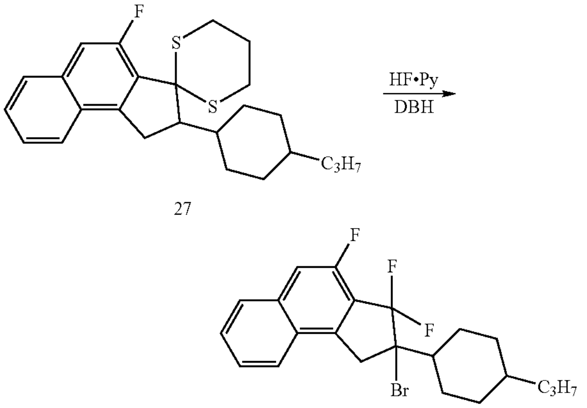

27

28

10.0 g of the crude thioketal 27, dissolved in 30 ml of dichloromethane, are added slowly at −75° C. to a mixture of 28.6 g (100 mmol) of 1,3-dibromo-5,5-dimethylhydantoin (DBH), 80 ml of a 65% solution of hydrogen fluoride in pyridine and 50 ml of dichloromethane. The batch is subsequently stirred overnight at room temperature. The reaction mixture is added to ice-cooled hydrogen sulfite solution and deacidified using saturated sodium hydrogencarbonate solution and sodium hydroxide solution. Extraction, drying, evaporation, re-washing with water, chromatography and crystallisation from hexane gives the cyclopenta[a]naphthalene derivative 28.

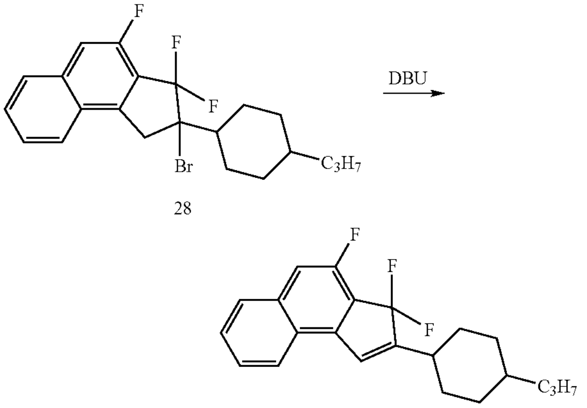

28

29

6.0 g (14.1 mmol) of the cyclopenta[a]naphthalene derivative 28 are dissolved in 50 ml of dichloromethane, 2.4 ml (16.0 mmol) of 1,8-diazabicyclo[5.4.0]undec-7-ene (DBU) are added, and the mixture is stirred at room temperature until the starting material has completely reacted. The batch is washed with water and saturated sodium chloride solution, evaporated and chromatographed. The cyclopenta[a]naphthalene derivative 29 is isolated.

Example 9

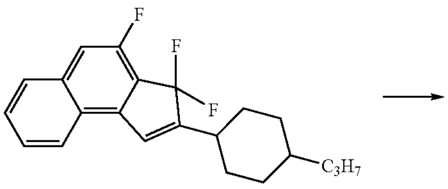

29

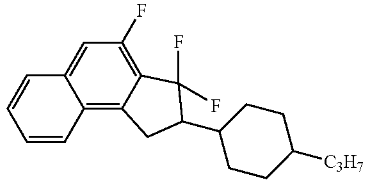

30

4.0 g (11.6 mmol) of the cyclopenta[a]naphthalene derivative 29 are dissolved in 50 ml of THF and hydrogenated at room temperature and atmospheric pressure on a palladium catalyst. Evaporation, chromatography on silica gel and crystallisation gives the cyclopenta[a]naphthalene derivative 30.

Example 10

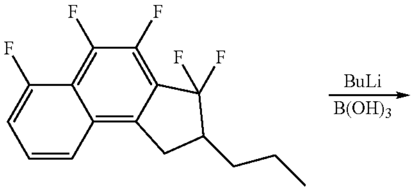

31

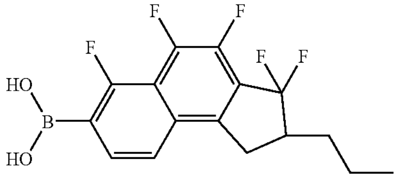

32

The cyclopenta[a]naphthalene derivative 31 prepared analogously to Examples 7 to 9 was converted into the cyclopenta[a]naphthalene derivative 32 as follows: under nitrogen and at −70° C., 4.5 ml (7.20 mmol) of a 15% solution of butyllithium in n-hexane were added to a solution of 2.5 g (7.18 mmol) of the naphthalene derivative 31 in 60 ml of THF. After 1 hour, 0.91 ml (8.0 mmol) of trimethyl borate was added to the batch. When the addition was complete, the cooling was removed, and the batch was hydrolysed at 10° C. The reaction mixture was acidified using 2N HCl solution. The aqueous phase was extracted with methyl tert-butyl ether. The organic phase was washed with sat. NaCl solution, dried over sodium sulfate and evaporated. The residue, which contained the boronic acid 32, was employed in the next step without further purification.

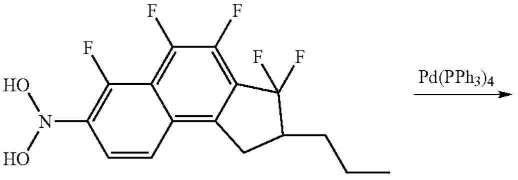

32

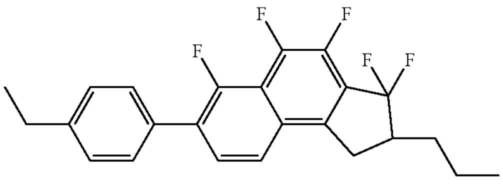

33

1.3 g (5.0 mmol) of sodium metaborate octahydrate were dissolved in 2.0 ml of water under a nitrogen atmosphere, and 83 mg of bis(triphenylphosphine)palladium(II)chloride, 50 μl of hydrazinium hydroxide and 1.11 g (6.0 mmol) of p-bromoethylbenzene were added successively. After 5 minutes at room temperature, 2.1 g (6.0 mmol) of the boronic acid dissolved in 3.75 ml of THF were added to the batch, and the mixture was heated at the boil overnight. The aqueous phase was extracted with methyl tert-butyl ether, and the organic phase was washed with water, dried and evaporated. The purification was carried out by means of multiple chromatography on silica gel (heptane).

Example 11

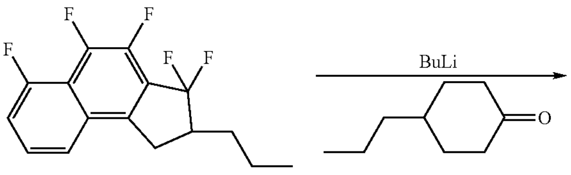

31

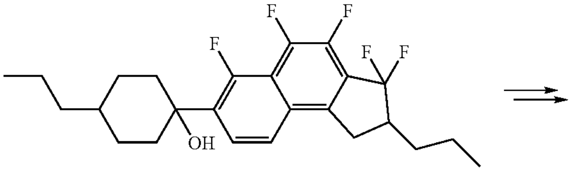

34

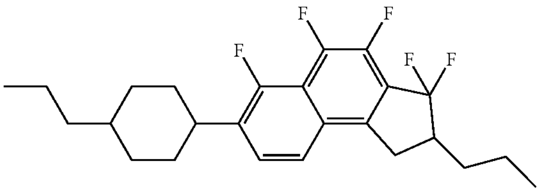

35

The cyclopenta[a]naphthalene derivative 31 was converted into the cyclopenta[a]naphthalene derivative 35 as follows:

Under nitrogen and at −70° C., 4.5 ml (7.20 mmol) of a 15% solution of butyllithium in n-hexane were added to a solution of 2.5 g (7.18 mmol) of the naphthalene derivative 31 in 60 ml of THF. After 1 hour, 1.1 g (8.0 mmol) of 4-propylcyclohexanone in 5 ml of THF were added to the batch. After 1 hour, the cooling was removed, and the batch was hydrolysed at 10° C. The reaction mixture was acidified using 2N HCl solution. The aqueous phase was extracted with methyl tert-butyl ether. The organic phase was washed with sat. NaCl solution, dried over sodium sulfate and evaporated. The residue was passed through silica gel (methyl tert-butyl ether/heptane 1:10).

A mixture of 50 ml of pyridine and 50 ml of phosphoryl chloride was added to a solution of 3.6 g (7.0 mmol) of the benzyl alcohol 34 in 30 ml of pyridine at such a rate that the batch boiled. After 4 hours, the batch was carefully poured into ice/water. The aqueous phase was extracted with dichloromethane; the organic phase was washed with sat. NaCl solution, dried over sodium sulfate, evaporated and passed through silica gel (hexane). 2.0 g (4.0 mmol) of the resultant elimination product were dissolved in 20 ml of THF and hydrogenated on a Pd catalyst until the uptake of hydrogen was complete. The catalyst was separated off, and the solution was evaporated. The residue was passed through silica gel (hexane), giving 35 after removal of the solvent.

Example 12

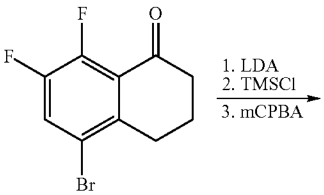

8

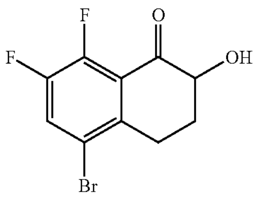

36

5.0 g (19.2 mmol) of the ketone 8, dissolved in 30 ml of THF, were added at −70° C. to a mixture of 40 ml of THF, 5.2 ml (41.2 mmol) of trimethylsilyl chloride and 10.3 ml (20 mmol) of a 2M solution of lithium diisopropylamide. After 30 minutes, 40 ml of triethylamine and sat. sodium hydrogencarbonate solution were added to the batch. The aqueous phase was extracted with methyl tert-butyl ether. The organic phase was dried over sodium sulfate, evaporated and filtered through silica gel (methyl tert-butyl ether/pentane 1:20).

The residue was taken up in 40 ml of THF, and a solution of 4.9 g (20.0 mmol) of m-chloroperbenzoic acid in 20 ml of THF was added at 0° C. After 1 hour, water was added to the batch, which was then extracted with methyl tert-butyl ether. The organic phase was dried over sodium sulfate, evaporated and filtered through silica gel (methyl tert-butyl ether/heptane 1:5), giving 4.4 g (80%) of the hydroxy ketone 36.

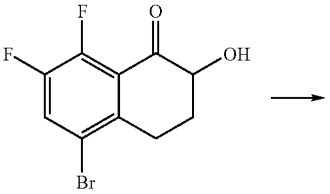

36

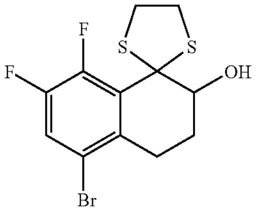

37

The synthesis of the thioketal 37 was carried out as already described in Example 3 for compound 14.

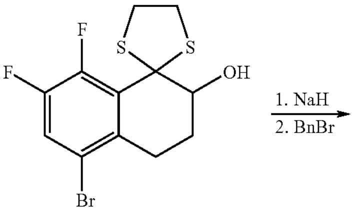

37

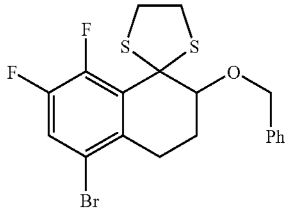

38

A solution of 14.1 g (40.0 mmol) of the thioketal 37 in 20 ml of THF was added to a suspension of 1.8 g (60%, 45.7 mmol) of sodium hydride in 40 ml of THF. After 2 hours, 500 mg of tetrabutylammonium iodide and 5.5 ml (45.7 mmol) of benzyl bromide in 20 ml of THF were added to the suspension. The batch was stirred overnight and subsequently carefully hydrolysed. The aqueous phase was extracted with methyl tert-butyl ether. The organic phase was dried over sodium sulfate, evaporated and passed through silica gel (methyl tert-butyl ether/heptane 1:20), giving 16.1 g (91%) of the benzyl ether 38.

The alcohol 39 can be prepared from 38 analogously to the processes of Examples 7 to 9. During the preparation of the intermediate thioketal, the benzyl ether is cleaved. The protecting group must then be re-introduced in the manner already described.

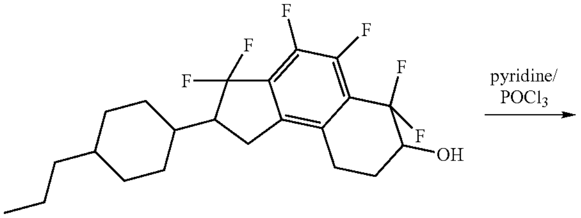

39

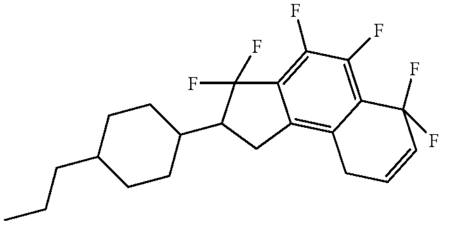

40

A mixture of 50 ml of pyridine and 50 ml of phosphoryl chloride was added to a solution of 2.9 g (7.0 mmol) of the naphthalene 39 in 30 ml of pyridine at such a rate that the batch boiled. After 4 hours, the batch was carefully poured onto ice. The aqueous phase was extracted with dichloromethane, and the organic phase was washed with sat. NaCl solution, dried over sodium sulfate, evaporated and passed through silica gel (hexane), giving 1.7 g (62%) of the unsaturated compound 40.

Example 13

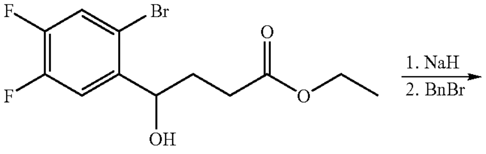

5

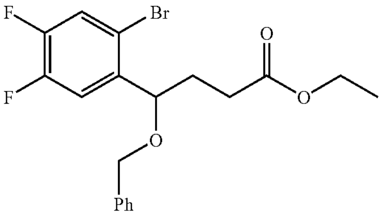

41

The synthesis is carried out in accordance with the procedure indicated above in Example 12 for compound 38.

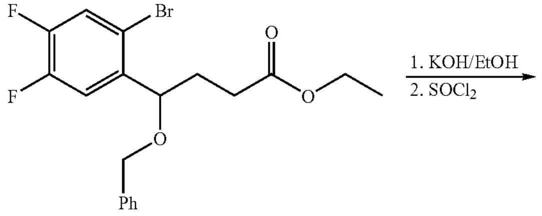

41

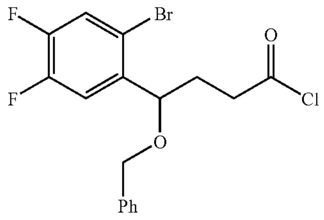

42

An ethanolic potassium hydroxide solution was added to 7.3 g (17.7 mmol) of the ester 41, and the mixture was refluxed until the reaction was complete (TLC). The alcohol was removed in a rotary evaporator. The residue was taken up in water and acidified. After extraction with methyl tert-butyl ether, the organic phase was dried over sodium sulfate, and the solvent was removed. Thionyl chloride and one drop of DMF were added to the resultant residue, and the mixture was refluxed until the evolution of gas was complete. Excess thionyl chloride was distilled off. The crude product 42 was employed in the next step without further purification.

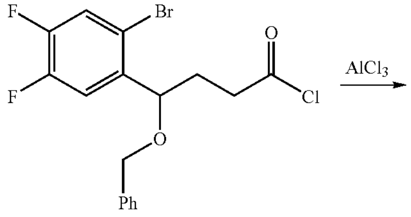

42

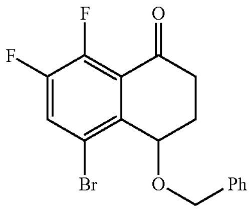

43

A solution of the acid chloride 42 in 50 ml of dichloromethane was added slowly at 0° C. to a suspension of 4 g of aluminium chloride in 50 ml of dichloromethane. When the addition was complete, the reaction was monitored by TLC. When the reaction was complete, ice was carefully added to the batch. When the evolution of HCl had subsided, the mixture was diluted with water and acidified. The aqueous phase was extracted with dichloromethane. The organic phase was washed with sat. sodium chloride solution, dried over sodium sulfate and evaporated. The residue was passed through silica gel (methyl tert-butyl ether/heptane 1:5).

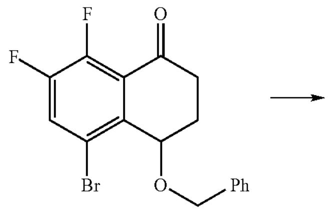

43

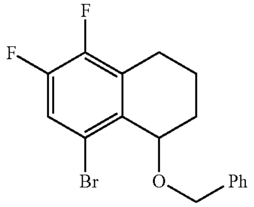

44

11.0 g (30.0 mmol) of the ketone 43 and 4.3 ml (90.0 mmol) of hydrazinium hydroxide were added to a solution of 6.7 g of potassium hydroxide in 50 ml of diethylene glycol. The batch was slowly heated to 180° C. When the evolution of nitrogen was complete and after cooling to room temperature, the batch was diluted with water and extracted a number of times with methyl tert-butyl ether. The organic phase was dried over sodium sulfate, evaporated and passed through silica gel (methyl tert-butyl ether/heptane 1:20), giving 6.4 g (60%) of the benzyl ether 44.

The alcohol 45 can be prepared from 44 analogously to the processes of Examples 7 to 9. During the preparation of the intermediate thioketal, the benzyl ether is cleaved. The protecting group must then be re-introduced in the manner already described.

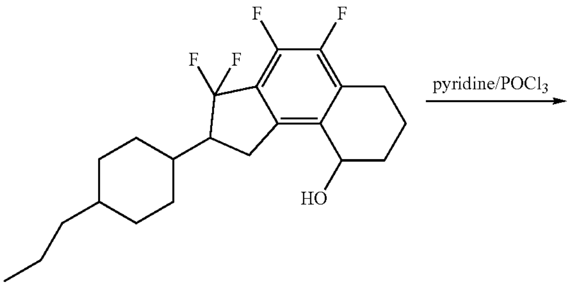

45

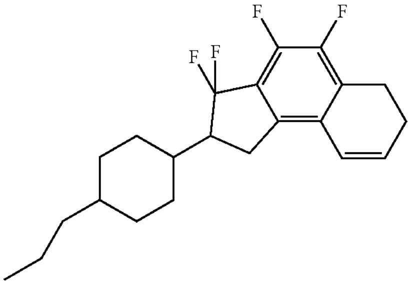

46

The synthesis of compound 46 was carried out analogously to the method indicated in Example 12.

The following compounds are prepared analogously to Examples 1 to 13. "bond" here stands for a single bond:

Examples 14-110

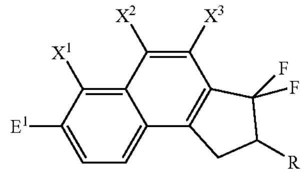

| Example | $E^1$ | $X^1$ | $X^2$ | $X^3$ | R |
|---|---|---|---|---|---|
| 14 | H | H | H | H | $CH_3$ |
| 15 | H | H | H | H | $C_2H_5$ |
| 16 | H | H | H | H | n-$C_3H_7$ |
| 17 | H | H | H | H | n-$C_4H_9$ |
| 18 | H | H | H | H | n-$C_5H_{11}$ |
| 19 | H | H | H | H | n-$C_6H_{13}$ |
| 20 | H | H | H | H | n-$C_7H_{15}$ |
| 21 | H | H | H | F | $CH_3$ |
| 22 | H | H | H | F | $C_2H_5$ |
| 23 | H | H | H | F | n-$C_3H_7$ |
| 24 | H | H | H | F | n-$C_4H_9$ |
| 25 | H | H | H | F | n-$C_5H_{11}$ |
| 26 | H | H | H | F | n-$C_6H_{13}$ |
| 27 | H | H | H | F | n-$C_7H_{15}$ |
| 28 | H | H | F | F | $CH_3$ |
| 29 | H | H | F | F | $C_2H_5$ |
| 30 | H | H | F | F | n-$C_3H_7$ |
| 31 | H | H | F | F | n-$C_4H_9$ |
| 32 | H | H | F | F | n-$C_5H_{11}$ |
| 33 | H | H | F | F | n-$C_6H_{13}$ |
| 34 | H | H | F | F | n-$C_7H_{15}$ |
| 35 | H | F | F | F | $CH_3$ |
| 36 | H | F | F | F | $C_2H_5$ |
| 37 | H | F | F | F | n-$C_4H_9$ |
| 38 | H | F | F | F | n-$C_5H_{11}$ |
| 39 | H | F | F | F | n-$C_6H_{13}$ |
| 40 | H | F | F | F | n-$C_7H_{15}$ |
| 41 | $CH_3$ | H | F | F | $CH_3$ |
| 42 | $CH_3$ | H | F | F | $C_2H_5$ |
| 43 | $CH_3$ | H | F | F | n-$C_3H_7$ |
| 44 | $CH_3$ | H | F | F | n-$C_4H_9$ |
| 45 | $CH_3$ | H | F | F | n-$C_5H_{11}$ |
| 46 | $CH_3$ | H | F | F | n-$C_6H_{13}$ |
| 47 | $CH_3$ | H | F | F | n-$C_7H_{15}$ |
| 48 | $CH_3$ | F | F | F | $CH_3$ |
| 49 | $CH_3$ | F | F | F | $C_2H_5$ |
| 50 | $CH_3$ | F | F | F | n-$C_3H_7$ |
| 51 | $CH_3$ | F | F | F | n-$C_4H_9$ |
| 52 | $CH_3$ | F | F | F | n-$C_5H_{11}$ |
| 53 | $CH_3$ | F | F | F | n-$C_6H_{13}$ |
| 54 | $CH_3$ | F | F | F | n-$C_7H_{15}$ |
| 55 | $C_2H_5$ | H | F | F | $CH_3$ |
| 56 | $C_2H_5$ | H | F | F | $C_2H_5$ |
| 57 | $C_2H_5$ | H | F | F | n-$C_3H_7$ |
| 58 | $C_2H_5$ | H | F | F | n-$C_4H_9$ |
| 59 | $C_2H_5$ | H | F | F | n-$C_5H_{11}$ |
| 60 | $C_2H_5$ | H | F | F | n-$C_6H_{13}$ |
| 61 | $C_2H_5$ | H | F | F | n-$C_7H_{15}$ |
| 62 | $C_2H_5$ | F | F | F | $CH_3$ |
| 63 | $C_2H_5$ | F | F | F | $C_2H_5$ |
| 64 | $C_2H_5$ | F | F | F | n-$C_3H_7$ |
| 65 | $C_2H_5$ | F | F | F | n-$C_4H_9$ |
| 66 | $C_2H_5$ | F | F | F | n-$C_5H_{11}$ |
| 67 | $C_2H_5$ | F | F | F | n-$C_6H_{13}$ |
| 68 | $C_2H_5$ | F | F | F | n-$C_7H_{15}$ |
| 69 | n-$C_3H_7$ | H | F | F | $CH_3$ |
| 70 | n-$C_3H_7$ | H | F | F | $C_2H_5$ |
| 71 | n-$C_3H_7$ | H | F | F | n-$C_3H_7$ |
| 72 | n-$C_3H_7$ | H | F | F | n-$C_4H_9$ |

-continued

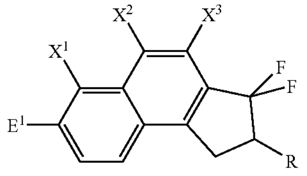

| Example | $E^1$ | $X^1$ | $X^2$ | $X^3$ | R |
|---|---|---|---|---|---|
| 73 | n-$C_3H_7$ | H | F | F | n-$C_5H_{11}$ |
| 74 | n-$C_3H_7$ | H | F | F | n-$C_6H_{13}$ |
| 75 | n-$C_3H_7$ | H | F | F | n-$C_7H_{15}$ |
| 76 | n-$C_3H_7$ | F | F | F | $CH_3$ |
| 77 | n-$C_3H_7$ | F | F | F | $C_2H_5$ |
| 78 | n-$C_3H_7$ | F | F | F | n-$C_3H_7$ |
| 79 | n-$C_3H_7$ | F | F | F | n-$C_4H_9$ |
| 80 | n-$C_3H_7$ | F | F | F | n-$C_5H_{11}$ |
| 81 | n-$C_3H_7$ | F | F | F | n-$C_6H_{13}$ |
| 82 | n-$C_3H_7$ | F | F | F | n-$C_7H_{15}$ |
| 83 | n-$C_4H_9$ | H | F | F | $CH_3$ |
| 84 | n-$C_4H_9$ | H | F | F | $C_2H_5$ |
| 85 | n-$C_4H_9$ | H | F | F | n-$C_3H_7$ |
| 86 | n-$C_4H_9$ | H | F | F | n-$C_4H_9$ |
| 87 | n-$C_4H_9$ | H | F | F | n-$C_5H_{11}$ |
| 88 | n-$C_4H_9$ | H | F | F | n-$C_6H_{13}$ |
| 89 | n-$C_4H_9$ | H | F | F | n-$C_7H_{15}$ |
| 90 | n-$C_4H_9$ | F | F | F | $CH_3$ |
| 91 | n-$C_4H_9$ | F | F | F | $C_2H_5$ |
| 92 | n-$C_4H_9$ | F | F | F | n-$C_3H_7$ |
| 93 | n-$C_4H_9$ | F | F | F | n-$C_4H_9$ |
| 94 | n-$C_4H_9$ | F | F | F | n-$C_5H_{11}$ |
| 95 | n-$C_4H_9$ | F | F | F | n-$C_6H_{13}$ |
| 96 | n-$C_4H_9$ | F | F | F | n-$C_7H_{15}$ |
| 97 | n-$C_5H_{11}$ | H | F | F | $CH_3$ |
| 98 | n-$C_5H_{11}$ | H | F | F | $C_2H_5$ |
| 99 | n-$C_5H_{11}$ | H | F | F | n-$C_3H_7$ |
| 100 | n-$C_5H_{11}$ | H | F | F | n-$C_4H_9$ |
| 101 | n-$C_5H_{11}$ | H | F | F | n-$C_5H_{11}$ |
| 102 | n-$C_5H_{11}$ | H | F | F | n-$C_6H_{13}$ |
| 103 | n-$C_5H_{11}$ | H | F | F | n-$C_7H_{15}$ |
| 104 | n-$C_5H_{11}$ | F | F | F | $CH_3$ |
| 105 | n-$C_5H_{11}$ | F | F | F | $C_2H_5$ |
| 106 | n-$C_5H_{11}$ | F | F | F | n-$C_3H_7$ |
| 107 | n-$C_5H_{11}$ | F | F | F | n-$C_4H_9$ |
| 108 | n-$C_5H_{11}$ | F | F | F | n-$C_5H_{11}$ |
| 109 | n-$C_5H_{11}$ | F | F | F | n-$C_6H_{13}$ |
| 110 | n-$C_5H_{11}$ | F | F | F | n-$C_7H_{15}$ |

Examples 111-228

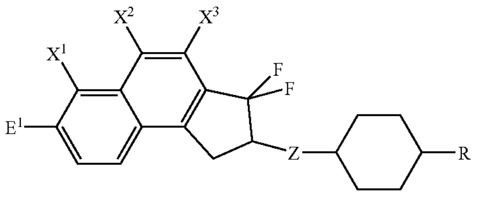

| Example | $E^1$ | $X^1$ | $X^2$ | $X^3$ | Z | R |
|---|---|---|---|---|---|---|
| 111 | H | H | H | F | Bond | $CH_3$ |
| 112 | H | H | H | F | Bond | $C_2H_5$ |
| 113 | H | H | H | F | Bond | n-$C_4H_9$ |
| 114 | H | H | H | F | Bond | n-$C_5H_{11}$ |
| 115 | H | H | H | F | Bond | n-$C_6H_{13}$ |
| 116 | H | H | H | F | Bond | n-$C_7H_{15}$ |
| 117 | H | H | F | F | Bond | $CH_3$ |
| 118 | H | H | F | F | Bond | $C_2H_5$ |
| 119 | H | H | F | F | Bond | n-$C_3H_7$ |

-continued

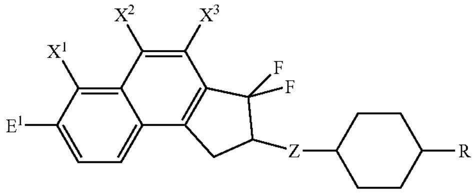

| Example | $E^1$ | $X^1$ | $X^2$ | $X^3$ | Z | R |
|---|---|---|---|---|---|---|
| 120 | H | H | F | F | Bond | n-$C_4H_9$ |
| 121 | H | H | F | F | Bond | n-$C_5H_{11}$ |
| 122 | H | H | F | F | Bond | n-$C_6H_{13}$ |
| 123 | H | H | F | F | Bond | n-$C_7H_{15}$ |
| 124 | H | F | F | F | Bond | $CH_3$ |
| 125 | H | F | F | F | Bond | $C_2H_5$ |
| 126 | H | F | F | F | Bond | n-$C_3H_7$ |
| 127 | H | F | F | F | Bond | n-$C_4H_9$ |
| 128 | H | F | F | F | Bond | n-$C_5H_{11}$ |
| 129 | H | F | F | F | Bond | n-$C_6H_{13}$ |
| 130 | H | F | F | F | Bond | n-$C_7H_{15}$ |
| 131 | H | F | F | F | $CF_2CF_2$ | $CH_3$ |
| 132 | H | F | F | F | $CF_2CF_2$ | $C_2H_5$ |
| 133 | H | F | F | F | $CF_2CF_2$ | n-$C_3H_7$ |
| 134 | H | F | F | F | $CF_2CF_2$ | n-$C_4H_9$ |
| 135 | H | F | F | F | $CF_2CF_2$ | n-$C_5H_{11}$ |
| 136 | H | F | F | F | $CF_2CF_2$ | n-$C_6H_{13}$ |
| 137 | H | F | F | F | $CF_2CF_2$ | n-$C_7H_{15}$ |
| 138 | H | F | F | F | $OCF_2$ | $CH_3$ |
| 139 | H | F | F | F | $OCF_2$ | $C_2H_5$ |
| 140 | H | F | F | F | $OCF_2$ | n-$C_3H_7$ |
| 141 | H | F | F | F | $OCF_2$ | n-$C_4H_9$ |
| 142 | H | F | F | F | $OCF_2$ | n-$C_5H_{11}$ |
| 143 | H | F | F | F | $OCF_2$ | n-$C_6H_{13}$ |
| 144 | H | F | F | F | $OCF_2$ | n-$C_7H_{15}$ |
| 145 | $CH_3$ | H | F | F | Bond | $CH_3$ |
| 146 | $CH_3$ | H | F | F | Bond | $C_2H_5$ |
| 147 | $CH_3$ | H | F | F | Bond | n-$C_3H_7$ |
| 148 | $CH_3$ | H | F | F | Bond | n-$C_4H_9$ |
| 149 | $CH_3$ | H | F | F | Bond | n-$C_5H_{11}$ |
| 150 | $CH_3$ | H | F | F | Bond | n-$C_6H_{13}$ |
| 151 | $CH_3$ | H | F | F | Bond | n-$C_7H_{15}$ |
| 152 | $CH_3$ | F | F | F | Bond | $CH_3$ |
| 153 | $CH_3$ | F | F | F | Bond | $C_2H_5$ |
| 154 | $CH_3$ | F | F | F | Bond | n-$C_3H_7$ |
| 155 | $CH_3$ | F | F | F | Bond | n-$C_4H_9$ |
| 156 | $CH_3$ | F | F | F | Bond | n-$C_5H_{11}$ |
| 157 | $CH_3$ | F | F | F | Bond | n-$C_6H_{13}$ |
| 158 | $CH_3$ | F | F | F | Bond | n-$C_7H_{15}$ |
| 159 | $CH_3$ | F | F | F | $CF_2CF_2$ | $CH_3$ |
| 160 | $CH_3$ | F | F | F | $CF_2CF_2$ | $C_2H_5$ |
| 161 | $CH_3$ | F | F | F | $CF_2CF_2$ | n-$C_3H_7$ |
| 162 | $CH_3$ | F | F | F | $CF_2CF_2$ | n-$C_4H_9$ |
| 163 | $CH_3$ | F | F | F | $CF_2CF_2$ | n-$C_5H_{11}$ |
| 164 | $CH_3$ | F | F | F | $CF_2CF_2$ | n-$C_6H_{13}$ |
| 165 | $CH_3$ | F | F | F | $CF_2CF_2$ | n-$C_7H_{15}$ |
| 166 | $CH_3$ | F | F | F | $OCF_2$ | $CH_3$ |
| 167 | $CH_3$ | F | F | F | $OCF_2$ | $C_2H_5$ |
| 168 | $CH_3$ | F | F | F | $OCF_2$ | n-$C_3H_7$ |
| 169 | $CH_3$ | F | F | F | $OCF_2$ | n-$C_4H_9$ |
| 170 | $CH_3$ | F | F | F | $OCF_2$ | n-$C_5H_{11}$ |
| 171 | $CH_3$ | F | F | F | $OCF_2$ | n-$C_6H_{13}$ |
| 172 | $CH_3$ | F | F | F | $OCF_2$ | n-$C_7H_{15}$ |
| 173 | $C_2H_5$ | H | F | F | Bond | $CH_3$ |
| 174 | $C_2H_5$ | H | F | F | Bond | $C_2H_5$ |
| 175 | $C_2H_5$ | H | F | F | Bond | n-$C_3H_7$ |
| 176 | $C_2H_5$ | H | F | F | Bond | n-$C_4H_9$ |
| 177 | $C_2H_5$ | H | F | F | Bond | n-$C_5H_{11}$ |
| 178 | $C_2H_5$ | H | F | F | Bond | n-$C_6H_{13}$ |
| 179 | $C_2H_5$ | H | F | F | Bond | n-$C_7H_{15}$ |
| 180 | $C_2H_5$ | F | F | F | Bond | $CH_3$ |
| 181 | $C_2H_5$ | F | F | F | Bond | $C_2H_5$ |
| 182 | $C_2H_5$ | F | F | F | Bond | n-$C_3H_7$ |
| 183 | $C_2H_5$ | F | F | F | Bond | n-$C_4H_9$ |
| 184 | $C_2H_5$ | F | F | F | Bond | n-$C_5H_{11}$ |
| 185 | $C_2H_5$ | F | F | F | Bond | n-$C_6H_{13}$ |
| 186 | $C_2H_5$ | F | F | F | Bond | n-$C_7H_{15}$ |

-continued

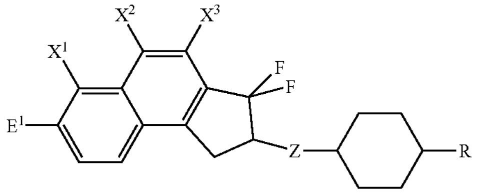

| Example | $E^1$ | $X^1$ | $X^2$ | $X^3$ | Z | R |
|---|---|---|---|---|---|---|
| 187 | $n-C_3H_7$ | H | F | F | Bond | $CH_3$ |
| 188 | $n-C_3H_7$ | H | F | F | Bond | $C_2H_5$ |
| 189 | $n-C_3H_7$ | H | F | F | Bond | $n-C_3H_7$ |
| 190 | $n-C_3H_7$ | H | F | F | Bond | $n-C_4H_9$ |
| 191 | $n-C_3H_7$ | H | F | F | Bond | $n-C_5H_{11}$ |
| 192 | $n-C_3H_7$ | H | F | F | Bond | $n-C_6H_{13}$ |
| 193 | $n-C_3H_7$ | H | F | F | Bond | $n-C_7H_{15}$ |
| 194 | $n-C_3H_7$ | F | F | F | Bond | $CH_3$ |
| 195 | $n-C_3H_7$ | F | F | F | Bond | $C_2H_5$ |
| 196 | $n-C_3H_7$ | F | F | F | Bond | $n-C_3H_7$ |
| 197 | $n-C_3H_7$ | F | F | F | Bond | $n-C_4H_9$ |
| 198 | $n-C_3H_7$ | F | F | F | Bond | $n-C_5H_{11}$ |
| 199 | $n-C_3H_7$ | F | F | F | Bond | $n-C_6H_{13}$ |
| 200 | $n-C_3H_7$ | F | F | F | Bond | $n-C_7H_{15}$ |
| 201 | $n-C_4H_9$ | H | F | F | Bond | $CH_3$ |
| 202 | $n-C_4H_9$ | H | F | F | Bond | $C_2H_5$ |
| 203 | $n-C_4H_9$ | H | F | F | Bond | $n-C_3H_7$ |
| 204 | $n-C_4H_9$ | H | F | F | Bond | $n-C_4H_9$ |
| 205 | $n-C_4H_9$ | H | F | F | Bond | $n-C_5H_{11}$ |
| 206 | $n-C_4H_9$ | H | F | F | Bond | $n-C_6H_{13}$ |
| 207 | $n-C_4H_9$ | H | F | F | Bond | $n-C_7H_{15}$ |
| 208 | $n-C_4H_9$ | F | F | F | Bond | $CH_3$ |
| 209 | $n-C_4H_9$ | F | F | F | Bond | $C_2H_5$ |
| 210 | $n-C_4H_9$ | F | F | F | Bond | $n-C_3H_7$ |
| 211 | $n-C_4H_9$ | F | F | F | Bond | $n-C_4H_9$ |
| 212 | $n-C_4H_9$ | F | F | F | Bond | $n-C_5H_{11}$ |
| 213 | $n-C_4H_9$ | F | F | F | Bond | $n-C_6H_{13}$ |
| 214 | $n-C_4H_9$ | F | F | F | Bond | $n-C_7H_{15}$ |
| 215 | $n-C_5H_{11}$ | H | F | F | Bond | $CH_3$ |
| 216 | $n-C_5H_{11}$ | H | F | F | Bond | $C_2H_5$ |
| 217 | $n-C_5H_{11}$ | H | F | F | Bond | $n-C_3H_7$ |
| 218 | $n-C_5H_{11}$ | H | F | F | Bond | $n-C_4H_9$ |
| 219 | $n-C_5H_{11}$ | H | F | F | Bond | $n-C_5H_{11}$ |
| 220 | $n-C_5H_{11}$ | H | F | F | Bond | $n-C_6H_{13}$ |
| 221 | $n-C_5H_{11}$ | H | F | F | Bond | $n-C_7H_{15}$ |
| 222 | $n-C_5H_{11}$ | F | F | F | Bond | $CH_3$ |
| 223 | $n-C_5H_{11}$ | F | F | F | Bond | $C_2H_5$ |
| 224 | $n-C_5H_{11}$ | F | F | F | Bond | $n-C_3H_7$ |
| 225 | $n-C_5H_{11}$ | F | F | F | Bond | $n-C_4H_9$ |
| 226 | $n-C_5H_{11}$ | F | F | F | Bond | $n-C_5H_{11}$ |
| 227 | $n-C_5H_{11}$ | F | F | F | Bond | $n-C_6H_{13}$ |
| 228 | $n-C_5H_{11}$ | F | F | F | Bond | $n-C_7H_{15}$ |

Examples 229-347

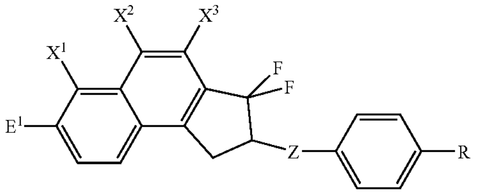

| Example | $E^1$ | $X^1$ | $X^2$ | $X^3$ | Z | R |
|---|---|---|---|---|---|---|
| 229 | H | H | H | F | Bond | $CH_3$ |
| 230 | H | H | H | F | Bond | $C_2H_5$ |
| 231 | H | H | H | F | Bond | $n-C_3H_7$ |
| 232 | H | H | H | F | Bond | $n-C_4H_9$ |

-continued

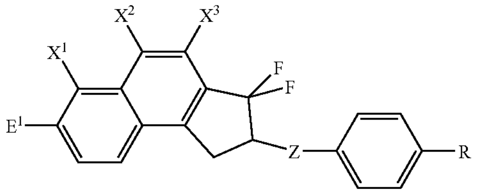

| Example | $E^1$ | $X^1$ | $X^2$ | $X^3$ | Z | R |
|---|---|---|---|---|---|---|
| 233 | H | H | H | F | Bond | $n-C_5H_{11}$ |
| 234 | H | H | H | F | Bond | $n-C_6H_{13}$ |
| 235 | H | H | H | F | Bond | $n-C_7H_{15}$ |
| 236 | H | H | F | F | Bond | $CH_3$ |
| 237 | H | H | F | F | Bond | $C_2H_5$ |
| 238 | H | H | F | F | Bond | $n-C_3H_7$ |
| 239 | H | H | F | F | Bond | $n-C_4H_9$ |
| 240 | H | H | F | F | Bond | $n-C_5H_{11}$ |
| 241 | H | H | F | F | Bond | $n-C_6H_{13}$ |
| 242 | H | H | F | F | Bond | $n-C_7H_{15}$ |
| 243 | H | F | F | F | Bond | $CH_3$ |
| 244 | H | F | F | F | Bond | $C_2H_5$ |
| 245 | H | F | F | F | Bond | $n-C_3H_7$ |
| 246 | H | F | F | F | Bond | $n-C_4H_9$ |
| 247 | H | F | F | F | Bond | $n-C_5H_{11}$ |
| 248 | H | F | F | F | Bond | $n-C_6H_{13}$ |
| 249 | H | F | F | F | Bond | $n-C_7H_{15}$ |
| 250 | H | F | F | F | $CF_2CF_2$ | $CH_3$ |
| 251 | H | F | F | F | $CF_2CF_2$ | $C_2H_5$ |
| 252 | H | F | F | F | $CF_2CF_2$ | $n-C_3H_7$ |
| 253 | H | F | F | F | $CF_2CF_2$ | $n-C_4H_9$ |
| 254 | H | F | F | F | $CF_2CF_2$ | $n-C_5H_{11}$ |
| 255 | H | F | F | F | $CF_2CF_2$ | $n-C_6H_{13}$ |
| 256 | H | F | F | F | $CF_2CF_2$ | $n-C_7H_{15}$ |
| 257 | H | F | F | F | $CF_2O$ | $CH_3$ |
| 258 | H | F | F | F | $CF_2O$ | $C_2H_5$ |
| 259 | H | F | F | F | $CF_2O$ | $n-C_3H_7$ |
| 260 | H | F | F | F | $CF_2O$ | $n-C_4H_9$ |
| 261 | H | F | F | F | $CF_2O$ | $n-C_5H_{11}$ |
| 262 | H | F | F | F | $CF_2O$ | $n-C_6H_{13}$ |
| 263 | H | F | F | F | $CF_2O$ | $n-C_7H_{15}$ |
| 264 | $CH_3$ | H | F | F | Bond | $CH_3$ |
| 265 | $CH_3$ | H | F | F | Bond | $C_2H_5$ |
| 266 | $CH_3$ | H | F | F | Bond | $n-C_3H_7$ |
| 267 | $CH_3$ | H | F | F | Bond | $n-C_4H_9$ |
| 268 | $CH_3$ | H | F | F | Bond | $n-C_5H_{11}$ |
| 269 | $CH_3$ | H | F | F | Bond | $n-C_6H_{13}$ |
| 270 | $CH_3$ | H | F | F | Bond | $n-C_7H_{15}$ |
| 271 | $CH_3$ | F | F | F | Bond | $CH_3$ |
| 272 | $CH_3$ | F | F | F | Bond | $C_2H_5$ |
| 273 | $CH_3$ | F | F | F | Bond | $n-C_3H_7$ |
| 274 | $CH_3$ | F | F | F | Bond | $n-C_4H_9$ |
| 275 | $CH_3$ | F | F | F | Bond | $n-C_5H_{11}$ |
| 276 | $CH_3$ | F | F | F | Bond | $n-C_6H_{13}$ |
| 277 | $CH_3$ | F | F | F | Bond | $n-C_7H_{15}$ |
| 278 | $CH_3$ | F | F | F | $CF_2CF_2$ | $CH_3$ |
| 279 | $CH_3$ | F | F | F | $CF_2CF_2$ | $C_2H_5$ |
| 280 | $CH_3$ | F | F | F | $CF_2CF_2$ | $n-C_3H_7$ |
| 281 | $CH_3$ | F | F | F | $CF_2CF_2$ | $n-C_4H_9$ |
| 282 | $CH_3$ | F | F | F | $CF_2CF_2$ | $n-C_5H_{11}$ |
| 283 | $CH_3$ | F | F | F | $CF_2CF_2$ | $n-C_6H_{13}$ |
| 284 | $CH_3$ | F | F | F | $CF_2CF_2$ | $n-C_7H_{15}$ |
| 285 | $CH_3$ | F | F | F | $CF_2O$ | $CH_3$ |
| 286 | $CH_3$ | F | F | F | $CF_2O$ | $C_2H_5$ |
| 287 | $CH_3$ | F | F | F | $CF_2O$ | $n-C_3H_7$ |
| 288 | $CH_3$ | F | F | F | $CF_2O$ | $n-C_4H_9$ |
| 289 | $CH_3$ | F | F | F | $CF_2O$ | $n-C_5H_{11}$ |
| 290 | $CH_3$ | F | F | F | $CF_2O$ | $n-C_6H_{13}$ |
| 291 | $CH_3$ | F | F | F | $CF_2O$ | $n-C_7H_{15}$ |
| 292 | $C_2H_5$ | H | F | F | Bond | $CH_3$ |
| 293 | $C_2H_5$ | H | F | F | Bond | $C_2H_5$ |
| 294 | $C_2H_5$ | H | F | F | Bond | $n-C_3H_7$ |
| 295 | $C_2H_5$ | H | F | F | Bond | $n-C_4H_9$ |
| 296 | $C_2H_5$ | H | F | F | Bond | $n-C_5H_{11}$ |
| 297 | $C_2H_5$ | H | F | F | Bond | $n-C_6H_{13}$ |
| 298 | $C_2H_5$ | H | F | F | Bond | $n-C_7H_{15}$ |
| 299 | $C_2H_5$ | F | F | F | Bond | $CH_3$ |

-continued

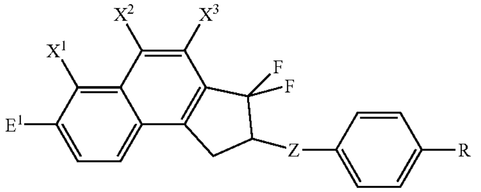

| Example | $E^1$ | $X^1$ | $X^2$ | $X^3$ | Z | R |
|---|---|---|---|---|---|---|
| 300 | $C_2H_5$ | F | F | F | Bond | $C_2H_5$ |
| 301 | $C_2H_5$ | F | F | F | Bond | n-$C_3H_7$ |
| 302 | $C_2H_5$ | F | F | F | Bond | n-$C_4H_9$ |
| 303 | $C_2H_5$ | F | F | F | Bond | n-$C_5H_{11}$ |
| 304 | $C_2H_5$ | F | F | F | Bond | n-$C_6H_{13}$ |
| 305 | $C_2H_5$ | F | F | F | Bond | n-$C_7H_{15}$ |
| 306 | n-$C_3H_7$ | H | F | F | Bond | $CH_3$ |
| 307 | n-$C_3H_7$ | H | F | F | Bond | $C_2H_5$ |
| 308 | n-$C_3H_7$ | H | F | F | Bond | n-$C_3H_7$ |
| 309 | n-$C_3H_7$ | H | F | F | Bond | n-$C_4H_9$ |
| 310 | n-$C_3H_7$ | H | F | F | Bond | n-$C_5H_{11}$ |
| 311 | n-$C_3H_7$ | H | F | F | Bond | n-$C_6H_{13}$ |
| 312 | n-$C_3H_7$ | H | F | F | Bond | n-$C_7H_{15}$ |
| 313 | n-$C_3H_7$ | F | F | F | Bond | $CH_3$ |
| 314 | n-$C_3H_7$ | F | F | F | Bond | $C_2H_5$ |
| 315 | n-$C_3H_7$ | F | F | F | Bond | n-$C_3H_7$ |
| 316 | n-$C_3H_7$ | F | F | F | Bond | n-$C_4H_9$ |
| 317 | n-$C_3H_7$ | F | F | F | Bond | n-$C_5H_{11}$ |
| 318 | n-$C_3H_7$ | F | F | F | Bond | n-$C_6H_{13}$ |
| 319 | n-$C_3H_7$ | F | F | F | Bond | n-$C_7H_{15}$ |
| 320 | n-$C_4H_9$ | H | F | F | Bond | $CH_3$ |
| 321 | n-$C_4H_9$ | H | F | F | Bond | $C_2H_5$ |
| 322 | n-$C_4H_9$ | H | F | F | Bond | n-$C_3H_7$ |
| 323 | n-$C_4H_9$ | H | F | F | Bond | n-$C_4H_9$ |
| 324 | n-$C_4H_9$ | H | F | F | Bond | n-$C_5H_{11}$ |
| 325 | n-$C_4H_9$ | H | F | F | Bond | n-$C_6H_{13}$ |
| 326 | n-$C_4H_9$ | H | F | F | Bond | n-$C_7H_{15}$ |
| 327 | n-$C_4H_9$ | F | F | F | Bond | $CH_3$ |
| 328 | n-$C_4H_9$ | F | F | F | Bond | $C_2H_5$ |
| 329 | n-$C_4H_9$ | F | F | F | Bond | n-$C_3H_7$ |
| 330 | n-$C_4H_9$ | F | F | F | Bond | n-$C_4H_9$ |
| 331 | n-$C_4H_9$ | F | F | F | Bond | n-$C_5H_{11}$ |
| 332 | n-$C_4H_9$ | F | F | F | Bond | n-$C_6H_{13}$ |
| 333 | n-$C_4H_9$ | F | F | F | Bond | n-$C_7H_{15}$ |
| 334 | n-$C_5H_{11}$ | H | F | F | Bond | $CH_3$ |
| 335 | n-$C_5H_{11}$ | H | F | F | Bond | $C_2H_5$ |
| 336 | n-$C_5H_{11}$ | H | F | F | Bond | n-$C_3H_7$ |
| 337 | n-$C_5H_{11}$ | H | F | F | Bond | n-$C_4H_9$ |
| 338 | n-$C_5H_{11}$ | H | F | F | Bond | n-$C_5H_{11}$ |
| 339 | n-$C_5H_{11}$ | H | F | F | Bond | n-$C_6H_{13}$ |
| 340 | n-$C_5H_{11}$ | H | F | F | Bond | n-$C_7H_{15}$ |
| 341 | n-$C_5H_{11}$ | F | F | F | Bond | $CH_3$ |
| 342 | n-$C_5H_{11}$ | F | F | F | Bond | $C_2H_5$ |
| 343 | n-$C_5H_{11}$ | F | F | F | Bond | n-$C_3H_7$ |
| 344 | n-$C_5H_{11}$ | F | F | F | Bond | n-$C_4H_9$ |
| 345 | n-$C_5H_{11}$ | F | F | F | Bond | n-$C_5H_{11}$ |
| 346 | n-$C_5H_{11}$ | F | F | F | Bond | n-$C_6H_{13}$ |
| 347 | n-$C_5H_{11}$ | F | F | F | Bond | n-$C_7H_{15}$ |

Examples 348-466

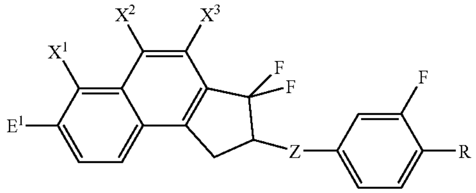

| Example | $E^1$ | $X^1$ | $X^2$ | $X^3$ | Z | R |
|---|---|---|---|---|---|---|
| 348 | H | H | H | F | Bond | $CH_3$ |
| 349 | H | H | H | F | Bond | $C_2H_5$ |
| 350 | H | H | H | F | Bond | n-$C_3H_7$ |
| 351 | H | H | H | F | Bond | n-$C_4H_9$ |
| 352 | H | H | H | F | Bond | n-$C_5H_{11}$ |
| 353 | H | H | H | F | Bond | n-$C_6H_{13}$ |
| 354 | H | H | H | F | Bond | n-$C_7H_{15}$ |
| 355 | H | H | F | F | Bond | $CH_3$ |
| 356 | H | H | F | F | Bond | $C_2H_5$ |
| 357 | H | H | F | F | Bond | n-$C_3H_7$ |
| 358 | H | H | F | F | Bond | n-$C_4H_9$ |
| 359 | H | H | F | F | Bond | n-$C_5H_{11}$ |
| 360 | H | H | F | F | Bond | n-$C_6H_{13}$ |
| 361 | H | H | F | F | Bond | n-$C_7H_{15}$ |
| 362 | H | F | F | F | Bond | $CH_3$ |
| 363 | H | F | F | F | Bond | $C_2H_5$ |
| 364 | H | F | F | F | Bond | n-$C_3H_7$ |
| 365 | H | F | F | F | Bond | n-$C_4H_9$ |
| 366 | H | F | F | F | Bond | n-$C_5H_{11}$ |
| 367 | H | F | F | F | Bond | n-$C_6H_{13}$ |
| 368 | H | F | F | F | Bond | n-$C_7H_{15}$ |
| 369 | H | F | F | F | $CF_2CF_2$ | $CH_3$ |
| 370 | H | F | F | F | $CF_2CF_2$ | $C_2H_5$ |
| 371 | H | F | F | F | $CF_2CF_2$ | n-$C_3H_7$ |
| 372 | H | F | F | F | $CF_2CF_2$ | n-$C_4H_9$ |
| 373 | H | F | F | F | $CF_2CF_2$ | n-$C_5H_{11}$ |
| 374 | H | F | F | F | $CF_2CF_2$ | n-$C_6H_{13}$ |
| 375 | H | F | F | F | $CF_2CF_2$ | n-$C_7H_{15}$ |
| 376 | H | F | F | F | $CF_2O$ | $CH_3$ |
| 377 | H | F | F | F | $CF_2O$ | $C_2H_5$ |
| 378 | H | F | F | F | $CF_2O$ | n-$C_3H_7$ |
| 379 | H | F | F | F | $CF_2O$ | n-$C_4H_9$ |
| 380 | H | F | F | F | $CF_2O$ | n-$C_5H_{11}$ |
| 381 | H | F | F | F | $CF_2O$ | n-$C_6H_{13}$ |
| 382 | H | F | F | F | $CF_2O$ | n-$C_7H_{15}$ |
| 383 | $CH_3$ | H | F | F | Bond | $CH_3$ |
| 384 | $CH_3$ | H | F | F | Bond | $C_2H_5$ |
| 385 | $CH_3$ | H | F | F | Bond | n-$C_3H_7$ |
| 386 | $CH_3$ | H | F | F | Bond | n-$C_4H_9$ |
| 387 | $CH_3$ | H | F | F | Bond | n-$C_5H_{11}$ |
| 388 | $CH_3$ | H | F | F | Bond | n-$C_6H_{13}$ |
| 389 | $CH_3$ | H | F | F | Bond | n-$C_7H_{15}$ |
| 390 | $CH_3$ | F | F | F | Bond | $CH_3$ |
| 391 | $CH_3$ | F | F | F | Bond | $C_2H_5$ |
| 392 | $CH_3$ | F | F | F | Bond | n-$C_3H_7$ |
| 393 | $CH_3$ | F | F | F | Bond | n-$C_4H_9$ |
| 394 | $CH_3$ | F | F | F | Bond | n-$C_5H_{11}$ |
| 395 | $CH_3$ | F | F | F | Bond | n-$C_6H_{13}$ |
| 396 | $CH_3$ | F | F | F | Bond | n-$C_7H_{15}$ |
| 397 | $CH_3$ | F | F | F | $CF_2CF_2$ | $CH_3$ |
| 398 | $CH_3$ | F | F | F | $CF_2CF_2$ | $C_2H_5$ |
| 399 | $CH_3$ | F | F | F | $CF_2CF_2$ | n-$C_3H_7$ |
| 400 | $CH_3$ | F | F | F | $CF_2CF_2$ | n-$C_4H_9$ |
| 401 | $CH_3$ | F | F | F | $CF_2CF_2$ | n-$C_5H_{11}$ |
| 402 | $CH_3$ | F | F | F | $CF_2CF_2$ | n-$C_6H_{13}$ |
| 403 | $CH_3$ | F | F | F | $CF_2CF_2$ | n-$C_7H_{15}$ |
| 404 | $CH_3$ | F | F | F | $CF_2O$ | $CH_3$ |
| 405 | $CH_3$ | F | F | F | $CF_2O$ | $C_2H_5$ |
| 406 | $CH_3$ | F | F | F | $CF_2O$ | n-$C_3H_7$ |
| 407 | $CH_3$ | F | F | F | $CF_2O$ | n-$C_4H_9$ |
| 408 | $CH_3$ | F | F | F | $CF_2O$ | n-$C_5H_{11}$ |
| 409 | $CH_3$ | F | F | F | $CF_2O$ | n-$C_6H_{13}$ |
| 410 | $CH_3$ | F | F | F | $CF_2O$ | n-$C_7H_{15}$ |
| 411 | $C_2H_5$ | H | F | F | Bond | $CH_3$ |

-continued

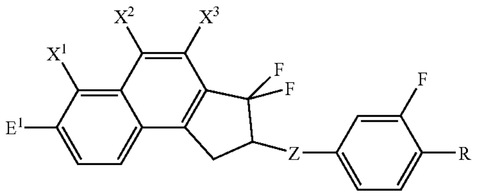

| Example | $E^1$ | $X^1$ | $X^2$ | $X^3$ | Z | R |
|---|---|---|---|---|---|---|
| 412 | $C_2H_5$ | H | F | F | Bond | $C_2H_5$ |
| 413 | $C_2H_5$ | H | F | F | Bond | n-$C_3H_7$ |
| 414 | $C_2H_5$ | H | F | F | Bond | n-$C_4H_9$ |
| 415 | $C_2H_5$ | H | F | F | Bond | n-$C_5H_{11}$ |
| 416 | $C_2H_5$ | H | F | F | Bond | n-$C_6H_{13}$ |
| 417 | $C_2H_5$ | H | F | F | Bond | n-$C_7H_{15}$ |
| 418 | $C_2H_5$ | F | F | F | Bond | $CH_3$ |
| 419 | $C_2H_5$ | F | F | F | Bond | $C_2H_5$ |
| 420 | $C_2H_5$ | F | F | F | Bond | n-$C_3H_7$ |
| 421 | $C_2H_5$ | F | F | F | Bond | n-$C_4H_9$ |
| 422 | $C_2H_5$ | F | F | F | Bond | n-$C_5H_{11}$ |
| 423 | $C_2H_5$ | F | F | F | Bond | n-$C_6H_{13}$ |
| 424 | $C_2H_5$ | F | F | F | Bond | n-$C_7H_{15}$ |
| 425 | n-$C_3H_7$ | H | F | F | Bond | $CH_3$ |
| 426 | n-$C_3H_7$ | H | F | F | Bond | $C_2H_5$ |
| 427 | n-$C_3H_7$ | H | F | F | Bond | n-$C_3H_7$ |
| 428 | n-$C_3H_7$ | H | F | F | Bond | n-$C_4H_9$ |
| 429 | n-$C_3H_7$ | H | F | F | Bond | n-$C_5H_{11}$ |
| 430 | n-$C_3H_7$ | H | F | F | Bond | n-$C_6H_{13}$ |
| 431 | n-$C_3H_7$ | H | F | F | Bond | n-$C_7H_{15}$ |
| 432 | n-$C_3H_7$ | F | F | F | Bond | $CH_3$ |
| 433 | n-$C_3H_7$ | F | F | F | Bond | $C_2H_5$ |
| 434 | n-$C_3H_7$ | F | F | F | Bond | n-$C_3H_7$ |
| 435 | n-$C_3H_7$ | F | F | F | Bond | n-$C_4H_9$ |
| 436 | n-$C_3H_7$ | F | F | F | Bond | n-$C_5H_{11}$ |
| 437 | n-$C_3H_7$ | F | F | F | Bond | n-$C_6H_{13}$ |
| 438 | n-$C_3H_7$ | F | F | F | Bond | n-$C_7H_{15}$ |
| 439 | n-$C_4H_9$ | H | F | F | Bond | $CH_3$ |
| 440 | n-$C_4H_9$ | H | F | F | Bond | $C_2H_5$ |
| 441 | n-$C_4H_9$ | H | F | F | Bond | n-$C_3H_7$ |
| 442 | n-$C_4H_9$ | H | F | F | Bond | n-$C_4H_9$ |
| 443 | n-$C_4H_9$ | H | F | F | Bond | n-$C_5H_{11}$ |
| 444 | n-$C_4H_9$ | H | F | F | Bond | n-$C_6H_{13}$ |
| 445 | n-$C_4H_9$ | H | F | F | Bond | n-$C_7H_{15}$ |
| 446 | n-$C_4H_9$ | F | F | F | Bond | $CH_3$ |
| 447 | n-$C_4H_9$ | F | F | F | Bond | $C_2H_5$ |
| 448 | n-$C_4H_9$ | F | F | F | Bond | n-$C_3H_7$ |
| 449 | n-$C_4H_9$ | F | F | F | Bond | n-$C_4H_9$ |
| 450 | n-$C_4H_9$ | F | F | F | Bond | n-$C_5H_{11}$ |
| 451 | n-$C_4H_9$ | F | F | F | Bond | n-$C_6H_{13}$ |
| 452 | n-$C_4H_9$ | F | F | F | Bond | n-$C_7H_{15}$ |
| 453 | n-$C_5H_{11}$ | H | F | F | Bond | $CH_3$ |
| 454 | n-$C_5H_{11}$ | H | F | F | Bond | $C_2H_5$ |
| 455 | n-$C_5H_{11}$ | H | F | F | Bond | n-$C_3H_7$ |
| 456 | n-$C_5H_{11}$ | H | F | F | Bond | n-$C_4H_9$ |
| 457 | n-$C_5H_{11}$ | H | F | F | Bond | n-$C_5H_{11}$ |
| 458 | n-$C_5H_{11}$ | H | F | F | Bond | n-$C_6H_{13}$ |
| 459 | n-$C_5H_{11}$ | H | F | F | Bond | n-$C_7H_{15}$ |
| 460 | n-$C_5H_{11}$ | F | F | F | Bond | $CH_3$ |
| 461 | n-$C_5H_{11}$ | F | F | F | Bond | $C_2H_5$ |
| 462 | n-$C_5H_{11}$ | F | F | F | Bond | n-$C_3H_7$ |
| 463 | n-$C_5H_{11}$ | F | F | F | Bond | n-$C_4H_9$ |
| 464 | n-$C_5H_{11}$ | F | F | F | Bond | n-$C_5H_{11}$ |
| 465 | n-$C_5H_{11}$ | F | F | F | Bond | n-$C_6H_{13}$ |
| 466 | n-$C_5H_{11}$ | F | F | F | Bond | n-$C_7H_{15}$ |

Examples 467-549

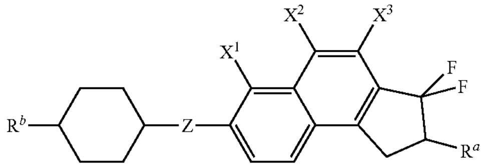

| Example | $R^b$ | $X^1$ | $X^2$ | $X^3$ | Z | $R^a$ |
|---|---|---|---|---|---|---|
| 467 | $CH_3$ | H | F | F | Bond | $CH_3$ |
| 468 | $CH_3$ | H | F | F | Bond | $C_2H_5$ |
| 469 | $CH_3$ | H | F | F | Bond | n-$C_3H_7$ |
| 470 | $CH_3$ | H | F | F | Bond | n-$C_4H_9$ |
| 471 | $CH_3$ | H | F | F | Bond | n-$C_5H_{11}$ |
| 472 | $CH_3$ | H | F | F | Bond | n-$C_6H_{13}$ |
| 473 | $CH_3$ | H | F | F | Bond | n-$C_7H_{15}$ |
| 474 | $CH_3$ | F | F | F | Bond | $CH_3$ |
| 475 | $CH_3$ | F | F | F | Bond | $C_2H_5$ |
| 476 | $CH_3$ | F | F | F | Bond | n-$C_3H_7$ |
| 477 | $CH_3$ | F | F | F | Bond | n-$C_4H_9$ |
| 478 | $CH_3$ | F | F | F | Bond | n-$C_5H_{11}$ |
| 479 | $CH_3$ | F | F | F | Bond | n-$C_6H_{13}$ |
| 480 | $CH_3$ | F | F | F | Bond | n-$C_7H_{15}$ |
| 481 | $CH_3$ | F | F | F | $CF_2CF_2$ | $CH_3$ |
| 482 | $CH_3$ | F | F | F | $CF_2CF_2$ | $C_2H_5$ |
| 483 | $CH_3$ | F | F | F | $CF_2CF_2$ | n-$C_3H_7$ |
| 484 | $CH_3$ | F | F | F | $CF_2CF_2$ | n-$C_4H_9$ |
| 485 | $CH_3$ | F | F | F | $CF_2CF_2$ | n-$C_5H_{11}$ |
| 486 | $CH_3$ | F | F | F | $CF_2CF_2$ | n-$C_6H_{13}$ |
| 487 | $CH_3$ | F | F | F | $CF_2CF_2$ | n-$C_7H_{15}$ |
| 488 | $C_2H_5$ | H | F | F | Bond | $CH_3$ |
| 489 | $C_2H_5$ | H | F | F | Bond | $C_2H_5$ |
| 490 | $C_2H_5$ | H | F | F | Bond | n-$C_3H_7$ |
| 491 | $C_2H_5$ | H | F | F | Bond | n-$C_4H_9$ |
| 492 | $C_2H_5$ | H | F | F | Bond | n-$C_5H_{11}$ |
| 493 | $C_2H_5$ | H | F | F | Bond | n-$C_6H_{13}$ |
| 494 | $C_2H_5$ | H | F | F | Bond | n-$C_7H_{15}$ |
| 495 | $C_2H_5$ | F | F | F | $CF_2CF_2$ | $CH_3$ |
| 496 | $C_2H_5$ | F | F | F | $CF_2CF_2$ | $C_2H_5$ |
| 497 | $C_2H_5$ | F | F | F | $CF_2CF_2$ | n-$C_3H_7$ |
| 498 | $C_2H_5$ | F | F | F | $CF_2CF_2$ | n-$C_4H_9$ |
| 499 | $C_2H_5$ | F | F | F | $CF_2CF_2$ | n-$C_5H_{11}$ |
| 500 | $C_2H_5$ | F | F | F | $CF_2CF_2$ | n-$C_6H_{13}$ |
| 501 | $C_2H_5$ | F | F | F | $CF_2CF_2$ | n-$C_7H_{15}$ |
| 502 | $C_2H_5$ | F | F | F | Bond | $CH_3$ |
| 503 | $C_2H_5$ | F | F | F | Bond | $C_2H_5$ |
| 504 | $C_2H_5$ | F | F | F | Bond | n-$C_3H_7$ |
| 505 | $C_2H_5$ | F | F | F | Bond | n-$C_4H_9$ |
| 506 | $C_2H_5$ | F | F | F | Bond | n-$C_5H_{11}$ |
| 507 | $C_2H_5$ | F | F | F | Bond | n-$C_6H_{13}$ |
| 508 | $C_2H_5$ | F | F | F | Bond | n-$C_7H_{15}$ |
| 509 | n-$C_3H_7$ | H | F | F | Bond | $CH_3$ |
| 510 | n-$C_3H_7$ | H | F | F | Bond | $C_2H_5$ |
| 511 | n-$C_3H_7$ | H | F | F | Bond | n-$C_3H_7$ |
| 512 | n-$C_3H_7$ | H | F | F | Bond | n-$C_4H_9$ |
| 513 | n-$C_3H_7$ | H | F | F | Bond | n-$C_5H_{11}$ |
| 514 | n-$C_3H_7$ | H | F | F | Bond | n-$C_6H_{13}$ |
| 515 | n-$C_3H_7$ | H | F | F | Bond | n-$C_7H_{15}$ |
| 516 | n-$C_3H_7$ | F | F | F | Bond | $CH_3$ |
| 517 | n-$C_3H_7$ | F | F | F | Bond | $C_2H_5$ |
| 518 | n-$C_3H_7$ | F | F | F | Bond | n-$C_4H_9$ |
| 519 | n-$C_3H_7$ | F | F | F | Bond | n-$C_5H_{11}$ |
| 520 | n-$C_3H_7$ | F | F | F | Bond | n-$C_6H_{13}$ |
| 521 | n-$C_3H_7$ | F | F | F | Bond | n-$C_7H_{15}$ |
| 522 | n-$C_4H_9$ | H | F | F | Bond | $CH_3$ |
| 523 | n-$C_4H_9$ | H | F | F | Bond | $C_2H_5$ |
| 524 | n-$C_4H_9$ | H | F | F | Bond | n-$C_3H_7$ |
| 525 | n-$C_4H_9$ | H | F | F | Bond | n-$C_4H_9$ |
| 526 | n-$C_4H_9$ | H | F | F | Bond | n-$C_5H_{11}$ |
| 527 | n-$C_4H_9$ | H | F | F | Bond | n-$C_6H_{13}$ |
| 528 | n-$C_4H_9$ | H | F | F | Bond | n-$C_7H_{15}$ |
| 529 | n-$C_4H_9$ | F | F | F | Bond | $CH_3$ |
| 530 | n-$C_4H_9$ | F | F | F | Bond | $C_2H_5$ |
| 531 | n-$C_4H_9$ | F | F | F | Bond | n-$C_3H_7$ |

-continued

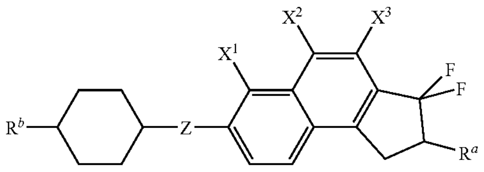

| Example | $R^b$ | $X^1$ | $X^2$ | $X^3$ | Z | $R^a$ |
|---|---|---|---|---|---|---|
| 532 | n-$C_4H_9$ | F | F | F | Bond | n-$C_4H_9$ |
| 533 | n-$C_4H_9$ | F | F | F | Bond | n-$C_5H_{11}$ |
| 534 | n-$C_4H_9$ | F | F | F | Bond | n-$C_6H_{13}$ |
| 535 | n-$C_4H_9$ | F | F | F | Bond | n-$C_7H_{15}$ |
| 536 | n-$C_5H_{11}$ | H | F | F | Bond | $CH_3$ |
| 537 | n-$C_5H_{11}$ | H | F | F | Bond | $C_2H_5$ |
| 538 | n-$C_5H_{11}$ | H | F | F | Bond | n-$C_3H_7$ |
| 539 | n-$C_5H_{11}$ | H | F | F | Bond | n-$C_4H_9$ |
| 540 | n-$C_5H_{11}$ | H | F | F | Bond | n-$C_5H_{11}$ |
| 541 | n-$C_5H_{11}$ | H | F | F | Bond | n-$C_6H_{13}$ |
| 542 | n-$C_5H_{11}$ | H | F | F | Bond | n-$C_7H_{15}$ |
| 543 | n-$C_5H_{11}$ | F | F | F | Bond | $CH_3$ |
| 544 | n-$C_5H_{11}$ | F | F | F | Bond | $C_2H_5$ |
| 545 | n-$C_5H_{11}$ | F | F | F | Bond | n-$C_3H_7$ |
| 546 | n-$C_5H_{11}$ | F | F | F | Bond | n-$C_4H_9$ |
| 547 | n-$C_5H_{11}$ | F | F | F | Bond | n-$C_5H_{11}$ |
| 548 | n-$C_5H_{11}$ | F | F | F | Bond | n-$C_6H_{13}$ |
| 549 | n-$C_5H_{11}$ | F | F | F | Bond | n-$C_7H_{15}$ |

Examples 550-646

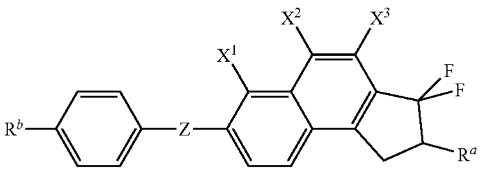

| Example | $R^b$ | $X^1$ | $X^2$ | $X^3$ | Z | $R^a$ |
|---|---|---|---|---|---|---|
| 550 | $CH_3$ | H | F | F | Bond | $CH_3$ |
| 551 | $CH_3$ | H | F | F | Bond | $C_2H_5$ |
| 552 | $CH_3$ | H | F | F | Bond | n-$C_3H_7$ |
| 553 | $CH_3$ | H | F | F | Bond | n-$C_4H_9$ |
| 554 | $CH_3$ | H | F | F | Bond | n-$C_5H_{11}$ |
| 555 | $CH_3$ | H | F | F | Bond | n-$C_6H_{13}$ |
| 556 | $CH_3$ | H | F | F | Bond | n-$C_7H_{15}$ |
| 557 | $CH_3$ | F | F | F | Bond | $CH_3$ |
| 558 | $CH_3$ | F | F | F | Bond | $C_2H_5$ |
| 559 | $CH_3$ | F | F | F | Bond | n-$C_3H_7$ |
| 560 | $CH_3$ | F | F | F | Bond | n-$C_4H_9$ |
| 561 | $CH_3$ | F | F | F | Bond | n-$C_5H_{11}$ |
| 562 | $CH_3$ | F | F | F | Bond | n-$C_6H_{13}$ |
| 563 | $CH_3$ | F | F | F | Bond | n-$C_7H_{15}$ |
| 564 | $CH_3$ | F | F | F | $CF_2CF_2$ | $CH_3$ |
| 565 | $CH_3$ | F | F | F | $CF_2CF_2$ | $C_2H_5$ |
| 566 | $CH_3$ | F | F | F | $CF_2CF_2$ | n-$C_3H_7$ |
| 567 | $CH_3$ | F | F | F | $CF_2CF_2$ | n-$C_4H_9$ |
| 568 | $CH_3$ | F | F | F | $CF_2CF_2$ | n-$C_5H_{11}$ |
| 569 | $CH_3$ | F | F | F | $CF_2CF_2$ | n-$C_6H_{13}$ |
| 570 | $CH_3$ | F | F | F | $CF_2CF_2$ | n-$C_7H_{15}$ |
| 571 | $CH_3$ | F | F | F | $CF_2O$ | $CH_3$ |
| 572 | $CH_3$ | F | F | F | $CF_2O$ | $C_2H_5$ |
| 573 | $CH_3$ | F | F | F | $CF_2O$ | n-$C_3H_7$ |
| 574 | $CH_3$ | F | F | F | $CF_2O$ | n-$C_4H_9$ |
| 575 | $CH_3$ | F | F | F | $CF_2O$ | n-$C_5H_{11}$ |
| 576 | $CH_3$ | F | F | F | $CF_2O$ | n-$C_6H_{13}$ |
| 577 | $CH_3$ | F | F | F | $CF_2O$ | n-$C_7H_{15}$ |
| 578 | $C_2H_5$ | H | F | F | Bond | $CH_3$ |
| 579 | $C_2H_5$ | H | F | F | Bond | $C_2H_5$ |

-continued

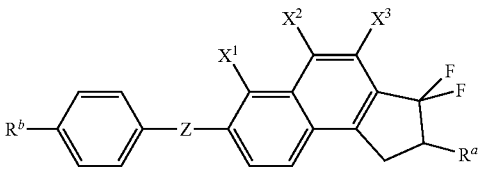

| Example | $R^b$ | $X^1$ | $X^2$ | $X^3$ | Z | $R^a$ |
|---|---|---|---|---|---|---|
| 580 | $C_2H_5$ | H | F | F | Bond | n-$C_3H_7$ |
| 581 | $C_2H_5$ | H | F | F | Bond | n-$C_4H_9$ |
| 582 | $C_2H_5$ | H | F | F | Bond | n-$C_5H_{11}$ |
| 583 | $C_2H_5$ | H | F | F | Bond | n-$C_6H_{13}$ |
| 584 | $C_2H_5$ | H | F | F | Bond | n-$C_7H_{15}$ |
| 585 | $C_2H_5$ | F | F | F | $CF_2CF_2$ | $CH_3$ |
| 586 | $C_2H_5$ | F | F | F | $CF_2CF_2$ | $C_2H_5$ |
| 587 | $C_2H_5$ | F | F | F | $CF_2CF_2$ | n-$C_4H_9$ |
| 588 | $C_2H_5$ | F | F | F | $CF_2CF_2$ | n-$C_5H_{11}$ |
| 589 | $C_2H_5$ | F | F | F | $CF_2CF_2$ | n-$C_6H_{13}$ |
| 590 | $C_2H_5$ | F | F | F | $CF_2CF_2$ | n-$C_7H_{15}$ |
| 591 | $C_2H_5$ | F | F | F | $CF_2O$ | $CH_3$ |
| 592 | $C_2H_5$ | F | F | F | $CF_2O$ | $C_2H_5$ |
| 593 | $C_2H_5$ | F | F | F | $CF_2O$ | n-$C_3H_7$ |
| 594 | $C_2H_5$ | F | F | F | $CF_2O$ | n-$C_4H_9$ |
| 595 | $C_2H_5$ | F | F | F | $CF_2O$ | n-$C_5H_{11}$ |
| 596 | $C_2H_5$ | F | F | F | $CF_2O$ | n-$C_6H_{13}$ |
| 597 | $C_2H_5$ | F | F | F | $CF_2O$ | n-$C_7H_{15}$ |
| 598 | $C_2H_5$ | F | F | F | Bond | $CH_3$ |
| 599 | $C_2H_5$ | F | F | F | Bond | $C_2H_5$ |
| 600 | $C_2H_5$ | F | F | F | Bond | n-$C_3H_7$ |
| 601 | $C_2H_5$ | F | F | F | Bond | n-$C_4H_9$ |
| 602 | $C_2H_5$ | F | F | F | Bond | n-$C_5H_{11}$ |
| 603 | $C_2H_5$ | F | F | F | Bond | n-$C_6H_{13}$ |
| 604 | $C_2H_5$ | F | F | F | Bond | n-$C_7H_{15}$ |
| 605 | n-$C_3H_7$ | H | F | F | Bond | $CH_3$ |
| 606 | n-$C_3H_7$ | H | F | F | Bond | $C_2H_5$ |
| 607 | n-$C_3H_7$ | H | F | F | Bond | n-$C_3H_7$ |
| 608 | n-$C_3H_7$ | H | F | F | Bond | n-$C_4H_9$ |
| 609 | n-$C_3H_7$ | H | F | F | Bond | n-$C_5H_{11}$ |
| 610 | n-$C_3H_7$ | H | F | F | Bond | n-$C_6H_{13}$ |
| 611 | n-$C_3H_7$ | H | F | F | Bond | n-$C_7H_{15}$ |
| 612 | n-$C_3H_7$ | F | F | F | Bond | $CH_3$ |
| 613 | n-$C_3H_7$ | F | F | F | Bond | $C_2H_5$ |
| 614 | n-$C_3H_7$ | F | F | F | Bond | n-$C_3H_7$ |
| 615 | n-$C_3H_7$ | F | F | F | Bond | n-$C_4H_9$ |
| 616 | n-$C_3H_7$ | F | F | F | Bond | n-$C_5H_{11}$ |
| 617 | n-$C_3H_7$ | F | F | F | Bond | n-$C_6H_{13}$ |
| 618 | n-$C_3H_7$ | F | F | F | Bond | n-$C_7H_{15}$ |
| 619 | n-$C_4H_9$ | H | F | F | Bond | $CH_3$ |
| 620 | n-$C_4H_9$ | H | F | F | Bond | $C_2H_5$ |
| 621 | n-$C_4H_9$ | H | F | F | Bond | n-$C_3H_7$ |
| 622 | n-$C_4H_9$ | H | F | F | Bond | n-$C_4H_9$ |
| 623 | n-$C_4H_9$ | H | F | F | Bond | n-$C_5H_{11}$ |
| 624 | n-$C_4H_9$ | H | F | F | Bond | n-$C_6H_{13}$ |
| 625 | n-$C_4H_9$ | H | F | F | Bond | n-$C_7H_{15}$ |
| 626 | n-$C_4H_9$ | F | F | F | Bond | $CH_3$ |
| 627 | n-$C_4H_9$ | F | F | F | Bond | $C_2H_5$ |
| 628 | n-$C_4H_9$ | F | F | F | Bond | n-$C_3H_7$ |
| 629 | n-$C_4H_9$ | F | F | F | Bond | n-$C_4H_9$ |
| 630 | n-$C_4H_9$ | F | F | F | Bond | n-$C_5H_{11}$ |
| 631 | n-$C_4H_9$ | F | F | F | Bond | n-$C_6H_{13}$ |
| 632 | n-$C_4H_9$ | F | F | F | Bond | n-$C_7H_{15}$ |
| 633 | n-$C_5H_{11}$ | H | F | F | Bond | $CH_3$ |
| 634 | n-$C_5H_{11}$ | H | F | F | Bond | $C_2H_5$ |
| 635 | n-$C_5H_{11}$ | H | F | F | Bond | n-$C_3H_7$ |
| 636 | n-$C_5H_{11}$ | H | F | F | Bond | n-$C_4H_9$ |
| 637 | n-$C_5H_{11}$ | H | F | F | Bond | n-$C_5H_{11}$ |
| 638 | n-$C_5H_{11}$ | H | F | F | Bond | n-$C_6H_{13}$ |
| 639 | n-$C_5H_{11}$ | H | F | F | Bond | n-$C_7H_{15}$ |
| 640 | n-$C_5H_{11}$ | F | F | F | Bond | $CH_3$ |
| 641 | n-$C_5H_{11}$ | F | F | F | Bond | $C_2H_5$ |
| 642 | n-$C_5H_{11}$ | F | F | F | Bond | n-$C_3H_7$ |
| 643 | n-$C_5H_{11}$ | F | F | F | Bond | n-$C_4H_9$ |
| 644 | n-$C_5H_{11}$ | F | F | F | Bond | n-$C_5H_{11}$ |
| 645 | n-$C_5H_{11}$ | F | F | F | Bond | n-$C_6H_{13}$ |
| 646 | n-$C_5H_{11}$ | F | F | F | Bond | n-$C_7H_{15}$ |

Examples 647-765

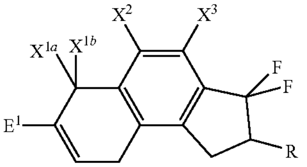

| Example | $E^1$ | $X^{1a}$ | $X^{1b}$ | $X^2$ | $X^3$ | R |
|---|---|---|---|---|---|---|
| 647 | H | H | H | H | H | $CH_3$ |
| 648 | H | H | H | H | H | $C_2H_5$ |
| 649 | H | H | H | H | H | $n-C_3H_7$ |
| 650 | H | H | H | H | H | $n-C_4H_9$ |
| 651 | H | H | H | H | H | $n-C_5H_{11}$ |
| 652 | H | H | H | H | H | $n-C_6H_{13}$ |
| 653 | H | H | H | H | H | $n-C_7H_{15}$ |
| 654 | H | H | H | H | F | $CH_3$ |
| 655 | H | H | H | H | F | $C_2H_5$ |
| 656 | H | H | H | H | F | $n-C_3H_7$ |
| 657 | H | H | H | H | F | $n-C_4H_9$ |
| 658 | H | H | H | H | F | $n-C_5H_{11}$ |
| 659 | H | H | H | H | F | $n-C_6H_{13}$ |
| 660 | H | H | H | H | F | $n-C_7H_{15}$ |
| 661 | H | H | H | F | F | $CH_3$ |
| 662 | H | H | H | F | F | $C_2H_5$ |
| 663 | H | H | H | F | F | $n-C_3H_7$ |
| 664 | H | H | H | F | F | $n-C_4H_9$ |
| 665 | H | H | H | F | F | $n-C_5H_{11}$ |
| 666 | H | H | H | F | F | $n-C_6H_{13}$ |
| 667 | H | H | H | F | F | $n-C_7H_{15}$ |
| 668 | H | H | F | F | F | $CH_3$ |
| 669 | H | H | F | F | F | $C_2H_5$ |
| 670 | H | H | F | F | F | $n-C_3H_7$ |
| 671 | H | H | F | F | F | $n-C_4H_9$ |
| 672 | H | H | F | F | F | $n-C_5H_{11}$ |
| 673 | H | H | F | F | F | $n-C_6H_{13}$ |
| 674 | H | H | F | F | F | $n-C_7H_{15}$ |
| 675 | H | F | F | F | F | $CH_3$ |
| 676 | H | F | F | F | F | $C_2H_5$ |
| 677 | H | F | F | F | F | $n-C_3H_7$ |
| 678 | H | F | F | F | F | $n-C_4H_9$ |
| 679 | H | F | F | F | F | $n-C_5H_{11}$ |
| 680 | H | F | F | F | F | $n-C_6H_{13}$ |
| 681 | H | F | F | F | F | $n-C_7H_{15}$ |
| 682 | $CH_3$ | H | H | F | F | $CH_3$ |
| 683 | $CH_3$ | H | H | F | F | $C_2H_5$ |
| 684 | $CH_3$ | H | H | F | F | $n-C_3H_7$ |
| 685 | $CH_3$ | H | H | F | F | $n-C_4H_9$ |
| 686 | $CH_3$ | H | H | F | F | $n-C_5H_{11}$ |
| 687 | $CH_3$ | H | H | F | F | $n-C_6H_{13}$ |
| 688 | $CH_3$ | H | H | F | F | $n-C_7H_{15}$ |
| 689 | $CH_3$ | H | F | F | F | $CH_3$ |
| 690 | $CH_3$ | H | F | F | F | $C_2H_5$ |
| 691 | $CH_3$ | H | F | F | F | $n-C_3H_7$ |
| 692 | $CH_3$ | H | F | F | F | $n-C_4H_9$ |
| 693 | $CH_3$ | H | F | F | F | $n-C_5H_{11}$ |
| 694 | $CH_3$ | H | F | F | F | $n-C_6H_{13}$ |
| 695 | $CH_3$ | H | F | F | F | $n-C_7H_{15}$ |
| 696 | $CH_3$ | F | F | F | F | $CH_3$ |
| 697 | $CH_3$ | F | F | F | F | $C_2H_5$ |
| 698 | $CH_3$ | F | F | F | F | $n-C_3H_7$ |
| 699 | $CH_3$ | F | F | F | F | $n-C_4H_9$ |
| 700 | $CH_3$ | F | F | F | F | $n-C_5H_{11}$ |
| 701 | $CH_3$ | F | F | F | F | $n-C_6H_{13}$ |
| 702 | $CH_3$ | F | F | F | F | $n-C_7H_{15}$ |
| 703 | $C_2H_5$ | H | H | F | F | $CH_3$ |
| 704 | $C_2H_5$ | H | H | F | F | $C_2H_5$ |
| 705 | $C_2H_5$ | H | H | F | F | $n-C_3H_7$ |
| 706 | $C_2H_5$ | H | H | F | F | $n-C_4H_9$ |
| 707 | $C_2H_5$ | H | H | F | F | $n-C_5H_{11}$ |
| 708 | $C_2H_5$ | H | H | F | F | $n-C_6H_{13}$ |
| 709 | $C_2H_5$ | H | H | F | F | $n-C_7H_{15}$ |
| 710 | $C_2H_5$ | H | F | F | F | $CH_3$ |
| 711 | $C_2H_5$ | H | F | F | F | $C_2H_5$ |

-continued

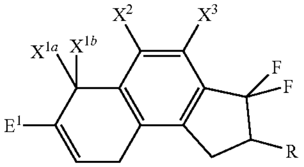

| Example | $E^1$ | $X^{1a}$ | $X^{1b}$ | $X^2$ | $X^3$ | R |
|---|---|---|---|---|---|---|
| 712 | $C_2H_5$ | H | F | F | F | $n-C_3H_7$ |
| 713 | $C_2H_5$ | H | F | F | F | $n-C_4H_9$ |
| 714 | $C_2H_5$ | H | F | F | F | $n-C_5H_{11}$ |
| 715 | $C_2H_5$ | H | F | F | F | $n-C_6H_{13}$ |
| 716 | $C_2H_5$ | H | F | F | F | $n-C_7H_{15}$ |
| 717 | $C_2H_5$ | F | F | F | F | $CH_3$ |
| 718 | $C_2H_5$ | F | F | F | F | $C_2H_5$ |
| 719 | $C_2H_5$ | F | F | F | F | $n-C_3H_7$ |
| 720 | $C_2H_5$ | F | F | F | F | $n-C_4H_9$ |
| 721 | $C_2H_5$ | F | F | F | F | $n-C_5H_{11}$ |
| 722 | $C_2H_5$ | F | F | F | F | $n-C_6H_{13}$ |
| 723 | $C_2H_5$ | F | F | F | F | $n-C_7H_{15}$ |
| 724 | $n-C_3H_7$ | H | H | F | F | $CH_3$ |
| 725 | $n-C_3H_7$ | H | H | F | F | $C_2H_5$ |
| 726 | $n-C_3H_7$ | H | H | F | F | $n-C_3H_7$ |
| 727 | $n-C_3H_7$ | H | H | F | F | $n-C_4H_9$ |
| 728 | $n-C_3H_7$ | H | H | F | F | $n-C_5H_{11}$ |
| 729 | $n-C_3H_7$ | H | H | F | F | $n-C_6H_{13}$ |
| 730 | $n-C_3H_7$ | H | H | F | F | $n-C_7H_{15}$ |
| 731 | $n-C_3H_7$ | F | F | F | F | $CH_3$ |
| 732 | $n-C_3H_7$ | F | F | F | F | $C_2H_5$ |
| 733 | $n-C_3H_7$ | F | F | F | F | $n-C_3H_7$ |
| 734 | $n-C_3H_7$ | F | F | F | F | $n-C_4H_9$ |
| 735 | $n-C_3H_7$ | F | F | F | F | $n-C_5H_{11}$ |
| 736 | $n-C_3H_7$ | F | F | F | F | $n-C_6H_{13}$ |
| 737 | $n-C_3H_7$ | F | F | F | F | $n-C_7H_{15}$ |
| 738 | $n-C_4H_9$ | H | H | F | F | $CH_3$ |
| 739 | $n-C_4H_9$ | H | H | F | F | $C_2H_5$ |
| 740 | $n-C_4H_9$ | H | H | F | F | $n-C_3H_7$ |
| 741 | $n-C_4H_9$ | H | H | F | F | $n-C_4H_9$ |
| 742 | $n-C_4H_9$ | H | H | F | F | $n-C_5H_{11}$ |
| 743 | $n-C_4H_9$ | H | H | F | F | $n-C_6H_{13}$ |
| 744 | $n-C_4H_9$ | H | H | F | F | $n-C_7H_{15}$ |
| 745 | $n-C_4H_9$ | F | F | F | F | $CH_3$ |
| 746 | $n-C_4H_9$ | F | F | F | F | $C_2H_5$ |
| 747 | $n-C_4H_9$ | F | F | F | F | $n-C_3H_7$ |
| 748 | $n-C_4H_9$ | F | F | F | F | $n-C_4H_9$ |
| 749 | $n-C_4H_9$ | F | F | F | F | $n-C_5H_{11}$ |
| 750 | $n-C_4H_9$ | F | F | F | F | $n-C_6H_{13}$ |
| 751 | $n-C_4H_9$ | F | F | F | F | $n-C_7H_{15}$ |
| 752 | $n-C_5H_{11}$ | H | H | F | F | $CH_3$ |
| 753 | $n-C_5H_{11}$ | H | H | F | F | $C_2H_5$ |
| 754 | $n-C_5H_{11}$ | H | H | F | F | $n-C_3H_7$ |
| 755 | $n-C_5H_{11}$ | H | H | F | F | $n-C_4H_9$ |
| 756 | $n-C_5H_{11}$ | H | H | F | F | $n-C_5H_{11}$ |
| 757 | $n-C_5H_{11}$ | H | H | F | F | $n-C_6H_{13}$ |
| 758 | $n-C_5H_{11}$ | H | H | F | F | $n-C_7H_{15}$ |
| 759 | $n-C_5H_{11}$ | F | F | F | F | $CH_3$ |
| 760 | $n-C_5H_{11}$ | F | F | F | F | $C_2H_5$ |
| 761 | $n-C_5H_{11}$ | F | F | F | F | $n-C_3H_7$ |
| 762 | $n-C_5H_{11}$ | F | F | F | F | $n-C_4H_9$ |
| 763 | $n-C_5H_{11}$ | F | F | F | F | $n-C_5H_{11}$ |
| 764 | $n-C_5H_{11}$ | F | F | F | F | $n-C_6H_{13}$ |
| 765 | $n-C_5H_{11}$ | F | F | F | F | $n-C_7H_{15}$ |

Examples 766-912

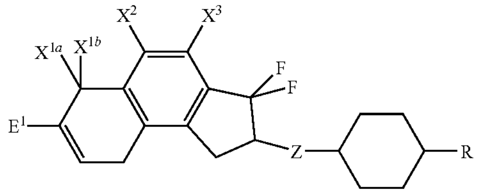

| Example | $E^1$ | $X^{1a}$ | $X^{1b}$ | $X^2$ | $X^3$ | Z | R |
|---|---|---|---|---|---|---|---|
| 766 | H | H | H | H | F | Bond | $CH_3$ |
| 767 | H | H | H | H | F | Bond | $C_2H_5$ |
| 768 | H | H | H | H | F | Bond | n-$C_3H_7$ |
| 769 | H | H | H | H | F | Bond | n-$C_4H_9$ |
| 770 | H | H | H | H | F | Bond | n-$C_5H_{11}$ |
| 771 | H | H | H | H | F | Bond | n-$C_6H_{13}$ |
| 772 | H | H | H | H | F | Bond | n-$C_7H_{15}$ |
| 773 | H | H | H | F | F | Bond | $CH_3$ |
| 774 | H | H | H | F | F | Bond | $C_2H_5$ |
| 775 | H | H | H | F | F | Bond | n-$C_3H_7$ |
| 776 | H | H | H | F | F | Bond | n-$C_4H_9$ |
| 777 | H | H | H | F | F | Bond | n-$C_5H_{11}$ |
| 778 | H | H | H | F | F | Bond | n-$C_6H_{13}$ |
| 779 | H | H | H | F | F | Bond | n-$C_7H_{15}$ |
| 780 | H | H | F | F | F | Bond | $CH_3$ |
| 781 | H | H | F | F | F | Bond | $C_2H_5$ |
| 782 | H | H | F | F | F | Bond | n-$C_3H_7$ |
| 783 | H | H | F | F | F | Bond | n-$C_4H_9$ |
| 784 | H | H | F | F | F | Bond | n-$C_5H_{11}$ |
| 785 | H | H | F | F | F | Bond | n-$C_6H_{13}$ |
| 786 | H | H | F | F | F | Bond | n-$C_7H_{15}$ |
| 787 | H | F | F | F | F | Bond | $CH_3$ |
| 788 | H | F | F | F | F | Bond | $C_2H_5$ |
| 789 | H | F | F | F | F | Bond | n-$C_3H_7$ |
| 790 | H | F | F | F | F | Bond | n-$C_4H_9$ |
| 791 | H | F | F | F | F | Bond | n-$C_5H_{11}$ |
| 792 | H | F | F | F | F | Bond | n-$C_6H_{13}$ |
| 793 | H | F | F | F | F | Bond | n-$C_7H_{15}$ |
| 794 | H | H | F | F | F | $CF_2CF_2$ | $CH_3$ |
| 795 | H | H | F | F | F | $CF_2CF_2$ | $C_2H_5$ |
| 796 | H | H | F | F | F | $CF_2CF_2$ | n-$C_3H_7$ |
| 797 | H | H | F | F | F | $CF_2CF_2$ | n-$C_4H_9$ |
| 798 | H | H | F | F | F | $CF_2CF_2$ | n-$C_5H_{11}$ |
| 799 | H | H | F | F | F | $CF_2CF_2$ | n-$C_6H_{13}$ |
| 800 | H | H | F | F | F | $CF_2CF_2$ | n-$C_7H_{15}$ |
| 801 | H | F | F | F | F | $CF_2CF_2$ | $CH_3$ |
| 802 | H | F | F | F | F | $CF_2CF_2$ | $C_2H_5$ |
| 803 | H | F | F | F | F | $CF_2CF_2$ | n-$C_3H_7$ |
| 804 | H | F | F | F | F | $CF_2CF_2$ | n-$C_4H_9$ |
| 805 | H | F | F | F | F | $CF_2CF_2$ | n-$C_5H_{11}$ |
| 806 | H | F | F | F | F | $CF_2CF_2$ | n-$C_6H_{13}$ |
| 807 | H | F | F | F | F | $CF_2CF_2$ | n-$C_7H_{15}$ |
| 808 | H | F | F | F | F | $OCF_2$ | $CH_3$ |
| 809 | H | F | F | F | F | $OCF_2$ | $C_2H_5$ |
| 810 | H | F | F | F | F | $OCF_2$ | n-$C_3H_7$ |
| 811 | H | F | F | F | F | $OCF_2$ | n-$C_4H_9$ |
| 812 | H | F | F | F | F | $OCF_2$ | n-$C_5H_{11}$ |
| 813 | H | F | F | F | F | $OCF_2$ | n-$C_6H_{13}$ |
| 814 | H | F | F | F | F | $OCF_2$ | n-$C_7H_{15}$ |
| 815 | $CH_3$ | H | H | F | F | Bond | $CH_3$ |
| 816 | $CH_3$ | H | H | F | F | Bond | $C_2H_5$ |
| 817 | $CH_3$ | H | H | F | F | Bond | n-$C_3H_7$ |
| 818 | $CH_3$ | H | H | F | F | Bond | n-$C_4H_9$ |
| 819 | $CH_3$ | H | H | F | F | Bond | n-$C_5H_{11}$ |
| 820 | $CH_3$ | H | H | F | F | Bond | n-$C_6H_{13}$ |
| 821 | $CH_3$ | H | H | F | F | Bond | n-$C_7H_{15}$ |
| 822 | $CH_3$ | H | F | F | F | Bond | $CH_3$ |
| 823 | $CH_3$ | H | F | F | F | Bond | $C_2H_5$ |
| 824 | $CH_3$ | H | F | F | F | Bond | n-$C_3H_7$ |
| 825 | $CH_3$ | H | F | F | F | Bond | n-$C_4H_9$ |
| 826 | $CH_3$ | H | F | F | F | Bond | n-$C_5H_{11}$ |
| 827 | $CH_3$ | H | F | F | F | Bond | n-$C_6H_{13}$ |
| 828 | $CH_3$ | H | F | F | F | Bond | n-$C_7H_{15}$ |
| 829 | $CH_3$ | F | F | F | F | Bond | $CH_3$ |

-continued

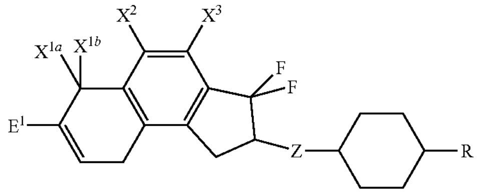

| Example | $E^1$ | $X^{1a}$ | $X^{1b}$ | $X^2$ | $X^3$ | Z | R |
|---|---|---|---|---|---|---|---|
| 830 | $CH_3$ | F | F | F | F | Bond | $C_2H_5$ |
| 831 | $CH_3$ | F | F | F | F | Bond | n-$C_3H_7$ |
| 832 | $CH_3$ | F | F | F | F | Bond | n-$C_4H_9$ |
| 833 | $CH_3$ | F | F | F | F | Bond | n-$C_5H_{11}$ |
| 834 | $CH_3$ | F | F | F | F | Bond | n-$C_6H_{13}$ |
| 835 | $CH_3$ | F | F | F | F | Bond | n-$C_7H_{15}$ |
| 836 | $CH_3$ | F | F | F | F | $CF_2CF_2$ | $CH_3$ |
| 837 | $CH_3$ | F | F | F | F | $CF_2CF_2$ | $C_2H_5$ |
| 838 | $CH_3$ | F | F | F | F | $CF_2CF_2$ | n-$C_3H_7$ |
| 839 | $CH_3$ | F | F | F | F | $CF_2CF_2$ | n-$C_4H_9$ |
| 840 | $CH_3$ | F | F | F | F | $CF_2CF_2$ | n-$C_5H_{11}$ |
| 841 | $CH_3$ | F | F | F | F | $CF_2CF_2$ | n-$C_6H_{13}$ |
| 842 | $CH_3$ | F | F | F | F | $CF_2CF_2$ | n-$C_7H_{15}$ |
| 843 | $CH_3$ | F | F | F | F | $OCF_2$ | $CH_3$ |
| 844 | $CH_3$ | F | F | F | F | $OCF_2$ | $C_2H_5$ |
| 845 | $CH_3$ | F | F | F | F | $OCF_2$ | n-$C_3H_7$ |
| 846 | $CH_3$ | F | F | F | F | $OCF_2$ | n-$C_4H_9$ |
| 847 | $CH_3$ | F | F | F | F | $OCF_2$ | n-$C_5H_{11}$ |
| 848 | $CH_3$ | F | F | F | F | $OCF_2$ | n-$C_6H_{13}$ |
| 849 | $CH_3$ | F | F | F | F | $OCF_2$ | n-$C_7H_{15}$ |
| 850 | $C_2H_5$ | H | H | F | F | Bond | $CH_3$ |
| 851 | $C_2H_5$ | H | H | F | F | Bond | $C_2H_5$ |
| 852 | $C_2H_5$ | H | H | F | F | Bond | n-$C_3H_7$ |
| 853 | $C_2H_5$ | H | H | F | F | Bond | n-$C_4H_9$ |
| 854 | $C_2H_5$ | H | H | F | F | Bond | n-$C_5H_{11}$ |
| 855 | $C_2H_5$ | H | H | F | F | Bond | n-$C_6H_{13}$ |
| 856 | $C_2H_5$ | H | H | F | F | Bond | n-$C_7H_{15}$ |
| 857 | $C_2H_5$ | F | F | F | F | Bond | $CH_3$ |
| 858 | $C_2H_5$ | F | F | F | F | Bond | $C_2H_5$ |
| 859 | $C_2H_5$ | F | F | F | F | Bond | n-$C_3H_7$ |
| 860 | $C_2H_5$ | F | F | F | F | Bond | n-$C_4H_9$ |
| 861 | $C_2H_5$ | F | F | F | F | Bond | n-$C_5H_{11}$ |
| 862 | $C_2H_5$ | F | F | F | F | Bond | n-$C_6H_{13}$ |
| 863 | $C_2H_5$ | F | F | F | F | Bond | n-$C_7H_{15}$ |
| 864 | n-$C_3H_7$ | H | H | F | F | Bond | $CH_3$ |
| 865 | n-$C_3H_7$ | H | H | F | F | Bond | $C_2H_5$ |
| 866 | n-$C_3H_7$ | H | H | F | F | Bond | n-$C_3H_7$ |
| 867 | n-$C_3H_7$ | H | H | F | F | Bond | n-$C_4H_9$ |
| 868 | n-$C_3H_7$ | H | H | F | F | Bond | n-$C_5H_{11}$ |
| 869 | n-$C_3H_7$ | H | H | F | F | Bond | n-$C_6H_{13}$ |
| 870 | n-$C_3H_7$ | H | H | F | F | Bond | n-$C_7H_{15}$ |
| 871 | n-$C_3H_7$ | H | F | F | F | Bond | $CH_3$ |
| 872 | n-$C_3H_7$ | H | F | F | F | Bond | $C_2H_5$ |
| 873 | n-$C_3H_7$ | H | F | F | F | Bond | n-$C_3H_7$ |
| 874 | n-$C_3H_7$ | H | F | F | F | Bond | n-$C_4H_9$ |
| 875 | n-$C_3H_7$ | H | F | F | F | Bond | n-$C_5H_{11}$ |
| 876 | n-$C_3H_7$ | H | F | F | F | Bond | n-$C_6H_{13}$ |
| 877 | n-$C_3H_7$ | H | F | F | F | Bond | n-$C_7H_{15}$ |
| 878 | n-$C_3H_7$ | F | F | F | F | Bond | $CH_3$ |
| 879 | n-$C_3H_7$ | F | F | F | F | Bond | $C_2H_5$ |
| 880 | n-$C_3H_7$ | F | F | F | F | Bond | n-$C_3H_7$ |
| 881 | n-$C_3H_7$ | F | F | F | F | Bond | n-$C_4H_9$ |
| 882 | n-$C_3H_7$ | F | F | F | F | Bond | n-$C_5H_{11}$ |
| 883 | n-$C_3H_7$ | F | F | F | F | Bond | n-$C_6H_{13}$ |
| 884 | n-$C_3H_7$ | F | F | F | F | Bond | n-$C_7H_{15}$ |
| 885 | n-$C_4H_9$ | H | H | F | F | Bond | $CH_3$ |
| 886 | n-$C_4H_9$ | H | H | F | F | Bond | $C_2H_5$ |
| 887 | n-$C_4H_9$ | H | H | F | F | Bond | n-$C_3H_7$ |
| 888 | n-$C_4H_9$ | H | H | F | F | Bond | n-$C_4H_9$ |
| 889 | n-$C_4H_9$ | H | H | F | F | Bond | n-$C_5H_{11}$ |
| 890 | n-$C_4H_9$ | H | H | F | F | Bond | n-$C_6H_{13}$ |
| 891 | n-$C_4H_9$ | H | H | F | F | Bond | n-$C_7H_{15}$ |
| 892 | n-$C_4H_9$ | F | F | F | F | Bond | $CH_3$ |
| 893 | n-$C_4H_9$ | F | F | F | F | Bond | $C_2H_5$ |
| 894 | n-$C_4H_9$ | F | F | F | F | Bond | n-$C_3H_7$ |
| 895 | n-$C_4H_9$ | F | F | F | F | Bond | n-$C_4H_9$ |
| 896 | n-$C_4H_9$ | F | F | F | F | Bond | n-$C_5H_{11}$ |

-continued

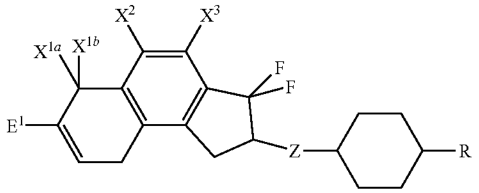

| Example | $E^1$ | $X^{1a}$ | $X^{1b}$ | $X^2$ | $X^3$ | Z | R |
|---|---|---|---|---|---|---|---|
| 897 | n-$C_4H_9$ | F | F | F | F | Bond | n-$C_6H_{13}$ |
| 898 | n-$C_4H_9$ | F | F | F | F | Bond | n-$C_7H_{15}$ |
| 899 | n-$C_5H_{11}$ | H | H | F | F | Bond | $CH_3$ |
| 900 | n-$C_5H_{11}$ | H | H | F | F | Bond | $C_2H_5$ |
| 901 | n-$C_5H_{11}$ | H | H | F | F | Bond | n-$C_3H_7$ |
| 902 | n-$C_5H_{11}$ | H | H | F | F | Bond | n-$C_4H_9$ |
| 903 | n-$C_5H_{11}$ | H | H | F | F | Bond | n-$C_5H_{11}$ |
| 904 | n-$C_5H_{11}$ | H | H | F | F | Bond | n-$C_6H_{13}$ |
| 905 | n-$C_5H_{11}$ | H | H | F | F | Bond | n-$C_7H_{15}$ |
| 906 | n-$C_5H_{11}$ | F | F | F | F | Bond | $CH_3$ |
| 907 | n-$C_5H_{11}$ | F | F | F | F | Bond | $C_2H_5$ |
| 908 | n-$C_5H_{11}$ | F | F | F | F | Bond | n-$C_3H_7$ |
| 909 | n-$C_5H_{11}$ | F | F | F | F | Bond | n-$C_4H_9$ |
| 910 | n-$C_5H_{11}$ | F | F | F | F | Bond | n-$C_5H_{11}$ |
| 911 | n-$C_5H_{11}$ | F | F | F | F | Bond | n-$C_6H_{13}$ |
| 912 | n-$C_5H_{11}$ | F | F | F | F | Bond | n-$C_7H_{15}$ |

Examples 913-1059

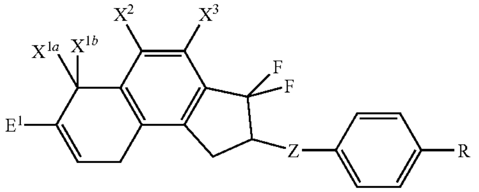

| Example | $E^1$ | $X^{1a}$ | $X^{1b}$ | $X^2$ | $X^3$ | Z | R |
|---|---|---|---|---|---|---|---|
| 913 | H | H | H | H | F | Bond | $CH_3$ |
| 914 | H | H | H | H | F | Bond | $C_2H_5$ |
| 915 | H | H | H | H | F | Bond | n-$C_3H_7$ |
| 916 | H | H | H | H | F | Bond | n-$C_4H_9$ |
| 917 | H | H | H | H | F | Bond | n-$C_5H_{11}$ |
| 918 | H | H | H | H | F | Bond | n-$C_6H_{13}$ |
| 919 | H | H | H | H | F | Bond | n-$C_7H_{15}$ |
| 920 | H | H | H | F | F | Bond | $CH_3$ |
| 921 | H | H | H | F | F | Bond | $C_2H_5$ |
| 922 | H | H | H | F | F | Bond | n-$C_3H_7$ |
| 923 | H | H | H | F | F | Bond | n-$C_4H_9$ |
| 924 | H | H | H | F | F | Bond | n-$C_5H_{11}$ |
| 925 | H | H | H | F | F | Bond | n-$C_6H_{13}$ |
| 926 | H | H | H | F | F | Bond | n-$C_7H_{15}$ |
| 927 | H | H | F | F | F | Bond | $CH_3$ |
| 928 | H | H | F | F | F | Bond | $C_2H_5$ |
| 929 | H | H | F | F | F | Bond | n-$C_3H_7$ |
| 930 | H | H | F | F | F | Bond | n-$C_4H_9$ |
| 931 | H | H | F | F | F | Bond | n-$C_5H_{11}$ |
| 932 | H | H | F | F | F | Bond | n-$C_6H_{13}$ |
| 933 | H | H | F | F | F | Bond | n-$C_7H_{15}$ |
| 934 | H | F | F | F | F | Bond | $CH_3$ |
| 935 | H | F | F | F | F | Bond | $C_2H_5$ |
| 936 | H | F | F | F | F | Bond | n-$C_3H_7$ |
| 937 | H | F | F | F | F | Bond | n-$C_4H_9$ |
| 938 | H | F | F | F | F | Bond | n-$C_5H_{11}$ |
| 939 | H | F | F | F | F | Bond | n-$C_6H_{13}$ |
| 940 | H | F | F | F | F | Bond | n-$C_7H_{15}$ |
| 941 | H | H | F | F | F | $CF_2CF_2$ | $CH_3$ |
| 942 | H | H | F | F | F | $CF_2CF_2$ | $C_2H_5$ |

-continued

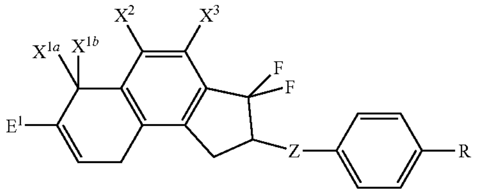

| Example | $E^1$ | $X^{1a}$ | $X^{1b}$ | $X^2$ | $X^3$ | Z | R |
|---|---|---|---|---|---|---|---|
| 943 | H | H | F | F | F | $CF_2CF_2$ | n-$C_3H_7$ |
| 944 | H | H | F | F | F | $CF_2CF_2$ | n-$C_4H_9$ |
| 945 | H | H | F | F | F | $CF_2CF_2$ | n-$C_5H_{11}$ |
| 946 | H | H | F | F | F | $CF_2CF_2$ | n-$C_6H_{13}$ |
| 947 | H | H | F | F | F | $CF_2CF_2$ | n-$C_7H_{15}$ |
| 948 | H | F | F | F | F | $CF_2CF_2$ | $CH_3$ |
| 949 | H | F | F | F | F | $CF_2CF_2$ | $C_2H_5$ |
| 950 | H | F | F | F | F | $CF_2CF_2$ | n-$C_3H_7$ |
| 951 | H | F | F | F | F | $CF_2CF_2$ | n-$C_4H_9$ |
| 952 | H | F | F | F | F | $CF_2CF_2$ | n-$C_5H_{11}$ |
| 953 | H | F | F | F | F | $CF_2CF_2$ | n-$C_6H_{13}$ |
| 954 | H | F | F | F | F | $CF_2CF_2$ | n-$C_7H_{15}$ |
| 955 | H | F | F | F | F | $CF_2O$ | $CH_3$ |
| 956 | H | F | F | F | F | $CF_2O$ | $C_2H_5$ |
| 957 | H | F | F | F | F | $CF_2O$ | n-$C_3H_7$ |
| 958 | H | F | F | F | F | $CF_2O$ | n-$C_4H_9$ |
| 959 | H | F | F | F | F | $CF_2O$ | n-$C_5H_{11}$ |
| 960 | H | F | F | F | F | $CF_2O$ | n-$C_6H_{13}$ |
| 961 | H | F | F | F | F | $CF_2O$ | n-$C_7H_{15}$ |
| 962 | $CH_3$ | H | H | F | F | Bond | $CH_3$ |
| 963 | $CH_3$ | H | H | F | F | Bond | $C_2H_5$ |
| 964 | $CH_3$ | H | H | F | F | Bond | n-$C_3H_7$ |
| 965 | $CH_3$ | H | H | F | F | Bond | n-$C_4H_9$ |
| 966 | $CH_3$ | H | H | F | F | Bond | n-$C_5H_{11}$ |
| 967 | $CH_3$ | H | H | F | F | Bond | n-$C_6H_{13}$ |
| 968 | $CH_3$ | H | H | F | F | Bond | n-$C_7H_{15}$ |
| 969 | $CH_3$ | H | F | F | F | Bond | $CH_3$ |
| 970 | $CH_3$ | H | F | F | F | Bond | $C_2H_5$ |
| 971 | $CH_3$ | H | F | F | F | Bond | n-$C_3H_7$ |
| 972 | $CH_3$ | H | F | F | F | Bond | n-$C_4H_9$ |
| 973 | $CH_3$ | H | F | F | F | Bond | n-$C_5H_{11}$ |
| 974 | $CH_3$ | H | F | F | F | Bond | n-$C_6H_{13}$ |
| 975 | $CH_3$ | H | F | F | F | Bond | n-$C_7H_{15}$ |
| 976 | $CH_3$ | F | F | F | F | Bond | $CH_3$ |
| 977 | $CH_3$ | F | F | F | F | Bond | $C_2H_5$ |
| 978 | $CH_3$ | F | F | F | F | Bond | n-$C_3H_7$ |
| 979 | $CH_3$ | F | F | F | F | Bond | n-$C_4H_9$ |
| 980 | $CH_3$ | F | F | F | F | Bond | n-$C_5H_{11}$ |
| 981 | $CH_3$ | F | F | F | F | Bond | n-$C_6H_{13}$ |
| 982 | $CH_3$ | F | F | F | F | Bond | n-$C_7H_{15}$ |
| 983 | $CH_3$ | F | F | F | F | $CF_2CF_2$ | $CH_3$ |
| 984 | $CH_3$ | F | F | F | F | $CF_2CF_2$ | $C_2H_5$ |
| 985 | $CH_3$ | F | F | F | F | $CF_2CF_2$ | n-$C_3H_7$ |
| 986 | $CH_3$ | F | F | F | F | $CF_2CF_2$ | n-$C_4H_9$ |
| 987 | $CH_3$ | F | F | F | F | $CF_2CF_2$ | n-$C_5H_{11}$ |
| 988 | $CH_3$ | F | F | F | F | $CF_2CF_2$ | n-$C_6H_{13}$ |
| 989 | $CH_3$ | F | F | F | F | $CF_2CF_2$ | n-$C_7H_{15}$ |
| 990 | $CH_3$ | F | F | F | F | $CF_2O$ | $CH_3$ |
| 991 | $CH_3$ | F | F | F | F | $CF_2O$ | $C_2H_5$ |
| 992 | $CH_3$ | F | F | F | F | $CF_2O$ | n-$C_3H_7$ |
| 993 | $CH_3$ | F | F | F | F | $CF_2O$ | n-$C_4H_9$ |
| 994 | $CH_3$ | F | F | F | F | $CF_2O$ | n-$C_5H_{11}$ |
| 995 | $CH_3$ | F | F | F | F | $CF_2O$ | n-$C_6H_{13}$ |
| 996 | $CH_3$ | F | F | F | F | $CF_2O$ | n-$C_7H_{15}$ |
| 997 | $C_2H_5$ | H | H | F | F | Bond | $CH_3$ |
| 998 | $C_2H_5$ | H | H | F | F | Bond | $C_2H_5$ |
| 999 | $C_2H_5$ | H | H | F | F | Bond | n-$C_3H_7$ |
| 1000 | $C_2H_5$ | H | H | F | F | Bond | n-$C_4H_9$ |
| 1001 | $C_2H_5$ | H | H | F | F | Bond | n-$C_5H_{11}$ |
| 1002 | $C_2H_5$ | H | H | F | F | Bond | n-$C_6H_{13}$ |
| 1003 | $C_2H_5$ | H | H | F | F | Bond | n-$C_7H_{15}$ |
| 1004 | $C_2H_5$ | F | F | F | F | Bond | $CH_3$ |
| 1005 | $C_2H_5$ | F | F | F | F | Bond | $C_2H_5$ |
| 1006 | $C_2H_5$ | F | F | F | F | Bond | n-$C_3H_7$ |
| 1007 | $C_2H_5$ | F | F | F | F | Bond | n-$C_4H_9$ |
| 1008 | $C_2H_5$ | F | F | F | F | Bond | n-$C_5H_{11}$ |
| 1009 | $C_2H_5$ | F | F | F | F | Bond | n-$C_6H_{13}$ |

-continued

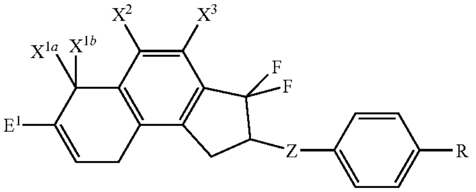

| Example | $E^1$ | $X^{1a}$ | $X^{1b}$ | $X^2$ | $X^3$ | Z | R |
|---|---|---|---|---|---|---|---|
| 1010 | $C_2H_5$ | F | F | F | F | Bond | $n-C_7H_{15}$ |
| 1011 | $n-C_3H_7$ | H | H | F | F | Bond | $CH_3$ |
| 1012 | $n-C_3H_7$ | H | H | F | F | Bond | $C_2H_5$ |
| 1013 | $n-C_3H_7$ | H | H | F | F | Bond | $n-C_3H_7$ |
| 1014 | $n-C_3H_7$ | H | H | F | F | Bond | $n-C_4H_9$ |
| 1015 | $n-C_3H_7$ | H | H | F | F | Bond | $n-C_5H_{11}$ |
| 1016 | $n-C_3H_7$ | H | H | F | F | Bond | $n-C_6H_{13}$ |
| 1017 | $n-C_3H_7$ | H | H | F | F | Bond | $n-C_7H_{15}$ |
| 1018 | $n-C_3H_7$ | H | F | F | F | Bond | $CH_3$ |
| 1019 | $n-C_3H_7$ | H | F | F | F | Bond | $C_2H_5$ |
| 1020 | $n-C_3H_7$ | H | F | F | F | Bond | $n-C_3H_7$ |
| 1021 | $n-C_3H_7$ | H | F | F | F | Bond | $n-C_4H_9$ |
| 1022 | $n-C_3H_7$ | H | F | F | F | Bond | $n-C_5H_{11}$ |
| 1023 | $n-C_3H_7$ | H | F | F | F | Bond | $n-C_6H_{13}$ |
| 1024 | $n-C_3H_7$ | H | F | F | F | Bond | $n-C_7H_{15}$ |
| 1025 | $n-C_3H_7$ | F | F | F | F | Bond | $CH_3$ |
| 1026 | $n-C_3H_7$ | F | F | F | F | Bond | $C_2H_5$ |
| 1027 | $n-C_3H_7$ | F | F | F | F | Bond | $n-C_3H_7$ |
| 1028 | $n-C_3H_7$ | F | F | F | F | Bond | $n-C_4H_9$ |
| 1029 | $n-C_3H_7$ | F | F | F | F | Bond | $n-C_5H_{11}$ |
| 1030 | $n-C_3H_7$ | F | F | F | F | Bond | $n-C_6H_{13}$ |
| 1031 | $n-C_3H_7$ | F | F | F | F | Bond | $n-C_7H_{15}$ |
| 1032 | $n-C_4H_9$ | H | H | F | F | Bond | $CH_3$ |
| 1033 | $n-C_4H_9$ | H | H | F | F | Bond | $C_2H_5$ |
| 1034 | $n-C_4H_9$ | H | H | F | F | Bond | $n-C_3H_7$ |
| 1035 | $n-C_4H_9$ | H | H | F | F | Bond | $n-C_4H_9$ |
| 1036 | $n-C_4H_9$ | H | H | F | F | Bond | $n-C_5H_{11}$ |
| 1037 | $n-C_4H_9$ | H | H | F | F | Bond | $n-C_6H_{13}$ |
| 1038 | $n-C_4H_9$ | H | H | F | F | Bond | $n-C_7H_{15}$ |
| 1039 | $n-C_4H_9$ | F | F | F | F | Bond | $CH_3$ |
| 1040 | $n-C_4H_9$ | F | F | F | F | Bond | $C_2H_5$ |
| 1041 | $n-C_4H_9$ | F | F | F | F | Bond | $n-C_3H_7$ |
| 1042 | $n-C_4H_9$ | F | F | F | F | Bond | $n-C_4H_9$ |
| 1043 | $n-C_4H_9$ | F | F | F | F | Bond | $n-C_5H_{11}$ |
| 1044 | $n-C_4H_9$ | F | F | F | F | Bond | $n-C_6H_{13}$ |
| 1045 | $n-C_4H_9$ | F | F | F | F | Bond | $n-C_7H_{15}$ |
| 1046 | $n-C_5H_{11}$ | H | H | F | F | Bond | $CH_3$ |
| 1047 | $n-C_5H_{11}$ | H | H | F | F | Bond | $C_2H_5$ |
| 1048 | $n-C_5H_{11}$ | H | H | F | F | Bond | $n-C_3H_7$ |
| 1049 | $n-C_5H_{11}$ | H | H | F | F | Bond | $n-C_4H_9$ |
| 1050 | $n-C_5H_{11}$ | H | H | F | F | Bond | $n-C_5H_{11}$ |
| 1051 | $n-C_5H_{11}$ | H | H | F | F | Bond | $n-C_6H_{13}$ |
| 1052 | $n-C_5H_{11}$ | H | H | F | F | Bond | $n-C_7H_{15}$ |
| 1053 | $n-C_5H_{11}$ | F | F | F | F | Bond | $CH_3$ |
| 1054 | $n-C_5H_{11}$ | F | F | F | F | Bond | $C_2H_5$ |
| 1055 | $n-C_5H_{11}$ | F | F | F | F | Bond | $n-C_3H_7$ |
| 1056 | $n-C_5H_{11}$ | F | F | F | F | Bond | $n-C_4H_9$ |
| 1057 | $n-C_5H_{11}$ | F | F | F | F | Bond | $n-C_5H_{11}$ |
| 1058 | $n-C_5H_{11}$ | F | F | F | F | Bond | $n-C_6H_{13}$ |
| 1059 | $n-C_5H_{11}$ | F | F | F | F | Bond | $n-C_7H_{15}$ |

Examples 1060-1206

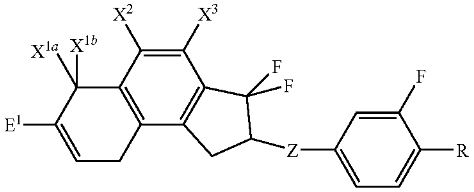

| Example | $E^1$ | $X^{1a}$ | $X^{1b}$ | $X^2$ | $X^3$ | Z | R |
|---|---|---|---|---|---|---|---|
| 1060 | H | H | H | H | F | Bond | $CH_3$ |
| 1061 | H | H | H | H | F | Bond | $C_2H_5$ |
| 1062 | H | H | H | H | F | Bond | $n-C_3H_7$ |
| 1063 | H | H | H | H | F | Bond | $n-C_4H_9$ |
| 1064 | H | H | H | H | F | Bond | $n-C_5H_{11}$ |
| 1065 | H | H | H | H | F | Bond | $n-C_6H_{13}$ |
| 1066 | H | H | H | H | F | Bond | $n-C_7H_{15}$ |
| 1067 | H | H | H | F | F | Bond | $CH_3$ |
| 1068 | H | H | H | F | F | Bond | $C_2H_5$ |
| 1069 | H | H | H | F | F | Bond | $n-C_3H_7$ |
| 1070 | H | H | H | F | F | Bond | $n-C_4H_9$ |
| 1071 | H | H | H | F | F | Bond | $n-C_5H_{11}$ |
| 1072 | H | H | H | F | F | Bond | $n-C_6H_{13}$ |
| 1073 | H | H | H | F | F | Bond | $n-C_7H_{15}$ |
| 1074 | H | H | F | F | F | Bond | $CH_3$ |
| 1075 | H | H | F | F | F | Bond | $C_2H_5$ |
| 1076 | H | H | F | F | F | Bond | $n-C_3H_7$ |
| 1077 | H | H | F | F | F | Bond | $n-C_4H_9$ |
| 1078 | H | H | F | F | F | Bond | $n-C_5H_{11}$ |
| 1079 | H | H | F | F | F | Bond | $n-C_6H_{13}$ |
| 1080 | H | H | F | F | F | Bond | $n-C_7H_{15}$ |
| 1081 | H | F | F | F | F | Bond | $CH_3$ |
| 1082 | H | F | F | F | F | Bond | $C_2H_5$ |
| 1083 | H | F | F | F | F | Bond | $n-C_3H_7$ |
| 1084 | H | F | F | F | F | Bond | $n-C_4H_9$ |
| 1085 | H | F | F | F | F | Bond | $n-C_5H_{11}$ |
| 1086 | H | F | F | F | F | Bond | $n-C_6H_{13}$ |
| 1087 | H | F | F | F | F | Bond | $n-C_7H_{15}$ |
| 1088 | H | H | F | F | F | $CF_2CF_2$ | $CH_3$ |
| 1089 | H | H | F | F | F | $CF_2CF_2$ | $C_2H_5$ |
| 1090 | H | H | F | F | F | $CF_2CF_2$ | $n-C_3H_7$ |
| 1091 | H | H | F | F | F | $CF_2CF_2$ | $n-C_4H_9$ |
| 1092 | H | H | F | F | F | $CF_2CF_2$ | $n-C_5H_{11}$ |
| 1093 | H | H | F | F | F | $CF_2CF_2$ | $n-C_6H_{13}$ |
| 1094 | H | H | F | F | F | $CF_2CF_2$ | $n-C_7H_{15}$ |
| 1095 | H | F | F | F | F | $CF_2CF_2$ | $CH_3$ |
| 1096 | H | F | F | F | F | $CF_2CF_2$ | $C_2H_5$ |
| 1097 | H | F | F | F | F | $CF_2CF_2$ | $n-C_3H_7$ |
| 1098 | H | F | F | F | F | $CF_2CF_2$ | $n-C_4H_9$ |
| 1099 | H | F | F | F | F | $CF_2CF_2$ | $n-C_5H_{11}$ |
| 1100 | H | F | F | F | F | $CF_2CF_2$ | $n-C_6H_{13}$ |
| 1101 | H | F | F | F | F | $CF_2CF_2$ | $n-C_7H_{15}$ |
| 1102 | H | F | F | F | F | $CF_2O$ | $CH_3$ |
| 1103 | H | F | F | F | F | $CF_2O$ | $C_2H_5$ |
| 1104 | H | F | F | F | F | $CF_2O$ | $n-C_3H_7$ |
| 1105 | H | F | F | F | F | $CF_2O$ | $n-C_4H_9$ |
| 1106 | H | F | F | F | F | $CF_2O$ | $n-C_5H_{11}$ |
| 1107 | H | F | F | F | F | $CF_2O$ | $n-C_6H_{13}$ |
| 1108 | H | F | F | F | F | $CF_2O$ | $n-C_7H_{15}$ |
| 1109 | $CH_3$ | H | H | F | F | Bond | $CH_3$ |
| 1110 | $CH_3$ | H | H | F | F | Bond | $C_2H_5$ |
| 1111 | $CH_3$ | H | H | F | F | Bond | $n-C_3H_7$ |
| 1112 | $CH_3$ | H | H | F | F | Bond | $n-C_4H_9$ |
| 1113 | $CH_3$ | H | H | F | F | Bond | $n-C_5H_{11}$ |
| 1114 | $CH_3$ | H | H | F | F | Bond | $n-C_6H_{13}$ |
| 1115 | $CH_3$ | H | H | F | F | Bond | $n-C_7H_{15}$ |
| 1116 | $CH_3$ | H | F | F | F | Bond | $CH_3$ |
| 1117 | $CH_3$ | H | F | F | F | Bond | $C_2H_5$ |
| 1118 | $CH_3$ | H | F | F | F | Bond | $n-C_3H_7$ |
| 1119 | $CH_3$ | H | F | F | F | Bond | $n-C_4H_9$ |
| 1120 | $CH_3$ | H | F | F | F | Bond | $n-C_5H_{11}$ |
| 1121 | $CH_3$ | H | F | F | F | Bond | $n-C_6H_{13}$ |
| 1122 | $CH_3$ | H | F | F | F | Bond | $n-C_7H_{15}$ |
| 1123 | $CH_3$ | F | F | F | F | Bond | $CH_3$ |

-continued

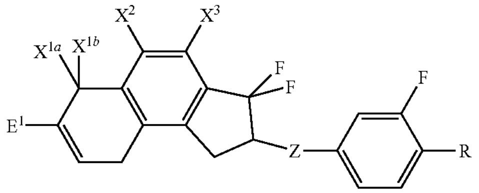

| Example | $E^1$ | $X^{1a}$ | $X^{1b}$ | $X^2$ | $X^3$ | Z | R |
|---|---|---|---|---|---|---|---|
| 1124 | $CH_3$ | F | F | F | F | Bond | $C_2H_5$ |
| 1125 | $CH_3$ | F | F | F | F | Bond | n-$C_3H_7$ |
| 1126 | $CH_3$ | F | F | F | F | Bond | n-$C_4H_9$ |
| 1127 | $CH_3$ | F | F | F | F | Bond | n-$C_5H_{11}$ |
| 1128 | $CH_3$ | F | F | F | F | Bond | n-$C_6H_{13}$ |
| 1129 | $CH_3$ | F | F | F | F | Bond | n-$C_7H_{15}$ |
| 1130 | $CH_3$ | F | F | F | F | $CF_2CF_2$ | $CH_3$ |
| 1131 | $CH_3$ | F | F | F | F | $CF_2CF_2$ | $C_2H_5$ |
| 1132 | $CH_3$ | F | F | F | F | $CF_2CF_2$ | n-$C_3H_7$ |
| 1133 | $CH_3$ | F | F | F | F | $CF_2CF_2$ | n-$C_4H_9$ |
| 1134 | $CH_3$ | F | F | F | F | $CF_2CF_2$ | n-$C_5H_{11}$ |
| 1135 | $CH_3$ | F | F | F | F | $CF_2CF_2$ | n-$C_6H_{13}$ |
| 1136 | $CH_3$ | F | F | F | F | $CF_2CF_2$ | n-$C_7H_{15}$ |
| 1137 | $CH_3$ | F | F | F | F | $CF_2O$ | $CH_3$ |
| 1138 | $CH_3$ | F | F | F | F | $CF_2O$ | $C_2H_5$ |
| 1139 | $CH_3$ | F | F | F | F | $CF_2O$ | n-$C_3H_7$ |
| 1140 | $CH_3$ | F | F | F | F | $CF_2O$ | n-$C_4H_9$ |
| 1141 | $CH_3$ | F | F | F | F | $CF_2O$ | n-$C_5H_{11}$ |
| 1142 | $CH_3$ | F | F | F | F | $CF_2O$ | n-$C_6H_{13}$ |
| 1143 | $CH_3$ | F | F | F | F | $CF_2O$ | n-$C_7H_{15}$ |
| 1144 | $C_2H_5$ | H | H | F | F | Bond | $CH_3$ |
| 1145 | $C_2H_5$ | H | H | F | F | Bond | $C_2H_5$ |
| 1146 | $C_2H_5$ | H | H | F | F | Bond | n-$C_3H_7$ |
| 1147 | $C_2H_5$ | H | H | F | F | Bond | n-$C_4H_9$ |
| 1148 | $C_2H_5$ | H | H | F | F | Bond | n-$C_5H_{11}$ |
| 1149 | $C_2H_5$ | H | H | F | F | Bond | n-$C_6H_{13}$ |
| 1150 | $C_2H_5$ | H | H | F | F | Bond | n-$C_7H_{15}$ |
| 1151 | $C_2H_5$ | F | F | F | F | Bond | $CH_3$ |
| 1152 | $C_2H_5$ | F | F | F | F | Bond | $C_2H_5$ |
| 1153 | $C_2H_5$ | F | F | F | F | Bond | n-$C_3H_7$ |
| 1154 | $C_2H_5$ | F | F | F | F | Bond | n-$C_4H_9$ |
| 1155 | $C_2H_5$ | F | F | F | F | Bond | n-$C_5H_{11}$ |
| 1156 | $C_2H_5$ | F | F | F | F | Bond | n-$C_6H_{13}$ |
| 1157 | $C_2H_5$ | F | F | F | F | Bond | n-$C_7H_{15}$ |
| 1158 | n-$C_3H_7$ | H | H | F | F | Bond | $CH_3$ |
| 1159 | n-$C_3H_7$ | H | H | F | F | Bond | $C_2H_5$ |
| 1160 | n-$C_3H_7$ | H | H | F | F | Bond | n-$C_3H_7$ |
| 1161 | n-$C_3H_7$ | H | H | F | F | Bond | n-$C_4H_9$ |
| 1162 | n-$C_3H_7$ | H | H | F | F | Bond | n-$C_5H_{11}$ |
| 1163 | n-$C_3H_7$ | H | H | F | F | Bond | n-$C_6H_{13}$ |
| 1164 | n-$C_3H_7$ | H | H | F | F | Bond | n-$C_7H_{15}$ |
| 1165 | n-$C_3H_7$ | H | F | F | F | Bond | $CH_3$ |
| 1166 | n-$C_3H_7$ | H | F | F | F | Bond | $C_2H_5$ |
| 1167 | n-$C_3H_7$ | H | F | F | F | Bond | n-$C_3H_7$ |
| 1168 | n-$C_3H_7$ | H | F | F | F | Bond | n-$C_4H_9$ |
| 1169 | n-$C_3H_7$ | H | F | F | F | Bond | n-$C_5H_{11}$ |
| 1170 | n-$C_3H_7$ | H | F | F | F | Bond | n-$C_6H_{13}$ |
| 1171 | n-$C_3H_7$ | H | F | F | F | Bond | n-$C_7H_{15}$ |
| 1172 | n-$C_3H_7$ | F | F | F | F | Bond | $CH_3$ |
| 1173 | n-$C_3H_7$ | F | F | F | F | Bond | $C_2H_5$ |
| 1174 | n-$C_3H_7$ | F | F | F | F | Bond | n-$C_3H_7$ |
| 1175 | n-$C_3H_7$ | F | F | F | F | Bond | n-$C_4H_9$ |
| 1176 | n-$C_3H_7$ | F | F | F | F | Bond | n-$C_5H_{11}$ |
| 1177 | n-$C_3H_7$ | F | F | F | F | Bond | n-$C_6H_{13}$ |
| 1178 | n-$C_3H_7$ | F | F | F | F | Bond | n-$C_7H_{15}$ |
| 1179 | n-$C_4H_9$ | H | H | F | F | Bond | $CH_3$ |
| 1180 | n-$C_4H_9$ | H | H | F | F | Bond | $C_2H_5$ |
| 1181 | n-$C_4H_9$ | H | H | F | F | Bond | n-$C_3H_7$ |
| 1182 | n-$C_4H_9$ | H | H | F | F | Bond | n-$C_4H_9$ |
| 1183 | n-$C_4H_9$ | H | H | F | F | Bond | n-$C_5H_{11}$ |
| 1184 | n-$C_4H_9$ | H | H | F | F | Bond | n-$C_6H_{13}$ |
| 1185 | n-$C_4H_9$ | H | H | F | F | Bond | n-$C_7H_{15}$ |
| 1186 | n-$C_4H_9$ | F | F | F | F | Bond | $CH_3$ |
| 1187 | n-$C_4H_9$ | F | F | F | F | Bond | $C_2H_5$ |
| 1188 | n-$C_4H_9$ | F | F | F | F | Bond | n-$C_3H_7$ |
| 1189 | n-$C_4H_9$ | F | F | F | F | Bond | n-$C_4H_9$ |
| 1190 | n-$C_4H_9$ | F | F | F | F | Bond | n-$C_5H_{11}$ |

-continued

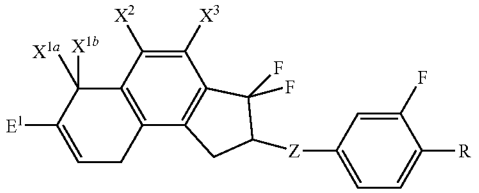

| Example | $E^1$ | $X^{1a}$ | $X^{1b}$ | $X^2$ | $X^3$ | Z | R |
|---|---|---|---|---|---|---|---|
| 1191 | n-$C_4H_9$ | F | F | F | F | Bond | n-$C_6H_{13}$ |
| 1192 | n-$C_4H_9$ | F | F | F | F | Bond | n-$C_7H_{15}$ |
| 1193 | n-$C_5H_{11}$ | H | H | F | F | Bond | $CH_3$ |
| 1194 | n-$C_5H_{11}$ | H | H | F | F | Bond | $C_2H_5$ |
| 1195 | n-$C_5H_{11}$ | H | H | F | F | Bond | n-$C_3H_7$ |
| 1196 | n-$C_5H_{11}$ | H | H | F | F | Bond | n-$C_4H_9$ |
| 1197 | n-$C_5H_{11}$ | H | H | F | F | Bond | n-$C_5H_{11}$ |
| 1198 | n-$C_5H_{11}$ | H | H | F | F | Bond | n-$C_6H_{13}$ |
| 1199 | n-$C_5H_{11}$ | H | H | F | F | Bond | n-$C_7H_{15}$ |
| 1200 | n-$C_5H_{11}$ | F | F | F | F | Bond | $CH_3$ |
| 1201 | n-$C_5H_{11}$ | F | F | F | F | Bond | $C_2H_5$ |
| 1202 | n-$C_5H_{11}$ | F | F | F | F | Bond | n-$C_3H_7$ |
| 1203 | n-$C_5H_{11}$ | F | F | F | F | Bond | n-$C_4H_9$ |
| 1204 | n-$C_5H_{11}$ | F | F | F | F | Bond | n-$C_5H_{11}$ |
| 1205 | n-$C_5H_{11}$ | F | F | F | F | Bond | n-$C_6H_{13}$ |
| 1206 | n-$C_5H_{11}$ | F | F | F | F | Bond | n-$C_7H_{15}$ |

Examples 1207-1304

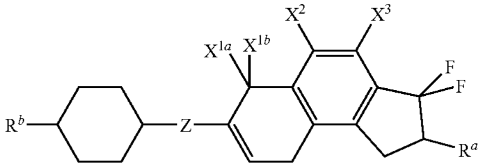

| Example | $R^b$ | $X^{1a}$ | $X^{1b}$ | $X^2$ | $X^3$ | Z | R |
|---|---|---|---|---|---|---|---|
| 1207 | $CH_3$ | H | H | F | F | Bond | $CH_3$ |
| 1208 | $CH_3$ | H | H | F | F | Bond | $C_2H_5$ |
| 1209 | $CH_3$ | H | H | F | F | Bond | n-$C_3H_7$ |
| 1210 | $CH_3$ | H | H | F | F | Bond | n-$C_4H_9$ |
| 1211 | $CH_3$ | H | H | F | F | Bond | n-$C_5H_{11}$ |
| 1212 | $CH_3$ | H | H | F | F | Bond | n-$C_6H_{13}$ |
| 1213 | $CH_3$ | H | H | F | F | Bond | n-$C_7H_{15}$ |
| 1214 | $CH_3$ | H | F | F | F | Bond | $CH_3$ |
| 1215 | $CH_3$ | H | F | F | F | Bond | $C_2H_5$ |
| 1216 | $CH_3$ | H | F | F | F | Bond | n-$C_3H_7$ |
| 1217 | $CH_3$ | H | F | F | F | Bond | n-$C_4H_9$ |
| 1218 | $CH_3$ | H | F | F | F | Bond | n-$C_5H_{11}$ |
| 1219 | $CH_3$ | H | F | F | F | Bond | n-$C_6H_{13}$ |
| 1220 | $CH_3$ | H | F | F | F | Bond | n-$C_7H_{15}$ |
| 1221 | $CH_3$ | F | F | F | F | Bond | $CH_3$ |
| 1222 | $CH_3$ | F | F | F | F | Bond | $C_2H_5$ |
| 1223 | $CH_3$ | F | F | F | F | Bond | n-$C_3H_7$ |
| 1224 | $CH_3$ | F | F | F | F | Bond | n-$C_4H_9$ |
| 1225 | $CH_3$ | F | F | F | F | Bond | n-$C_5H_{11}$ |
| 1226 | $CH_3$ | F | F | F | F | Bond | n-$C_6H_{13}$ |
| 1227 | $CH_3$ | F | F | F | F | Bond | n-$C_7H_{15}$ |
| 1228 | $CH_3$ | H | F | F | F | $CF_2CF_2$ | $CH_3$ |
| 1229 | $CH_3$ | H | F | F | F | $CF_2CF_2$ | $C_2H_5$ |
| 1230 | $CH_3$ | H | F | F | F | $CF_2CF_2$ | n-$C_3H_7$ |
| 1231 | $CH_3$ | H | F | F | F | $CF_2CF_2$ | n-$C_4H_9$ |
| 1232 | $CH_3$ | H | F | F | F | $CF_2CF_2$ | n-$C_5H_{11}$ |
| 1233 | $CH_3$ | H | F | F | F | $CF_2CF_2$ | n-$C_6H_{13}$ |
| 1234 | $CH_3$ | H | F | F | F | $CF_2CF_2$ | n-$C_7H_{15}$ |
| 1235 | $CH_3$ | F | F | F | F | $CF_2CF_2$ | $CH_3$ |
| 1236 | $CH_3$ | F | F | F | F | $CF_2CF_2$ | $C_2H_5$ |
| 1237 | $CH_3$ | F | F | F | F | $CF_2CF_2$ | n-$C_3H_7$ |

-continued

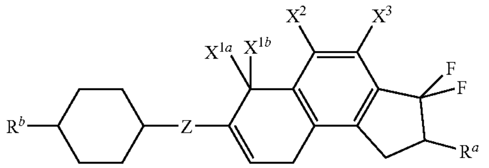

| Example | $R^b$ | $X^{1a}$ | $X^{1b}$ | $X^2$ | $X^3$ | Z | R |
|---|---|---|---|---|---|---|---|
| 1238 | $CH_3$ | F | F | F | F | $CF_2CF_2$ | n-$C_4H_9$ |
| 1239 | $CH_3$ | F | F | F | F | $CF_2CF_2$ | n-$C_5H_{11}$ |
| 1240 | $CH_3$ | F | F | F | F | $CF_2CF_2$ | n-$C_6H_{13}$ |
| 1241 | $CH_3$ | F | F | F | F | $CF_2CF_2$ | n-$C_7H_{15}$ |
| 1242 | $C_2H_5$ | H | H | F | F | Bond | $CH_3$ |
| 1243 | $C_2H_5$ | H | H | F | F | Bond | $C_2H_5$ |
| 1244 | $C_2H_5$ | H | H | F | F | Bond | n-$C_3H_7$ |
| 1245 | $C_2H_5$ | H | H | F | F | Bond | n-$C_4H_9$ |
| 1246 | $C_2H_5$ | H | H | F | F | Bond | n-$C_5H_{11}$ |
| 1247 | $C_2H_5$ | H | H | F | F | Bond | n-$C_6H_{13}$ |
| 1248 | $C_2H_5$ | H | H | F | F | Bond | n-$C_7H_{15}$ |
| 1249 | $C_2H_5$ | F | F | F | F | $CF_2CF_2$ | $CH_3$ |
| 1250 | $C_2H_5$ | F | F | F | F | $CF_2CF_2$ | $C_2H_5$ |
| 1251 | $C_2H_5$ | F | F | F | F | $CF_2CF_2$ | n-$C_3H_7$ |
| 1252 | $C_2H_5$ | F | F | F | F | $CF_2CF_2$ | n-$C_4H_9$ |
| 1253 | $C_2H_5$ | F | F | F | F | $CF_2CF_2$ | n-$C_5H_{11}$ |
| 1254 | $C_2H_5$ | F | F | F | F | $CF_2CF_2$ | n-$C_6H_{13}$ |
| 1255 | $C_2H_5$ | F | F | F | F | $CF_2CF_2$ | n-$C_7H_{15}$ |
| 1256 | $C_2H_5$ | F | F | F | F | Bond | $CH_3$ |
| 1257 | $C_2H_5$ | F | F | F | F | Bond | $C_2H_5$ |
| 1258 | $C_2H_5$ | F | F | F | F | Bond | n-$C_3H_7$ |
| 1259 | $C_2H_5$ | F | F | F | F | Bond | n-$C_4H_9$ |
| 1260 | $C_2H_5$ | F | F | F | F | Bond | n-$C_5H_{11}$ |
| 1261 | $C_2H_5$ | F | F | F | F | Bond | n-$C_6H_{13}$ |
| 1262 | $C_2H_5$ | F | F | F | F | Bond | n-$C_7H_{15}$ |
| 1263 | n-$C_3H_7$ | H | H | F | F | Bond | $CH_3$ |
| 1264 | n-$C_3H_7$ | H | H | F | F | Bond | $C_2H_5$ |
| 1265 | n-$C_3H_7$ | H | H | F | F | Bond | n-$C_3H_7$ |
| 1266 | n-$C_3H_7$ | H | H | F | F | Bond | n-$C_4H_9$ |
| 1267 | n-$C_3H_7$ | H | H | F | F | Bond | n-$C_5H_{11}$ |
| 1268 | n-$C_3H_7$ | H | H | F | F | Bond | n-$C_6H_{13}$ |
| 1269 | n-$C_3H_7$ | H | H | F | F | Bond | n-$C_7H_{15}$ |
| 1270 | n-$C_3H_7$ | F | F | F | F | Bond | $CH_3$ |
| 1271 | n-$C_3H_7$ | F | F | F | F | Bond | $C_2H_5$ |
| 1272 | n-$C_3H_7$ | F | F | F | F | Bond | n-$C_3H_7$ |
| 1273 | n-$C_3H_7$ | F | F | F | F | Bond | n-$C_4H_9$ |
| 1274 | n-$C_3H_7$ | F | F | F | F | Bond | n-$C_5H_{11}$ |
| 1275 | n-$C_3H_7$ | F | F | F | F | Bond | n-$C_6H_{13}$ |
| 1276 | n-$C_3H_7$ | F | F | F | F | Bond | n-$C_7H_{15}$ |
| 1277 | n-$C_4H_9$ | H | H | F | F | Bond | $CH_3$ |
| 1278 | n-$C_4H_9$ | H | H | F | F | Bond | $C_2H_5$ |
| 1279 | n-$C_4H_9$ | H | H | F | F | Bond | n-$C_3H_7$ |
| 1280 | n-$C_4H_9$ | H | H | F | F | Bond | n-$C_4H_9$ |
| 1281 | n-$C_4H_9$ | H | H | F | F | Bond | n-$C_5H_{11}$ |
| 1282 | n-$C_4H_9$ | H | H | F | F | Bond | n-$C_6H_{13}$ |
| 1283 | n-$C_4H_9$ | H | H | F | F | Bond | n-$C_7H_{15}$ |
| 1284 | n-$C_4H_9$ | F | F | F | F | Bond | $CH_3$ |
| 1285 | n-$C_4H_9$ | F | F | F | F | Bond | $C_2H_5$ |
| 1286 | n-$C_4H_9$ | F | F | F | F | Bond | n-$C_3H_7$ |
| 1287 | n-$C_4H_9$ | F | F | F | F | Bond | n-$C_4H_9$ |
| 1288 | n-$C_4H_9$ | F | F | F | F | Bond | n-$C_5H_{11}$ |
| 1289 | n-$C_4H_9$ | F | F | F | F | Bond | n-$C_6H_{13}$ |
| 1290 | n-$C_4H_9$ | F | F | F | F | Bond | n-$C_7H_{15}$ |
| 1291 | n-$C_5H_{11}$ | H | H | F | F | Bond | $CH_3$ |
| 1292 | n-$C_5H_{11}$ | H | H | F | F | Bond | $C_2H_5$ |
| 1293 | n-$C_5H_{11}$ | H | H | F | F | Bond | n-$C_3H_7$ |
| 1294 | n-$C_5H_{11}$ | H | H | F | F | Bond | n-$C_4H_9$ |
| 1295 | n-$C_5H_{11}$ | H | H | F | F | Bond | n-$C_5H_{11}$ |
| 1296 | n-$C_5H_{11}$ | H | H | F | F | Bond | n-$C_6H_{13}$ |
| 1297 | n-$C_5H_{11}$ | H | H | F | F | Bond | n-$C_7H_{15}$ |
| 1298 | n-$C_5H_{11}$ | F | F | F | F | Bond | $CH_3$ |
| 1299 | n-$C_5H_{11}$ | F | F | F | F | Bond | $C_2H_5$ |
| 1300 | n-$C_5H_{11}$ | F | F | F | F | Bond | n-$C_3H_7$ |
| 1301 | n-$C_5H_{11}$ | F | F | F | F | Bond | n-$C_4H_9$ |
| 1302 | n-$C_5H_{11}$ | F | F | F | F | Bond | n-$C_5H_{11}$ |
| 1303 | n-$C_5H_{11}$ | F | F | F | F | Bond | n-$C_6H_{13}$ |
| 1304 | n-$C_5H_{11}$ | F | F | F | F | Bond | n-$C_7H_{15}$ |

Examples 1305-1423

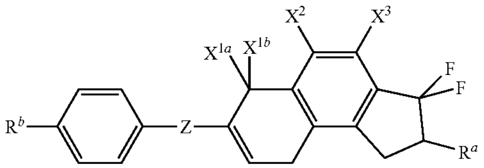

| Example | $R^b$ | $X^{1a}$ | $X^{1b}$ | $X^2$ | $X^3$ | Z | $R^a$ |
|---|---|---|---|---|---|---|---|
| 1305 | $CH_3$ | H | H | F | F | Bond | $CH_3$ |
| 1306 | $CH_3$ | H | H | F | F | Bond | $C_2H_5$ |
| 1307 | $CH_3$ | H | H | F | F | Bond | n-$C_3H_7$ |
| 1308 | $CH_3$ | H | H | F | F | Bond | n-$C_4H_9$ |
| 1309 | $CH_3$ | H | H | F | F | Bond | n-$C_5H_{11}$ |
| 1310 | $CH_3$ | H | H | F | F | Bond | n-$C_6H_{13}$ |
| 1311 | $CH_3$ | H | H | F | F | Bond | n-$C_7H_{15}$ |
| 1312 | $CH_3$ | H | F | F | F | Bond | $CH_3$ |
| 1313 | $CH_3$ | H | F | F | F | Bond | $C_2H_5$ |
| 1314 | $CH_3$ | H | F | F | F | Bond | n-$C_3H_7$ |
| 1315 | $CH_3$ | H | F | F | F | Bond | n-$C_4H_9$ |
| 1316 | $CH_3$ | H | F | F | F | Bond | n-$C_5H_{11}$ |
| 1317 | $CH_3$ | H | F | F | F | Bond | n-$C_6H_{13}$ |
| 1318 | $CH_3$ | H | F | F | F | Bond | n-$C_7H_{15}$ |
| 1319 | $CH_3$ | F | F | F | F | Bond | $CH_3$ |
| 1320 | $CH_3$ | F | F | F | F | Bond | $C_2H_5$ |
| 1321 | $CH_3$ | F | F | F | F | Bond | n-$C_3H_7$ |
| 1322 | $CH_3$ | F | F | F | F | Bond | n-$C_4H_9$ |
| 1323 | $CH_3$ | F | F | F | F | Bond | n-$C_5H_{11}$ |
| 1324 | $CH_3$ | F | F | F | F | Bond | n-$C_6H_{13}$ |
| 1325 | $CH_3$ | F | F | F | F | Bond | n-$C_7H_{15}$ |
| 1326 | $CH_3$ | H | F | F | F | $CF_2CF_2$ | $CH_3$ |
| 1327 | $CH_3$ | H | F | F | F | $CF_2CF_2$ | $C_2H_5$ |
| 1328 | $CH_3$ | H | F | F | F | $CF_2CF_2$ | n-$C_3H_7$ |
| 1329 | $CH_3$ | H | F | F | F | $CF_2CF_2$ | n-$C_4H_9$ |
| 1330 | $CH_3$ | H | F | F | F | $CF_2CF_2$ | n-$C_5H_{11}$ |
| 1331 | $CH_3$ | H | F | F | F | $CF_2CF_2$ | n-$C_6H_{13}$ |
| 1332 | $CH_3$ | H | F | F | F | $CF_2CF_2$ | n-$C_7H_{15}$ |
| 1333 | $CH_3$ | F | F | F | F | $CF_2CF_2$ | $CH_3$ |
| 1334 | $CH_3$ | F | F | F | F | $CF_2CF_2$ | $C_2H_5$ |
| 1335 | $CH_3$ | F | F | F | F | $CF_2CF_2$ | n-$C_3H_7$ |
| 1336 | $CH_3$ | F | F | F | F | $CF_2CF_2$ | n-$C_4H_9$ |
| 1337 | $CH_3$ | F | F | F | F | $CF_2CF_2$ | n-$C_5H_{11}$ |
| 1338 | $CH_3$ | F | F | F | F | $CF_2CF_2$ | n-$C_6H_{13}$ |
| 1339 | $CH_3$ | F | F | F | F | $CF_2CF_2$ | n-$C_7H_{15}$ |
| 1340 | $CH_3$ | H | F | F | F | $OCF_2$ | $CH_3$ |
| 1341 | $CH_3$ | H | F | F | F | $OCF_2$ | $C_2H_5$ |
| 1342 | $CH_3$ | H | F | F | F | $OCF_2$ | n-$C_3H_7$ |
| 1343 | $CH_3$ | H | F | F | F | $OCF_2$ | n-$C_4H_9$ |
| 1344 | $CH_3$ | H | F | F | F | $OCF_2$ | n-$C_5H_{11}$ |
| 1345 | $CH_3$ | H | F | F | F | $OCF_2$ | n-$C_6H_{13}$ |
| 1346 | $CH_3$ | H | F | F | F | $OCF_2$ | n-$C_7H_{15}$ |
| 1347 | $CH_3$ | F | F | F | F | $OCF_2$ | $CH_3$ |
| 1348 | $CH_3$ | F | F | F | F | $OCF_2$ | $C_2H_5$ |
| 1349 | $CH_3$ | F | F | F | F | $OCF_2$ | n-$C_3H_7$ |
| 1350 | $CH_3$ | F | F | F | F | $OCF_2$ | n-$C_4H_9$ |
| 1351 | $CH_3$ | F | F | F | F | $OCF_2$ | n-$C_5H_{11}$ |
| 1352 | $CH_3$ | F | F | F | F | $OCF_2$ | n-$C_6H_{13}$ |
| 1353 | $CH_3$ | F | F | F | F | $OCF_2$ | n-$C_7H_{15}$ |
| 1354 | $C_2H_5$ | H | H | F | F | Bond | $CH_3$ |
| 1355 | $C_2H_5$ | H | H | F | F | Bond | $C_2H_5$ |
| 1356 | $C_2H_5$ | H | H | F | F | Bond | n-$C_3H_7$ |
| 1357 | $C_2H_5$ | H | H | F | F | Bond | n-$C_4H_9$ |
| 1358 | $C_2H_5$ | H | H | F | F | Bond | n-$C_5H_{11}$ |
| 1359 | $C_2H_5$ | H | H | F | F | Bond | n-$C_6H_{13}$ |
| 1360 | $C_2H_5$ | H | H | F | F | Bond | n-$C_7H_{15}$ |
| 1361 | $C_2H_5$ | F | F | F | F | $CF_2CF_2$ | $CH_3$ |
| 1362 | $C_2H_5$ | F | F | F | F | $CF_2CF_2$ | $C_2H_5$ |
| 1363 | $C_2H_5$ | F | F | F | F | $CF_2CF_2$ | n-$C_3H_7$ |
| 1364 | $C_2H_5$ | F | F | F | F | $CF_2CF_2$ | n-$C_4H_9$ |
| 1365 | $C_2H_5$ | F | F | F | F | $CF_2CF_2$ | n-$C_5H_{11}$ |
| 1366 | $C_2H_5$ | F | F | F | F | $CF_2CF_2$ | n-$C_6H_{13}$ |
| 1367 | $C_2H_5$ | F | F | F | F | $CF_2CF_2$ | n-$C_7H_{15}$ |
| 1368 | $C_2H_5$ | F | F | F | F | $OCF_2$ | $CH_3$ |
| 1369 | $C_2H_5$ | F | F | F | F | $OCF_2$ | $C_2H_5$ |

-continued

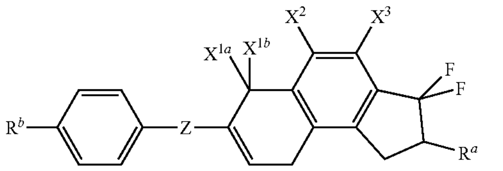

| Example | $R^b$ | $X^{1a}$ | $X^{1b}$ | $X^2$ | $X^3$ | Z | $R^a$ |
|---|---|---|---|---|---|---|---|
| 1370 | $C_2H_5$ | F | F | F | F | $OCF_2$ | $n\text{-}C_3H_7$ |
| 1371 | $C_2H_5$ | F | F | F | F | $OCF_2$ | $n\text{-}C_4H_9$ |
| 1372 | $C_2H_5$ | F | F | F | F | $OCF_2$ | $n\text{-}C_5H_{11}$ |
| 1373 | $C_2H_5$ | F | F | F | F | $OCF_2$ | $n\text{-}C_6H_{13}$ |
| 1374 | $C_2H_5$ | F | F | F | F | $OCF_2$ | $n\text{-}C_7H_{15}$ |
| 1375 | $C_2H_5$ | F | F | F | F | Bond | $CH_3$ |
| 1376 | $C_2H_5$ | F | F | F | F | Bond | $C_2H_5$ |
| 1377 | $C_2H_5$ | F | F | F | F | Bond | $n\text{-}C_3H_7$ |
| 1378 | $C_2H_5$ | F | F | F | F | Bond | $n\text{-}C_4H_9$ |
| 1379 | $C_2H_5$ | F | F | F | F | Bond | $n\text{-}C_5H_{11}$ |
| 1380 | $C_2H_5$ | F | F | F | F | Bond | $n\text{-}C_6H_{13}$ |
| 1381 | $C_2H_5$ | F | F | F | F | Bond | $n\text{-}C_7H_{15}$ |
| 1382 | $n\text{-}C_3H_7$ | H | H | F | F | Bond | $CH_3$ |
| 1383 | $n\text{-}C_3H_7$ | H | H | F | F | Bond | $C_2H_5$ |
| 1384 | $n\text{-}C_3H_7$ | H | H | F | F | Bond | $n\text{-}C_3H_7$ |
| 1385 | $n\text{-}C_3H_7$ | H | H | F | F | Bond | $n\text{-}C_4H_9$ |
| 1386 | $n\text{-}C_3H_7$ | H | H | F | F | Bond | $n\text{-}C_5H_{11}$ |
| 1387 | $n\text{-}C_3H_7$ | H | H | F | F | Bond | $n\text{-}C_6H_{13}$ |
| 1388 | $n\text{-}C_3H_7$ | H | H | F | F | Bond | $n\text{-}C_7H_{15}$ |
| 1389 | $n\text{-}C_3H_7$ | F | F | F | F | Bond | $CH_3$ |
| 1390 | $n\text{-}C_3H_7$ | F | F | F | F | Bond | $C_2H_5$ |
| 1391 | $n\text{-}C_3H_7$ | F | F | F | F | Bond | $n\text{-}C_3H_7$ |
| 1392 | $n\text{-}C_3H_7$ | F | F | F | F | Bond | $n\text{-}C_4H_9$ |
| 1393 | $n\text{-}C_3H_7$ | F | F | F | F | Bond | $n\text{-}C_5H_{11}$ |
| 1394 | $n\text{-}C_3H_7$ | F | F | F | F | Bond | $n\text{-}C_6H_{13}$ |
| 1395 | $n\text{-}C_3H_7$ | F | F | F | F | Bond | $n\text{-}C_7H_{15}$ |
| 1396 | $n\text{-}C_4H_9$ | H | H | F | F | Bond | $CH_3$ |
| 1397 | $n\text{-}C_4H_9$ | H | H | F | F | Bond | $C_2H_5$ |
| 1398 | $n\text{-}C_4H_9$ | H | H | F | F | Bond | $n\text{-}C_3H_7$ |
| 1399 | $n\text{-}C_4H_9$ | H | H | F | F | Bond | $n\text{-}C_4H_9$ |
| 1400 | $n\text{-}C_4H_9$ | H | H | F | F | Bond | $n\text{-}C_5H_{11}$ |
| 1401 | $n\text{-}C_4H_9$ | H | H | F | F | Bond | $n\text{-}C_6H_{13}$ |
| 1402 | $n\text{-}C_4H_9$ | H | H | F | F | Bond | $n\text{-}C_7H_{15}$ |
| 1403 | $n\text{-}C_4H_9$ | F | F | F | F | Bond | $CH_3$ |
| 1404 | $n\text{-}C_4H_9$ | F | F | F | F | Bond | $C_2H_5$ |
| 1405 | $n\text{-}C_4H_9$ | F | F | F | F | Bond | $n\text{-}C_3H_7$ |
| 1406 | $n\text{-}C_4H_9$ | F | F | F | F | Bond | $n\text{-}C_4H_9$ |
| 1407 | $n\text{-}C_4H_9$ | F | F | F | F | Bond | $n\text{-}C_5H_{11}$ |
| 1408 | $n\text{-}C_4H_9$ | F | F | F | F | Bond | $n\text{-}C_6H_{13}$ |
| 1409 | $n\text{-}C_4H_9$ | F | F | F | F | Bond | $n\text{-}C_7H_{15}$ |
| 1410 | $n\text{-}C_5H_{11}$ | H | H | F | F | Bond | $CH_3$ |
| 1411 | $n\text{-}C_5H_{11}$ | H | H | F | F | Bond | $C_2H_5$ |
| 1412 | $n\text{-}C_5H_{11}$ | H | H | F | F | Bond | $n\text{-}C_3H_7$ |
| 1413 | $n\text{-}C_5H_{11}$ | H | H | F | F | Bond | $n\text{-}C_4H_9$ |
| 1414 | $n\text{-}C_5H_{11}$ | H | H | F | F | Bond | $n\text{-}C_5H_{11}$ |
| 1415 | $n\text{-}C_5H_{11}$ | H | H | F | F | Bond | $n\text{-}C_6H_{13}$ |
| 1416 | $n\text{-}C_5H_{11}$ | H | H | F | F | Bond | $n\text{-}C_7H_{15}$ |
| 1417 | $n\text{-}C_5H_{11}$ | F | F | F | F | Bond | $CH_3$ |
| 1418 | $n\text{-}C_5H_{11}$ | F | F | F | F | Bond | $C_2H_5$ |
| 1419 | $n\text{-}C_5H_{11}$ | F | F | F | F | Bond | $n\text{-}C_3H_7$ |
| 1420 | $n\text{-}C_5H_{11}$ | F | F | F | F | Bond | $n\text{-}C_4H_9$ |
| 1421 | $n\text{-}C_5H_{11}$ | F | F | F | F | Bond | $n\text{-}C_5H_{11}$ |
| 1422 | $n\text{-}C_5H_{11}$ | F | F | F | F | Bond | $n\text{-}C_6H_{13}$ |
| 1423 | $n\text{-}C_5H_{11}$ | F | F | F | F | Bond | $n\text{-}C_7H_{15}$ |

Examples 1424-1507

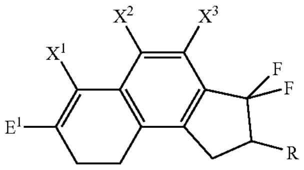

| Example | $E^1$ | $X^1$ | $X^2$ | $X^3$ | R |
|---|---|---|---|---|---|
| 1424 | H | H | F | F | $CH_3$ |
| 1425 | H | H | F | F | $C_2H_5$ |
| 1426 | H | H | F | F | $n\text{-}C_3H_7$ |
| 1427 | H | H | F | F | $n\text{-}C_4H_9$ |
| 1428 | H | H | F | F | $n\text{-}C_5H_{11}$ |
| 1429 | H | H | F | F | $n\text{-}C_6H_{13}$ |
| 1430 | H | H | F | F | $n\text{-}C_7H_{15}$ |
| 1431 | H | F | F | F | $CH_3$ |
| 1432 | H | F | F | F | $C_2H_5$ |
| 1433 | H | F | F | F | $n\text{-}C_3H_7$ |
| 1434 | H | F | F | F | $n\text{-}C_4H_9$ |
| 1435 | H | F | F | F | $n\text{-}C_5H_{11}$ |
| 1436 | H | F | F | F | $n\text{-}C_6H_{13}$ |
| 1437 | H | F | F | F | $n\text{-}C_7H_{15}$ |
| 1438 | $CH_3$ | H | F | F | $CH_3$ |
| 1439 | $CH_3$ | H | F | F | $C_2H_5$ |
| 1440 | $CH_3$ | H | F | F | $n\text{-}C_3H_7$ |
| 1441 | $CH_3$ | H | F | F | $n\text{-}C_4H_9$ |
| 1442 | $CH_3$ | H | F | F | n-O5H11 |
| 1443 | $CH_3$ | H | F | F | $n\text{-}C_6H_{13}$ |
| 1444 | $CH_3$ | H | F | F | $n\text{-}C_7H_{15}$ |
| 1445 | $CH_3$ | F | F | F | $CH_3$ |
| 1446 | $CH_3$ | F | F | F | $C_2H_5$ |
| 1447 | $CH_3$ | F | F | F | $n\text{-}C_3H_7$ |
| 1448 | $CH_3$ | F | F | F | $n\text{-}C_4H_9$ |
| 1449 | $CH_3$ | F | F | F | $n\text{-}C_5H_{11}$ |
| 1450 | $CH_3$ | F | F | F | $n\text{-}C_6H_{13}$ |
| 1451 | $CH_3$ | F | F | F | $n\text{-}C_7H_{15}$ |
| 1452 | $C_2H_5$ | H | F | F | $CH_3$ |
| 1453 | $C_2H_5$ | H | F | F | $C_2H_5$ |
| 1454 | $C_2H_5$ | H | F | F | $n\text{-}C_3H_7$ |
| 1455 | $C_2H_5$ | H | F | F | $n\text{-}C_4H_9$ |
| 1456 | $C_2H_5$ | H | F | F | $n\text{-}C_5H_{11}$ |
| 1457 | $C_2H_5$ | H | F | F | $n\text{-}C_6H_{13}$ |
| 1458 | $C_2H_5$ | H | F | F | $n\text{-}C_7H_{15}$ |
| 1459 | $C_2H_5$ | F | F | F | $CH_3$ |
| 1460 | $C_2H_5$ | F | F | F | $C_2H_5$ |
| 1461 | $C_2H_5$ | F | F | F | $n\text{-}C_3H_7$ |
| 1462 | $C_2H_5$ | F | F | F | $n\text{-}C_4H_9$ |
| 1463 | $C_2H_5$ | F | F | F | $n\text{-}C_5H_{11}$ |
| 1464 | $C_2H_5$ | F | F | F | $n\text{-}C_6H_{13}$ |
| 1465 | $C_2H_5$ | F | F | F | $n\text{-}C_7H_{15}$ |
| 1466 | $n\text{-}C_3H_7$ | H | F | F | $CH_3$ |
| 1467 | $n\text{-}C_3H_7$ | H | F | F | $C_2H_5$ |
| 1468 | $n\text{-}C_3H_7$ | H | F | F | $n\text{-}C_3H_7$ |
| 1469 | $n\text{-}C_3H_7$ | H | F | F | $n\text{-}C_4H_9$ |
| 1470 | $n\text{-}C_3H_7$ | H | F | F | $n\text{-}C_5H_{11}$ |
| 1471 | $n\text{-}C_3H_7$ | H | F | F | $n\text{-}C_6H_{13}$ |
| 1472 | $n\text{-}C_3H_7$ | H | F | F | $n\text{-}C_7H_{15}$ |
| 1473 | $n\text{-}C_3H_7$ | F | F | F | $CH_3$ |
| 1474 | $n\text{-}C_3H_7$ | F | F | F | $C_2H_5$ |
| 1475 | $n\text{-}C_3H_7$ | F | F | F | $n\text{-}C_3H_7$ |
| 1476 | $n\text{-}C_3H_7$ | F | F | F | $n\text{-}C_4H_9$ |
| 1477 | $n\text{-}C_3H_7$ | F | F | F | $n\text{-}C_5H_{11}$ |
| 1478 | $n\text{-}C_3H_7$ | F | F | F | $n\text{-}C_6H_{13}$ |
| 1479 | $n\text{-}C_3H_7$ | F | F | F | $n\text{-}C_7H_{15}$ |
| 1480 | $n\text{-}C_4H_9$ | H | F | F | $CH_3$ |
| 1481 | $n\text{-}C_4H_9$ | H | F | F | $C_2H_5$ |
| 1482 | $n\text{-}C_4H_9$ | H | F | F | $n\text{-}C_3H_7$ |
| 1483 | $n\text{-}C_4H_9$ | H | F | F | $n\text{-}C_4H_9$ |
| 1484 | $n\text{-}C_4H_9$ | H | F | F | $n\text{-}C_5H_{11}$ |
| 1485 | $n\text{-}C_4H_9$ | H | F | F | $n\text{-}C_6H_{13}$ |
| 1486 | $n\text{-}C_4H_9$ | H | F | F | $n\text{-}C_7H_{15}$ |
| 1487 | $n\text{-}C_4H_9$ | F | F | F | $CH_3$ |
| 1488 | $n\text{-}C_4H_9$ | F | F | F | $C_2H_5$ |

-continued

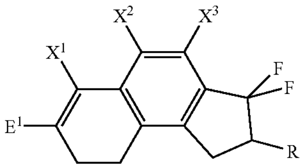

| Example | $E^1$ | $X^1$ | $X^2$ | $X^3$ | R |
|---|---|---|---|---|---|
| 1489 | n-$C_4H_9$ | F | F | F | n-$C_3H_7$ |
| 1490 | n-$C_4H_9$ | F | F | F | n-$C_4H_9$ |
| 1491 | n-$C_4H_9$ | F | F | F | n-$C_5H_{11}$ |
| 1492 | n-$C_4H_9$ | F | F | F | n-$C_6H_{13}$ |
| 1493 | n-$C_4H_9$ | F | F | F | n-$C_7H_{15}$ |
| 1494 | n-$C_5H_{11}$ | H | F | F | $CH_3$ |
| 1495 | n-$C_5H_{11}$ | H | F | F | $C_2H_5$ |
| 1496 | n-$C_5H_{11}$ | H | F | F | n-$C_3H_7$ |
| 1497 | n-$C_5H_{11}$ | H | F | F | n-$C_4H_9$ |
| 1498 | n-$C_5H_{11}$ | H | F | F | n-$C_5H_{11}$ |
| 1499 | n-$C_5H_{11}$ | H | F | F | n-$C_6H_{13}$ |
| 1500 | n-$C_5H_{11}$ | H | F | F | n-$C_7H_{15}$ |
| 1501 | n-$C_5H_{11}$ | F | F | F | $CH_3$ |
| 1502 | n-$C_5H_{11}$ | F | F | F | $C_2H_5$ |
| 1503 | n-$C_5H_{11}$ | F | F | F | n-$C_3H_7$ |
| 1504 | n-$C_5H_{11}$ | F | F | F | n-$C_4H_9$ |
| 1505 | n-$C_5H_{11}$ | F | F | F | n-$C_5H_{11}$ |
| 1506 | n-$C_5H_{11}$ | F | F | F | n-$C_6H_{13}$ |
| 1507 | n-$C_5H_{11}$ | F | F | F | n-$C_7H_{15}$ |

Examples 1508-1577

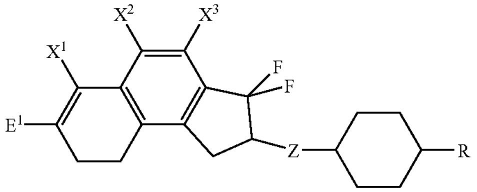

| Example | $E^1$ | $X^1$ | $X^2$ | $X^3$ | Z | R |
|---|---|---|---|---|---|---|
| 1508 | H | F | F | F | Bond | $CH_3$ |
| 1509 | H | F | F | F | Bond | $C_2H_5$ |
| 1510 | H | F | F | F | Bond | n-$C_3H_7$ |
| 1511 | H | F | F | F | Bond | n-$C_4H_9$ |
| 1512 | H | F | F | F | Bond | n-$C_5H_{11}$ |
| 1513 | H | F | F | F | Bond | n-$C_6H_{13}$ |
| 1514 | H | F | F | F | Bond | n-$C_7H_{15}$ |
| 1515 | H | F | F | F | $CF_2CF_2$ | $CH_3$ |
| 1516 | H | F | F | F | $CF_2CF_2$ | $C_2H_5$ |
| 1517 | H | F | F | F | $CF_2CF_2$ | n-$C_3H_7$ |
| 1518 | H | F | F | F | $CF_2CF_2$ | n-$C_4H_9$ |
| 1519 | H | F | F | F | $CF_2CF_2$ | n-$C_5H_{11}$ |
| 1520 | H | F | F | F | $CF_2CF_2$ | n-$C_6H_{13}$ |
| 1521 | H | F | F | F | $CF_2CF_2$ | n-$C_7H_{15}$ |
| 1522 | H | F | F | F | $OCF_2$ | $CH_3$ |
| 1523 | H | F | F | F | $OCF_2$ | $C_2H_5$ |
| 1524 | H | F | F | F | $OCF_2$ | n-$C_3H_7$ |
| 1525 | H | F | F | F | $OCF_2$ | n-$C_4H_9$ |
| 1526 | H | F | F | F | $OCF_2$ | n-$C_5H_{11}$ |
| 1527 | H | F | F | F | $OCF_2$ | n-$C_6H_{13}$ |
| 1528 | H | F | F | F | $OCF_2$ | n-$C_7H_{15}$ |
| 1529 | $CH_3$ | F | F | F | Bond | $CH_3$ |
| 1530 | $CH_3$ | F | F | F | Bond | $C_2H_5$ |
| 1531 | $CH_3$ | F | F | F | Bond | n-$C_3H_7$ |
| 1532 | $CH_3$ | F | F | F | Bond | n-$C_4H_9$ |
| 1533 | $CH_3$ | F | F | F | Bond | n-$C_5H_{11}$ |
| 1534 | $CH_3$ | F | F | F | Bond | n-$C_6H_{13}$ |
| 1535 | $CH_3$ | F | F | F | Bond | n-$C_7H_{15}$ |

-continued

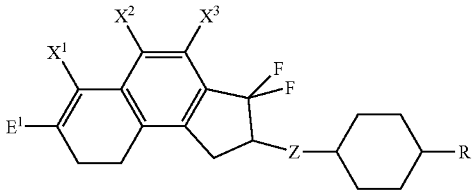

| Example | $E^1$ | $X^1$ | $X^2$ | $X^3$ | Z | R |
|---|---|---|---|---|---|---|
| 1536 | $CH_3$ | F | F | F | $CF_2CF_2$ | $CH_3$ |
| 1537 | $CH_3$ | F | F | F | $CF_2CF_2$ | $C_2H_5$ |
| 1538 | $CH_3$ | F | F | F | $CF_2CF_2$ | n-$C_3H_7$ |
| 1539 | $CH_3$ | F | F | F | $CF_2CF_2$ | n-$C_4H_9$ |
| 1540 | $CH_3$ | F | F | F | $CF_2CF_2$ | n-$C_5H_{11}$ |
| 1541 | $CH_3$ | F | F | F | $CF_2CF_2$ | n-$C_6H_{13}$ |
| 1542 | $CH_3$ | F | F | F | $CF_2CF_2$ | n-$C_7H_{15}$ |
| 1543 | $CH_3$ | F | F | F | $OCF_2$ | $CH_3$ |
| 1544 | $CH_3$ | F | F | F | $OCF_2$ | $C_2H_5$ |
| 1545 | $CH_3$ | F | F | F | $OCF_2$ | n-$C_3H_7$ |
| 1546 | $CH_3$ | F | F | F | $OCF_2$ | n-$C_4H_9$ |
| 1547 | $CH_3$ | F | F | F | $OCF_2$ | n-$C_5H_{11}$ |
| 1548 | $CH_3$ | F | F | F | $OCF_2$ | n-$C_6H_{13}$ |
| 1549 | $CH_3$ | F | F | F | $OCF_2$ | n-$C_7H_{15}$ |
| 1550 | $C_2H_5$ | F | F | F | Bond | $CH_3$ |
| 1551 | $C_2H_5$ | F | F | F | Bond | $C_2H_5$ |
| 1552 | $C_2H_5$ | F | F | F | Bond | n-$C_3H_7$ |
| 1553 | $C_2H_5$ | F | F | F | Bond | n-$C_4H_9$ |
| 1554 | $C_2H_5$ | F | F | F | Bond | n-$C_5H_{11}$ |
| 1555 | $C_2H_5$ | F | F | F | Bond | n-$C_6H_{13}$ |
| 1556 | $C_2H_5$ | F | F | F | Bond | n-$C_7H_{15}$ |
| 1557 | n-$C_3H_7$ | F | F | F | Bond | $CH_3$ |
| 1558 | n-$C_3H_7$ | F | F | F | Bond | $C_2H_5$ |
| 1559 | n-$C_3H_7$ | F | F | F | Bond | n-$C_3H_7$ |
| 1560 | n-$C_3H_7$ | F | F | F | Bond | n-$C_4H_9$ |
| 1561 | n-$C_3H_7$ | F | F | F | Bond | n-$C_5H_{11}$ |
| 1562 | n-$C_3H_7$ | F | F | F | Bond | n-$C_6H_{13}$ |
| 1563 | n-$C_3H_7$ | F | F | F | Bond | n-$C_7H_{15}$ |
| 1564 | n-$C_4H_9$ | F | F | F | Bond | $CH_3$ |
| 1565 | n-$C_4H_9$ | F | F | F | Bond | $C_2H_5$ |
| 1566 | n-$C_4H_9$ | F | F | F | Bond | n-$C_3H_7$ |
| 1567 | n-$C_4H_9$ | F | F | F | Bond | n-$C_4H_9$ |
| 1568 | n-$C_4H_9$ | F | F | F | Bond | n-$C_5H_{11}$ |
| 1569 | n-$C_4H_9$ | F | F | F | Bond | n-$C_6H_{13}$ |
| 1570 | n-$C_4H_9$ | F | F | F | Bond | n-$C_7H_{15}$ |
| 1571 | n-$C_4H_{11}$ | F | F | F | Bond | $CH_3$ |
| 1572 | n-$C_5H_{11}$ | F | F | F | Bond | $C_2H_5$ |
| 1573 | n-$C_5H_{11}$ | F | F | F | Bond | n-$C_3H_7$ |
| 1574 | n-$C_5H_{11}$ | F | F | F | Bond | n-$C_4H_9$ |
| 1575 | n-$C_5H_{11}$ | F | F | F | Bond | n-$C_5H_{11}$ |
| 1576 | n-$C_5H_{11}$ | F | F | F | Bond | n-$C_6H_{13}$ |
| 1577 | n-$C_5H_{11}$ | F | F | F | Bond | n-$C_7H_{15}$ |

Examples 1578-1647

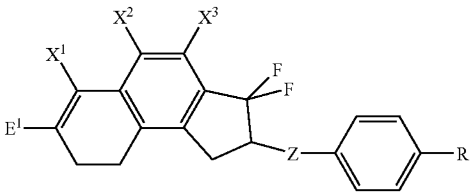

| Example | $E^1$ | $X^1$ | $X^2$ | $X^3$ | Z | R |
|---|---|---|---|---|---|---|
| 1578 | H | F | F | F | Bond | $CH_3$ |
| 1579 | H | F | F | F | Bond | $C_2H_5$ |
| 1580 | H | F | F | F | Bond | n-$C_3H_7$ |
| 1581 | H | F | F | F | Bond | n-$C_4H_9$ |

-continued

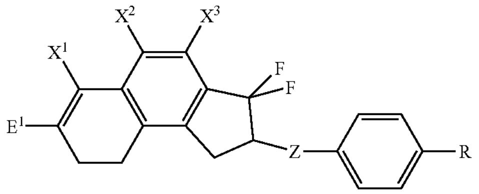

| Example | $E^1$ | $X^1$ | $X^2$ | $X^3$ | Z | R |
|---|---|---|---|---|---|---|
| 1582 | H | F | F | F | Bond | $n\text{-}C_5H_{11}$ |
| 1583 | H | F | F | F | Bond | $n\text{-}C_6H_{13}$ |
| 1584 | H | F | F | F | Bond | $n\text{-}C_7H_{15}$ |
| 1585 | H | F | F | F | $CF_2CF_2$ | $CH_3$ |
| 1586 | H | F | F | F | $CF_2CF_2$ | $C_2H_5$ |
| 1587 | H | F | F | F | $CF_2CF_2$ | $n\text{-}C_3H_7$ |
| 1588 | H | F | F | F | $CF_2CF_2$ | $n\text{-}C_4H_9$ |
| 1589 | H | F | F | F | $CF_2CF_2$ | $n\text{-}C_5H_{11}$ |
| 1590 | H | F | F | F | $CF_2CF_2$ | $n\text{-}C_6H_{13}$ |
| 1591 | H | F | F | F | $CF_2CF_2$ | $n\text{-}C_7H_{15}$ |
| 1592 | H | F | F | F | $CF_2O$ | $CH_3$ |
| 1593 | H | F | F | F | $CF_2O$ | $C_2H_5$ |
| 1594 | H | F | F | F | $CF_2O$ | $n\text{-}C_3H_7$ |
| 1595 | H | F | F | F | $CF_2O$ | $n\text{-}C_4H_9$ |
| 1596 | H | F | F | F | $CF_2O$ | $n\text{-}C_5H_{11}$ |
| 1597 | H | F | F | F | $CF_2O$ | $n\text{-}C_6H_{13}$ |
| 1598 | H | F | F | F | $CF_2O$ | $n\text{-}C_7H_{15}$ |
| 1599 | $CH_3$ | F | F | F | Bond | $CH_3$ |
| 1600 | $CH_3$ | F | F | F | Bond | $C_2H_5$ |
| 1601 | $CH_3$ | F | F | F | Bond | $n\text{-}C_3H_7$ |
| 1602 | $CH_3$ | F | F | F | Bond | $n\text{-}C_4H_9$ |
| 1603 | $CH_3$ | F | F | F | Bond | $n\text{-}C_5H_{11}$ |
| 1604 | $CH_3$ | F | F | F | Bond | $n\text{-}C_6H_{13}$ |
| 1605 | $CH_3$ | F | F | F | Bond | $n\text{-}C_7H_{15}$ |
| 1606 | $CH_3$ | F | F | F | $CF_2CF_2$ | $CH_3$ |
| 1607 | $CH_3$ | F | F | F | $CF_2CF_2$ | $C_2H_5$ |
| 1608 | $CH_3$ | F | F | F | $CF_2CF_2$ | $n\text{-}C_3H_7$ |
| 1609 | $CH_3$ | F | F | F | $CF_2CF_2$ | $n\text{-}C_4H_9$ |
| 1610 | $CH_3$ | F | F | F | $CF_2CF_2$ | $n\text{-}C_5H_{11}$ |
| 1611 | $CH_3$ | F | F | F | $CF_2CF_2$ | $n\text{-}C_6H_{13}$ |
| 1612 | $CH_3$ | F | F | F | $CF_2CF_2$ | $n\text{-}C_7H_{15}$ |
| 1613 | $CH_3$ | F | F | F | $CF_2O$ | $CH_3$ |
| 1614 | $CH_3$ | F | F | F | $CF_2O$ | $C_2H_5$ |
| 1615 | $CH_3$ | F | F | F | $CF_2O$ | $n\text{-}C_3H_7$ |
| 1616 | $CH_3$ | F | F | F | $CF_2O$ | $n\text{-}C_4H_9$ |
| 1617 | $CH_3$ | F | F | F | $CF_2O$ | $n\text{-}C_5H_{11}$ |
| 1618 | $CH_3$ | F | F | F | $CF_2O$ | $n\text{-}C_6H_{13}$ |
| 1619 | $CH_3$ | F | F | F | $CF_2O$ | $n\text{-}C_7H_{15}$ |
| 1620 | $C_2H_5$ | F | F | F | Bond | $CH_3$ |
| 1621 | $C_2H_5$ | F | F | F | Bond | $C_2H_5$ |
| 1622 | $C_2H_5$ | F | F | F | Bond | $n\text{-}C_3H_7$ |
| 1623 | $C_2H_5$ | F | F | F | Bond | $n\text{-}C_4H_9$ |
| 1624 | $C_2H_5$ | F | F | F | Bond | $n\text{-}C_5H_{11}$ |
| 1625 | $C_2H_5$ | F | F | F | Bond | $n\text{-}C_6H_{13}$ |
| 1626 | $C_2H_5$ | F | F | F | Bond | $n\text{-}C_7H_{15}$ |
| 1627 | $n\text{-}C_3H_7$ | F | F | F | Bond | $CH_3$ |
| 1628 | $n\text{-}C_3H_7$ | F | F | F | Bond | $C_2H_5$ |
| 1629 | $n\text{-}C_3H_7$ | F | F | F | Bond | $n\text{-}C_3H_7$ |
| 1630 | $n\text{-}C_3H_7$ | F | F | F | Bond | $n\text{-}C_4H_9$ |
| 1631 | $n\text{-}C_3H_7$ | F | F | F | Bond | $n\text{-}C_5H_{11}$ |
| 1632 | $n\text{-}C_3H_7$ | F | F | F | Bond | $n\text{-}C_6H_{13}$ |
| 1633 | $n\text{-}C_3H_7$ | F | F | F | Bond | $n\text{-}C_7H_{15}$ |
| 1634 | $n\text{-}C_4H_9$ | F | F | F | Bond | $CH_3$ |
| 1635 | $n\text{-}C_4H_9$ | F | F | F | Bond | $C_2H_5$ |
| 1636 | $n\text{-}C_4H_9$ | F | F | F | Bond | $n\text{-}C_3H_7$ |
| 1637 | $n\text{-}C_4H_9$ | F | F | F | Bond | $n\text{-}C_4H_9$ |
| 1638 | $n\text{-}C_4H_9$ | F | F | F | Bond | $n\text{-}C_5H_{11}$ |
| 1639 | $n\text{-}C_4H_9$ | F | F | F | Bond | $n\text{-}C_6H_{13}$ |
| 1640 | $n\text{-}C_4H_9$ | F | F | F | Bond | $n\text{-}C_7H_{15}$ |
| 1641 | $n\text{-}C_5H_{11}$ | F | F | F | Bond | $CH_3$ |
| 1642 | $n\text{-}C_5H_{11}$ | F | F | F | Bond | $C_2H_5$ |
| 1643 | $n\text{-}C_5H_{11}$ | F | F | F | Bond | $n\text{-}C_3H_7$ |
| 1644 | $n\text{-}C_5H_{11}$ | F | F | F | Bond | $n\text{-}C_4H_9$ |
| 1645 | $n\text{-}C_5H_{11}$ | F | F | F | Bond | $n\text{-}C_5H_{11}$ |
| 1646 | $n\text{-}C_5H_{11}$ | F | F | F | Bond | $n\text{-}C_6H_{13}$ |
| 1647 | $n\text{-}C_5H_{11}$ | F | F | F | Bond | $n\text{-}C_7H_{15}$ |

Examples 1648-1717

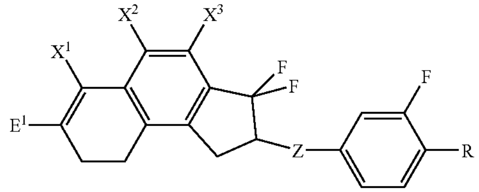

| Example | $E^1$ | $X^1$ | $X^2$ | $X^3$ | Z | R |
|---|---|---|---|---|---|---|
| 1648 | H | F | F | F | Bond | $CH_3$ |
| 1649 | H | F | F | F | Bond | $C_2H_5$ |
| 1650 | H | F | F | F | Bond | $n\text{-}C_3H_7$ |
| 1651 | H | F | F | F | Bond | $n\text{-}C_4H_9$ |
| 1652 | H | F | F | F | Bond | $n\text{-}C_5H_{11}$ |
| 1653 | H | F | F | F | Bond | $n\text{-}C_6H_{13}$ |
| 1654 | H | F | F | F | Bond | $n\text{-}C_7H_{15}$ |
| 1655 | H | F | F | F | $CF_2CF_2$ | $CH_3$ |
| 1656 | H | F | F | F | $CF_2CF_2$ | $C_2H_5$ |
| 1657 | H | F | F | F | $CF_2CF_2$ | $n\text{-}C_3H_7$ |
| 1658 | H | F | F | F | $CF_2CF_2$ | $n\text{-}C_4H_9$ |
| 1659 | H | F | F | F | $CF_2CF_2$ | $n\text{-}C_5H_{11}$ |
| 1660 | H | F | F | F | $CF_2CF_2$ | $n\text{-}C_6H_{13}$ |
| 1661 | H | F | F | F | $CF_2CF_2$ | $n\text{-}C_7H_{15}$ |
| 1662 | H | F | F | F | $CF_2O$ | $CH_3$ |
| 1663 | H | F | F | F | $CF_2O$ | $C_2H_5$ |
| 1664 | H | F | F | F | $CF_2O$ | $n\text{-}C_3H_7$ |
| 1665 | H | F | F | F | $CF_2O$ | $n\text{-}C_4H_9$ |
| 1666 | H | F | F | F | $CF_2O$ | $n\text{-}C_5H_{11}$ |
| 1667 | H | F | F | F | $CF_2O$ | $n\text{-}C_6H_{13}$ |
| 1668 | H | F | F | F | $CF_2O$ | $n\text{-}C_7H_{15}$ |
| 1669 | $CH_3$ | F | F | F | Bond | $CH_3$ |
| 1670 | $CH_3$ | F | F | F | Bond | $C_2H_5$ |
| 1671 | $CH_3$ | F | F | F | Bond | $n\text{-}C_3H_7$ |
| 1672 | $CH_3$ | F | F | F | Bond | $n\text{-}C_4H_9$ |
| 1673 | $CH_3$ | F | F | F | Bond | $n\text{-}C_5H_{11}$ |
| 1674 | $CH_3$ | F | F | F | Bond | $n\text{-}C_6H_{13}$ |
| 1675 | $CH_3$ | F | F | F | Bond | $n\text{-}C_7H_{15}$ |
| 1676 | $CH_3$ | F | F | F | $CF_2CF_2$ | $CH_3$ |
| 1677 | $CH_3$ | F | F | F | $CF_2CF_2$ | $C_2H_5$ |
| 1678 | $CH_3$ | F | F | F | $CF_2CF_2$ | $n\text{-}C_3H_7$ |
| 1679 | $CH_3$ | F | F | F | $CF_2CF_2$ | $n\text{-}C_4H_9$ |
| 1680 | $CH_3$ | F | F | F | $CF_2CF_2$ | $n\text{-}C_5H_{11}$ |
| 1681 | $CH_3$ | F | F | F | $CF_2CF_2$ | $n\text{-}C_6H_{13}$ |
| 1682 | $CH_3$ | F | F | F | $CF_2CF_2$ | $n\text{-}C_7H_{15}$ |
| 1683 | $CH_3$ | F | F | F | $CF_2O$ | $CH_3$ |
| 1684 | $CH_3$ | F | F | F | $CF_2O$ | $C_2H_5$ |
| 1685 | $CH_3$ | F | F | F | $CF_2O$ | $n\text{-}C_3H_7$ |
| 1686 | $CH_3$ | F | F | F | $CF_2O$ | $n\text{-}C_4H_9$ |
| 1687 | $CH_3$ | F | F | F | $CF_2O$ | $n\text{-}C_5H_{11}$ |
| 1688 | $CH_3$ | F | F | F | $CF_2O$ | $n\text{-}C_6H_{13}$ |
| 1689 | $CH_3$ | F | F | F | $CF_2O$ | $n\text{-}C_7H_{15}$ |
| 1690 | $C_2H_5$ | F | F | F | Bond | $CH_3$ |
| 1691 | $C_2H_5$ | F | F | F | Bond | $C_2H_5$ |
| 1692 | $C_2H_5$ | F | F | F | Bond | $n\text{-}C_3H_7$ |
| 1693 | $C_2H_5$ | F | F | F | Bond | $n\text{-}C_4H_9$ |
| 1694 | $C_2H_5$ | F | F | F | Bond | $n\text{-}C_5H_{11}$ |
| 1695 | $C_2H_5$ | F | F | F | Bond | $n\text{-}C_6H_{13}$ |
| 1696 | $C_2H_5$ | F | F | F | Bond | $n\text{-}C_7H_{15}$ |
| 1697 | $n\text{-}C_3H_7$ | F | F | F | Bond | $CH_3$ |
| 1698 | $n\text{-}C_3H_7$ | F | F | F | Bond | $C_2H_5$ |
| 1699 | $n\text{-}C_3H_7$ | F | F | F | Bond | $n\text{-}C_3H_7$ |
| 1700 | $n\text{-}C_3H_7$ | F | F | F | Bond | $n\text{-}C_4H_9$ |
| 1701 | $n\text{-}C_3H_7$ | F | F | F | Bond | $n\text{-}C_5H_{11}$ |
| 1702 | $n\text{-}C_3H_7$ | F | F | F | Bond | $n\text{-}C_6H_{13}$ |
| 1703 | $n\text{-}C_3H_7$ | F | F | F | Bond | $n\text{-}C_7H_{15}$ |
| 1704 | $n\text{-}C_4H_9$ | F | F | F | Bond | $CH_3$ |
| 1705 | $n\text{-}C_4H_9$ | F | F | F | Bond | $C_2H_5$ |
| 1706 | $n\text{-}C_4H_9$ | F | F | F | Bond | $n\text{-}C_3H_7$ |
| 1707 | $n\text{-}C_4H_9$ | F | F | F | Bond | $n\text{-}C_4H_9$ |
| 1708 | $n\text{-}C_4H_9$ | F | F | F | Bond | $n\text{-}C_5H_{11}$ |
| 1709 | $n\text{-}C_4H_9$ | F | F | F | Bond | $n\text{-}C_6H_{13}$ |
| 1710 | $n\text{-}C_4H_9$ | F | F | F | Bond | $n\text{-}C_7H_{15}$ |
| 1711 | $n\text{-}C_5H_{11}$ | F | F | F | Bond | $CH_3$ |

-continued

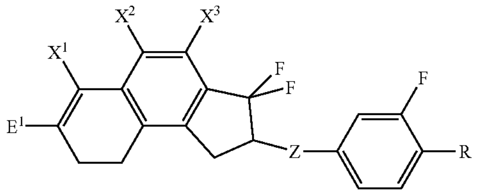

| Example | $E^1$ | $X^1$ | $X^2$ | $X^3$ | Z | R |
|---|---|---|---|---|---|---|
| 1712 | n-$C_5H_{11}$ | F | F | F | Bond | $C_2H_5$ |
| 1713 | n-$C_5H_{11}$ | F | F | F | Bond | n-$C_3H_7$ |
| 1714 | n-$C_5H_{11}$ | F | F | F | Bond | n-$C_4H_9$ |
| 1715 | n-$C_5H_{11}$ | F | F | F | Bond | n-$C_5H_{11}$ |
| 1716 | n-$C_5H_{11}$ | F | F | F | Bond | n-$C_6H_{13}$ |
| 1717 | n-$C_5H_{11}$ | F | F | F | Bond | n-$C_7H_{15}$ |

Examples 1718-1766

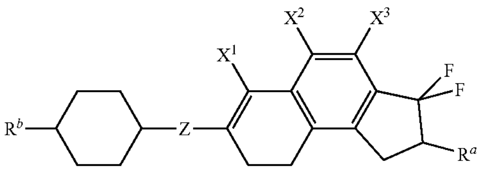

| Example | $R^b$ | $X^1$ | $X^2$ | $X^3$ | Z | $R^a$ |
|---|---|---|---|---|---|---|
| 1718 | $CH_3$ | F | F | F | Bond | $CH_3$ |
| 1719 | $CH_3$ | F | F | F | Bond | $C_2H_5$ |
| 1720 | $CH_3$ | F | F | F | Bond | n-$C_3H_7$ |
| 1721 | $CH_3$ | F | F | F | Bond | n-$C_4H_9$ |
| 1722 | $CH_3$ | F | F | F | Bond | n-$C_5H_{11}$ |
| 1723 | $CH_3$ | F | F | F | Bond | n-$C_6H_{13}$ |
| 1724 | $CH_3$ | F | F | F | Bond | n-$C_7H_{15}$ |
| 1725 | $CH_3$ | F | F | F | $CF_2CF_2$ | $CH_3$ |
| 1726 | $CH_3$ | F | F | F | $CF_2CF_2$ | $C_2H_5$ |
| 1727 | $CH_3$ | F | F | F | $CF_2CF_2$ | n-$C_3H_7$ |
| 1728 | $CH_3$ | F | F | F | $CF_2CF_2$ | n-$C_4H_9$ |
| 1729 | $CH_3$ | F | F | F | $CF_2CF_2$ | n-$C_5H_{11}$ |
| 1730 | $CH_3$ | F | F | F | $CF_2CF_2$ | n-$C_6H_{13}$ |
| 1731 | $CH_3$ | F | F | F | $CF_2CF_2$ | n-$C_7H_{15}$ |
| 1732 | $C_2H_5$ | F | F | F | $CF_2CF_2$ | $CH_3$ |
| 1733 | $C_2H_5$ | F | F | F | $CF_2CF_2$ | $C_2H_5$ |
| 1734 | $C_2H_5$ | F | F | F | $CF_2CF_2$ | n-$C_3H_7$ |
| 1735 | $C_2H_5$ | F | F | F | $CF_2CF_2$ | n-$C_4H_9$ |
| 1736 | $C_2H_5$ | F | F | F | $CF_2CF_2$ | n-$C_5H_{11}$ |
| 1737 | $C_2H_5$ | F | F | F | $CF_2CF_2$ | n-$C_6H_{13}$ |
| 1738 | $C_2H_5$ | F | F | F | $CF_2CF_2$ | n-$C_7H_{15}$ |
| 1739 | $C_2H_5$ | F | F | F | Bond | $CH_3$ |
| 1740 | $C_2H_5$ | F | F | F | Bond | $C_2H_5$ |
| 1741 | $C_2H_5$ | F | F | F | Bond | n-$C_3H_7$ |
| 1742 | $C_2H_5$ | F | F | F | Bond | n-$C_4H_9$ |
| 1743 | $C_2H_5$ | F | F | F | Bond | n-$C_5H_{11}$ |
| 1744 | $C_2H_5$ | F | F | F | Bond | n-$C_6H_{13}$ |
| 1745 | $C_2H_5$ | F | F | F | Bond | n-$C_7H_{15}$ |
| 1746 | n-$C_3H_7$ | F | F | F | Bond | $CH_3$ |
| 1747 | n-$C_3H_7$ | F | F | F | Bond | $C_2H_5$ |
| 1748 | n-$C_3H_7$ | F | F | F | Bond | n-$C_3H_7$ |
| 1749 | n-$C_3H_7$ | F | F | F | Bond | n-$C_4H_9$ |
| 1750 | n-$C_3H_7$ | F | F | F | Bond | n-$C_5H_{11}$ |
| 1751 | n-$C_3H_7$ | F | F | F | Bond | n-$C_6H_{13}$ |
| 1752 | n-$C_3H_7$ | F | F | F | Bond | n-$C_7H_{15}$ |
| 1753 | n-$C_4H_9$ | F | F | F | Bond | $CH_3$ |
| 1754 | n-$C_4H_9$ | F | F | F | Bond | $C_2H_5$ |
| 1755 | n-$C_4H_9$ | F | F | F | Bond | n-$C_3H_7$ |
| 1756 | n-$C_4H_9$ | F | F | F | Bond | n-$C_4H_9$ |
| 1757 | n-$C_4H_9$ | F | F | F | Bond | n-$C_5H_{11}$ |
| 1758 | n-$C_4H_9$ | F | F | F | Bond | n-$C_6H_{13}$ |

-continued

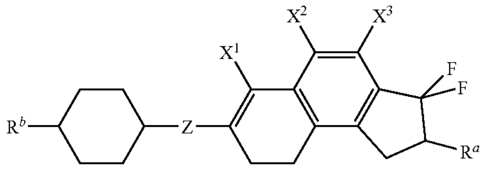

| Example | $R^b$ | $X^1$ | $X^2$ | $X^3$ | Z | $R^a$ |
|---|---|---|---|---|---|---|
| 1759 | n-$C_4H_9$ | F | F | F | Bond | n-$C_7H_{15}$ |
| 1760 | n-$C_5H_{11}$ | F | F | F | Bond | $CH_3$ |
| 1761 | n-$C_5H_{11}$ | F | F | F | Bond | $C_2H_5$ |
| 1762 | n-$C_5H_{11}$ | F | F | F | Bond | n-$C_3H_7$ |
| 1763 | n-$C_5H_{11}$ | F | F | F | Bond | n-$C_4H_9$ |
| 1764 | n-$C_5H_{11}$ | F | F | F | Bond | n-$C_5H_{11}$ |
| 1765 | n-$C_5H_{11}$ | F | F | F | Bond | n-$C_6H_{13}$ |
| 1766 | n-$C_5H_{11}$ | F | F | F | Bond | n-$C_7H_{15}$ |

Examples 1767-1829

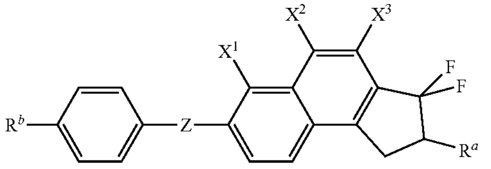

| Example | $R^b$ | $X^1$ | $X^2$ | $X^3$ | Z | $R^a$ |
|---|---|---|---|---|---|---|
| 1767 | $CH_3$ | F | F | F | Bond | $CH_3$ |
| 1768 | $CH_3$ | F | F | F | Bond | $C_2H_5$ |
| 1769 | $CH_3$ | F | F | F | Bond | n-$C_3H_7$ |
| 1770 | $CH_3$ | F | F | F | Bond | n-$C_4H_9$ |
| 1771 | $CH_3$ | F | F | F | Bond | n-$C_5H_{11}$ |
| 1772 | $CH_3$ | F | F | F | Bond | n-$C_6H_{13}$ |
| 1773 | $CH_3$ | F | F | F | Bond | n-$C_7H_{15}$ |
| 1774 | $CH_3$ | F | F | F | $CF_2CF_2$ | $CH_3$ |
| 1775 | $CH_3$ | F | F | F | $CF_2CF_2$ | $C_2H_5$ |
| 1776 | $CH_3$ | F | F | F | $CF_2CF_2$ | n-$C_3H_7$ |
| 1777 | $CH_3$ | F | F | F | $CF_2CF_2$ | n-$C_4H_9$ |
| 1778 | $CH_3$ | F | F | F | $CF_2CF_2$ | n-$C_5H_{11}$ |
| 1779 | $CH_3$ | F | F | F | $CF_2CF_2$ | n-$C_6H_{13}$ |
| 1780 | $CH_3$ | F | F | F | $CF_2CF_2$ | n-$C_7H_{15}$ |
| 1781 | $CH_3$ | F | F | F | $CF_2O$ | $CH_3$ |
| 1782 | $CH_3$ | F | F | F | $CF_2O$ | $C_2H_5$ |
| 1783 | $CH_3$ | F | F | F | $CF_2O$ | n-$C_3H_7$ |
| 1784 | $CH_3$ | F | F | F | $CF_2O$ | n-$C_4H_9$ |
| 1785 | $CH_3$ | F | F | F | $CF_2O$ | n-$C_5H_{11}$ |
| 1786 | $CH_3$ | F | F | F | $CF_2O$ | n-$C_6H_{13}$ |
| 1787 | $CH_3$ | F | F | F | $CF_2O$ | n-$C_7H_{15}$ |
| 1788 | $C_2H_5$ | F | F | F | $CF_2CF_2$ | $CH_3$ |
| 1789 | $C_2H_5$ | F | F | F | $CF_2CF_2$ | $C_2H_5$ |
| 1790 | $C_2H_5$ | F | F | F | $CF_2CF_2$ | n-$C_3H_7$ |
| 1791 | $C_2H_5$ | F | F | F | $CF_2CF_2$ | n-$C_4H_9$ |
| 1792 | $C_2H_5$ | F | F | F | $CF_2CF_2$ | n-$C_5H_{11}$ |
| 1793 | $C_2H_5$ | F | F | F | $CF_2CF_2$ | n-$C_6H_{13}$ |
| 1794 | $C_2H_5$ | F | F | F | $CF_2CF_2$ | n-$C_7H_{15}$ |
| 1795 | $C_2H_5$ | F | F | F | $CF_2O$ | $CH_3$ |
| 1796 | $C_2H_5$ | F | F | F | $CF_2O$ | $C_2H_5$ |
| 1797 | $C_2H_5$ | F | F | F | $CF_2O$ | n-$C_3H_7$ |
| 1798 | $C_2H_5$ | F | F | F | $CF_2O$ | n-$C_4H_9$ |
| 1799 | $C_2H_5$ | F | F | F | $CF_2O$ | n-$C_5H_{11}$ |
| 1800 | $C_2H_5$ | F | F | F | $CF_2O$ | n-$C_6H_{13}$ |
| 1801 | $C_2H_5$ | F | F | F | $CF_2O$ | n-$C_7H_{15}$ |
| 1802 | $C_2H_5$ | F | F | F | Bond | $CH_3$ |
| 1803 | $C_2H_5$ | F | F | F | Bond | $C_2H_5$ |
| 1804 | $C_2H_5$ | F | F | F | Bond | n-$C_3H_7$ |
| 1805 | $C_2H_5$ | F | F | F | Bond | n-$C_4H_9$ |
| 1806 | $C_2H_5$ | F | F | F | Bond | n-$C_5H_{11}$ |

-continued

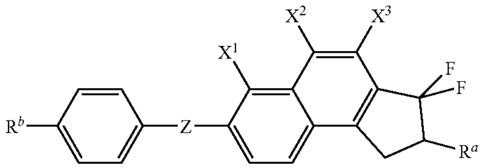

| Example | $R^b$ | $X^1$ | $X^2$ | $X^3$ | Z | $R^a$ |
|---|---|---|---|---|---|---|
| 1807 | $C_2H_5$ | F | F | F | Bond | n-$C_6H_{13}$ |
| 1808 | $C_2H_5$ | F | F | F | Bond | n-$C_7H_{15}$ |
| 1809 | n-$C_3H_7$ | F | F | F | Bond | $CH_3$ |
| 1810 | n-$C_3H_7$ | F | F | F | Bond | $C_2H_5$ |
| 1811 | n-$C_3H_7$ | F | F | F | Bond | n-$C_3H_7$ |
| 1812 | n-$C_3H_7$ | F | F | F | Bond | n-$C_4H_9$ |
| 1813 | n-$C_3H_7$ | F | F | F | Bond | n-$C_5H_{11}$ |
| 1814 | n-$C_3H_7$ | F | F | F | Bond | n-$C_6H_{13}$ |
| 1815 | n-$C_3H_7$ | F | F | F | Bond | n-$C_7H_{15}$ |
| 1816 | n-$C_4H_9$ | F | F | F | Bond | $CH_3$ |
| 1817 | n-$C_4H_9$ | F | F | F | Bond | $C_2H_5$ |
| 1818 | n-$C_4H_9$ | F | F | F | Bond | n-$C_3H_7$ |
| 1819 | n-$C_4H_9$ | F | F | F | Bond | n-$C_4H_9$ |
| 1820 | n-$C_4H_9$ | F | F | F | Bond | n-$C_5H_{11}$ |
| 1821 | n-$C_4H_9$ | F | F | F | Bond | n-$C_6H_{13}$ |
| 1822 | n-$C_4H_9$ | F | F | F | Bond | n-$C_7H_{15}$ |
| 1823 | n-$C_5H_{11}$ | F | F | F | Bond | $CH_3$ |
| 1824 | n-$C_5H_{11}$ | F | F | F | Bond | $C_2H_5$ |
| 1825 | n-$C_5H_{11}$ | F | F | F | Bond | n-$C_3H_7$ |
| 1826 | n-$C_5H_{11}$ | F | F | F | Bond | n-$C_4H_9$ |
| 1827 | n-$C_5H_{11}$ | F | F | F | Bond | n-$C_5H_{11}$ |
| 1828 | n-$C_5H_{11}$ | F | F | F | Bond | n-$C_6H_{13}$ |
| 1829 | n-$C_5H_{11}$ | F | F | F | Bond | n-$C_7H_{15}$ |

Examples 1830-1871

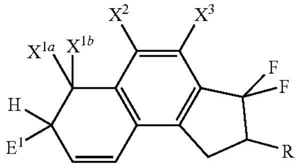

| Example | $E^1$ | $X^{1a}$ | $X^{1b}$ | $X^2$ | $X^3$ | R |
|---|---|---|---|---|---|---|
| 1830 | H | F | F | F | F | $CH_3$ |
| 1831 | H | F | F | F | F | $C_2H_5$ |
| 1832 | H | F | F | F | F | n-$C_3H_7$ |
| 1833 | H | F | F | F | F | n-$C_4H_9$ |
| 1834 | H | F | F | F | F | n-$C_5H_{11}$ |
| 1835 | H | F | F | F | F | n-$C_6H_{13}$ |
| 1836 | H | F | F | F | F | n-$C_7H_{15}$ |
| 1837 | $CH_3$ | F | F | F | F | $CH_3$ |
| 1838 | $CH_3$ | F | F | F | F | $C_2H_5$ |
| 1839 | $CH_3$ | F | F | F | F | n-$C_3H_7$ |
| 1840 | $CH_3$ | F | F | F | F | n-$C_4H_9$ |
| 1841 | $CH_3$ | F | F | F | F | n-$C_5H_{11}$ |
| 1842 | $CH_3$ | F | F | F | F | n-$C_6H_{13}$ |
| 1843 | $CH_3$ | F | F | F | F | n-$C_7H_{15}$ |
| 1844 | $C_2H_5$ | F | F | F | F | $CH_3$ |
| 1845 | $C_2H_5$ | F | F | F | F | $C_2H_5$ |
| 1846 | $C_2H_5$ | F | F | F | F | n-$C_3H_7$ |
| 1847 | $C_2H_5$ | F | F | F | F | n-$C_4H_9$ |
| 1848 | $C_2H_5$ | F | F | F | F | n-$C_5H_{11}$ |
| 1849 | $C_2H_5$ | F | F | F | F | n-$C_6H_{13}$ |
| 1850 | $C_2H_5$ | F | F | F | F | n-$C_7H_{15}$ |
| 1851 | n-$C_3H_7$ | F | F | F | F | $CH_3$ |
| 1852 | n-$C_3H_7$ | F | F | F | F | $C_2H_5$ |
| 1853 | n-$C_3H_7$ | F | F | F | F | n-$C_3H_7$ |
| 1854 | n-$C_3H_7$ | F | F | F | F | n-$C_4H_9$ |

-continued

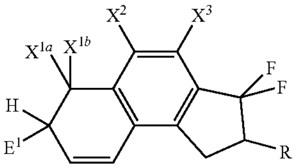

| Example | $E^1$ | $X^{1a}$ | $X^{1b}$ | $X^2$ | $X^3$ | R |
|---|---|---|---|---|---|---|
| 1855 | n-$C_3H_7$ | F | F | F | F | n-$C_5H_{11}$ |
| 1856 | n-$C_3H_7$ | F | F | F | F | n-$C_6H_{13}$ |
| 1857 | n-$C_3H_7$ | F | F | F | F | n-$C_7H_{15}$ |
| 1858 | n-$C_4H_9$ | F | F | F | F | $CH_3$ |
| 1859 | n-$C_4H_9$ | F | F | F | F | $C_2H_5$ |
| 1860 | n-$C_4H_9$ | F | F | F | F | n-$C_3H_7$ |
| 1861 | n-$C_4H_9$ | F | F | F | F | n-$C_4H_9$ |
| 1862 | n-$C_4H_9$ | F | F | F | F | n-$C_5H_{11}$ |
| 1863 | n-$C_4H_9$ | F | F | F | F | n-$C_6H_{13}$ |
| 1864 | n-$C_4H_9$ | F | F | F | F | n-$C_7H_{15}$ |
| 1865 | n-$C_5H_{11}$ | F | F | F | F | $CH_3$ |
| 1866 | n-$C_5H_{11}$ | F | F | F | F | $C_2H_5$ |
| 1867 | n-$C_5H_{11}$ | F | F | F | F | n-$C_3H_7$ |
| 1868 | n-$C_5H_{11}$ | F | F | F | F | n-$C_4H_9$ |
| 1869 | n-$C_5H_{11}$ | F | F | F | F | n-$C_5H_{11}$ |
| 1870 | n-$C_5H_{11}$ | F | F | F | F | n-$C_6H_{13}$ |
| 1871 | n-$C_5H_{11}$ | F | F | F | F | n-$C_7H_{15}$ |

Example 1872-1941

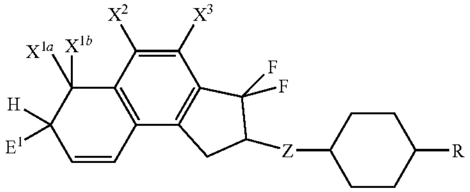

| Example | $E^1$ | $X^{1a}$ | $X^{1b}$ | $X^2$ | $X^3$ | Z | R |
|---|---|---|---|---|---|---|---|
| 1872 | H | F | F | F | F | Bond | $CH_3$ |
| 1873 | H | F | F | F | F | Bond | $C_2H_5$ |
| 1874 | H | F | F | F | F | Bond | n-$C_3H_7$ |
| 1875 | H | F | F | F | F | Bond | n-$C_4H_9$ |
| 1876 | H | F | F | F | F | Bond | n-$C_5H_{11}$ |
| 1877 | H | F | F | F | F | Bond | n-$C_6H_{13}$ |
| 1878 | H | F | F | F | F | Bond | n-$C_7H_{15}$ |
| 1879 | H | F | F | F | F | $CF_2CF_2$ | $CH_3$ |
| 1880 | H | F | F | F | F | $CF_2CF_2$ | $C_2H_5$ |
| 1881 | H | F | F | F | F | $CF_2CF_2$ | n-$C_3H_7$ |
| 1882 | H | F | F | F | F | $CF_2CF_2$ | n-$C_4H_9$ |
| 1883 | H | F | F | F | F | $CF_2CF_2$ | n-$C_5H_{11}$ |
| 1884 | H | F | F | F | F | $CF_2CF_2$ | n-$C_6H_{13}$ |
| 1885 | H | F | F | F | F | $CF_2CF_2$ | n-$C_7H_{15}$ |
| 1886 | H | F | F | F | F | $OCF_2$ | $CH_3$ |
| 1887 | H | F | F | F | F | $OCF_2$ | $C_2H_5$ |
| 1888 | H | F | F | F | F | $OCF_2$ | n-$C_3H_7$ |
| 1889 | H | F | F | F | F | $OCF_2$ | n-$C_4H_9$ |
| 1890 | H | F | F | F | F | $OCF_2$ | n-$C_5H_{11}$ |
| 1891 | H | F | F | F | F | $OCF_2$ | n-$C_6H_{13}$ |
| 1892 | H | F | F | F | F | $OCF_2$ | n-$C_7H_{15}$ |
| 1893 | $CH_3$ | F | F | F | F | Bond | $CH_3$ |
| 1894 | $CH_3$ | F | F | F | F | Bond | $C_2H_5$ |
| 1895 | $CH_3$ | F | F | F | F | Bond | n-$C_3H_7$ |
| 1896 | $CH_3$ | F | F | F | F | Bond | n-$C_4H_9$ |
| 1897 | $CH_3$ | F | F | F | F | Bond | n-$C_5H_{11}$ |
| 1898 | $CH_3$ | F | F | F | F | Bond | n-$C_6H_{13}$ |
| 1899 | $CH_3$ | F | F | F | F | Bond | n-$C_7H_{15}$ |
| 1900 | $CH_3$ | F | F | F | F | $CF_2CF_2$ | $CH_3$ |
| 1901 | $CH_3$ | F | F | F | F | $CF_2CF_2$ | $C_2H_5$ |

-continued

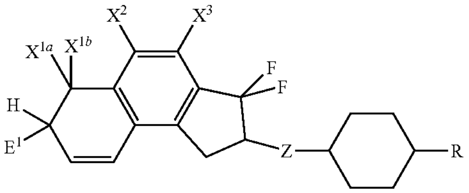

| Example | $E^1$ | $X^{1a}$ | $X^{1b}$ | $X^2$ | $X^3$ | Z | R |
|---|---|---|---|---|---|---|---|
| 1902 | $CH_3$ | F | F | F | F | $CF_2CF_2$ | n-$C_3H_7$ |
| 1903 | $CH_3$ | F | F | F | F | $CF_2CF_2$ | n-$C_4H_9$ |
| 1904 | $CH_3$ | F | F | F | F | $CF_2CF_2$ | n-$C_5H_{11}$ |
| 1905 | $CH_3$ | F | F | F | F | $CF_2CF_2$ | n-$C_6H_{13}$ |
| 1906 | $CH_3$ | F | F | F | F | $CF_2CF_2$ | n-$C_7H_{15}$ |
| 1907 | $CH_3$ | F | F | F | F | $OCF_2$ | $CH_3$ |
| 1908 | $CH_3$ | F | F | F | F | $OCF_2$ | $C_2H_5$ |
| 1909 | $CH_3$ | F | F | F | F | $OCF_2$ | n-$C_3H_7$ |
| 1910 | $CH_3$ | F | F | F | F | $OCF_2$ | n-$C_4H_9$ |
| 1911 | $CH_3$ | F | F | F | F | $OCF_2$ | n-$C_5H_{11}$ |
| 1912 | $CH_3$ | F | F | F | F | $OCF_2$ | n-$C_6H_{13}$ |
| 1913 | $CH_3$ | F | F | F | F | $OCF_2$ | n-$C_7H_{15}$ |
| 1914 | $C_2H_5$ | F | F | F | F | Bond | $CH_3$ |
| 1915 | $C_2H_5$ | F | F | F | F | Bond | $C_2H_5$ |
| 1916 | $C_2H_5$ | F | F | F | F | Bond | n-$C_3H_7$ |
| 1917 | $C_2H_5$ | F | F | F | F | Bond | n-$C_4H_9$ |
| 1918 | $C_2H_5$ | F | F | F | F | Bond | n-$C_5H_{11}$ |
| 1919 | $C_2H_5$ | F | F | F | F | Bond | n-$C_6H_{13}$ |
| 1920 | $C_2H_5$ | F | F | F | F | Bond | n-$C_7H_{15}$ |
| 1921 | n-$C_3H_7$ | F | F | F | F | Bond | $CH_3$ |
| 1922 | n-$C_3H_7$ | F | F | F | F | Bond | $C_2H_5$ |
| 1923 | n-$C_3H_7$ | F | F | F | F | Bond | n-$C_3H_7$ |
| 1924 | n-$C_3H_7$ | F | F | F | F | Bond | n-$C_4H_9$ |
| 1925 | n-$C_3H_7$ | F | F | F | F | Bond | n-$C_5H_{11}$ |
| 1926 | n-$C_3H_7$ | F | F | F | F | Bond | n-$C_6H_{13}$ |
| 1927 | n-$C_3H_7$ | F | F | F | F | Bond | n-$C_7H_{15}$ |
| 1928 | n-$C_4H_9$ | F | F | F | F | Bond | $CH_3$ |
| 1929 | n-$C_4H_9$ | F | F | F | F | Bond | $C_2H_5$ |
| 1930 | n-$C_4H_9$ | F | F | F | F | Bond | n-$C_3H_7$ |
| 1931 | n-$C_4H_9$ | F | F | F | F | Bond | n-$C_4H_9$ |
| 1932 | n-$C_4H_9$ | F | F | F | F | Bond | n-$C_5H_{11}$ |
| 1933 | n-$C_4H_9$ | F | F | F | F | Bond | n-$C_6H_{13}$ |
| 1934 | n-$C_4H_9$ | F | F | F | F | Bond | n-$C_7H_{15}$ |
| 1935 | n-$C_5H_{11}$ | F | F | F | F | Bond | $CH_3$ |
| 1936 | n-$C_5H_{11}$ | F | F | F | F | Bond | $C_2H_5$ |
| 1937 | n-$C_5H_{11}$ | F | F | F | F | Bond | n-$C_3H_7$ |
| 1938 | n-$C_5H_{11}$ | F | F | F | F | Bond | n-$C_4H_9$ |
| 1939 | n-$C_5H_{11}$ | F | F | F | F | Bond | n-$C_5H_{11}$ |
| 1940 | n-$C_5H_{11}$ | F | F | F | F | Bond | n-$C_6H_{13}$ |
| 1941 | n-$C_5H_{11}$ | F | F | F | F | Bond | n-$C_7H_{15}$ |

Examples 1942-2011

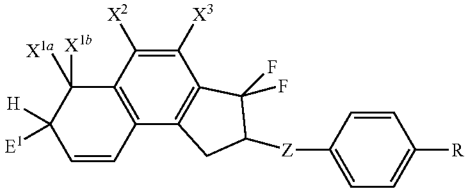

| Example | $E^1$ | $X^{1a}$ | $X^{1b}$ | $X^2$ | $X^3$ | Z | R |
|---|---|---|---|---|---|---|---|
| 1942 | H | F | F | F | F | Bond | $CH_3$ |
| 1943 | H | F | F | F | F | Bond | $C_2H_5$ |
| 1944 | H | F | F | F | F | Bond | n-$C_3H_7$ |
| 1945 | H | F | F | F | F | Bond | n-$C_4H_9$ |
| 1946 | H | F | F | F | F | Bond | n-$C_5H_{11}$ |
| 1947 | H | F | F | F | F | Bond | n-$C_6H_{13}$ |

-continued

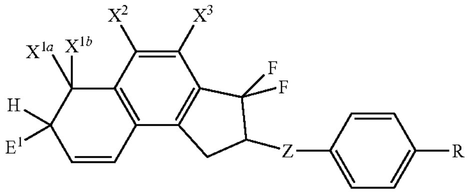

| Example | $E^1$ | $X^{1a}$ | $X^{1b}$ | $X^2$ | $X^3$ | Z | R |
|---|---|---|---|---|---|---|---|
| 1948 | H | F | F | F | F | Bond | n-$C_7H_{15}$ |
| 1949 | H | F | F | F | F | $CF_2CF_2$ | $CH_3$ |
| 1950 | H | F | F | F | F | $CF_2CF_2$ | $C_2H_5$ |
| 1951 | H | F | F | F | F | $CF_2CF_2$ | n-$C_3H_7$ |
| 1952 | H | F | F | F | F | $CF_2CF_2$ | n-$C_4H_9$ |
| 1953 | H | F | F | F | F | $CF_2CF_2$ | n-$C_5H_{11}$ |
| 1954 | H | F | F | F | F | $CF_2CF_2$ | n-$C_6H_{13}$ |
| 1955 | H | F | F | F | F | $CF_2CF_2$ | n-$C_7H_{15}$ |
| 1956 | H | F | F | F | F | $CF_2O$ | $CH_3$ |
| 1957 | H | F | F | F | F | $CF_2O$ | $C_2H_5$ |
| 1958 | H | F | F | F | F | $CF_2O$ | n-$C_3H_7$ |
| 1959 | H | F | F | F | F | $CF_2O$ | n-$C_4H_9$ |
| 1960 | H | F | F | F | F | $CF_2O$ | n-$C_5H_{11}$ |
| 1961 | H | F | F | F | F | $CF_2O$ | n-$C_6H_{13}$ |
| 1962 | H | F | F | F | F | $CF_2O$ | n-$C_7H_{15}$ |
| 1963 | $CH_3$ | F | F | F | F | Bond | $CH_3$ |
| 1964 | $CH_3$ | F | F | F | F | Bond | $C_2H_5$ |
| 1965 | $CH_3$ | F | F | F | F | Bond | n-$C_3H_7$ |
| 1966 | $CH_3$ | F | F | F | F | Bond | n-$C_4H_9$ |
| 1967 | $CH_3$ | F | F | F | F | Bond | n-$C_5H_{11}$ |
| 1968 | $CH_3$ | F | F | F | F | Bond | n-$C_6H_{13}$ |
| 1969 | $CH_3$ | F | F | F | F | Bond | n-$C_7H_{15}$ |
| 1970 | $CH_3$ | F | F | F | F | $CF_2CF_2$ | $CH_3$ |
| 1971 | $CH_3$ | F | F | F | F | $CF_2CF_2$ | $C_2H_5$ |
| 1972 | $CH_3$ | F | F | F | F | $CF_2CF_2$ | n-$C_3H_7$ |
| 1973 | $CH_3$ | F | F | F | F | $CF_2CF_2$ | n-$C_4H_9$ |
| 1974 | $CH_3$ | F | F | F | F | $CF_2CF_2$ | n-$C_5H_{11}$ |
| 1975 | $CH_3$ | F | F | F | F | $CF_2CF_2$ | n-$C_6H_{13}$ |
| 1976 | $CH_3$ | F | F | F | F | $CF_2CF_2$ | n-$C_7H_{15}$ |
| 1977 | $CH_3$ | F | F | F | F | $CF_2O$ | $CH_3$ |
| 1978 | $CH_3$ | F | F | F | F | $CF_2O$ | $C_2H_5$ |
| 1979 | $CH_3$ | F | F | F | F | $CF_2O$ | n-$C_3H_7$ |
| 1980 | $CH_3$ | F | F | F | F | $CF_2O$ | n-$C_4H_9$ |
| 1981 | $CH_3$ | F | F | F | F | $CF_2O$ | n-$C_5H_{11}$ |
| 1982 | $CH_3$ | F | F | F | F | $CF_2O$ | n-$C_6H_{13}$ |
| 1983 | $CH_3$ | F | F | F | F | $CF_2O$ | n-$C_7H_{15}$ |
| 1984 | $C_2H_5$ | F | F | F | F | Bond | $CH_3$ |
| 1985 | $C_2H_5$ | F | F | F | F | Bond | $C_2H_5$ |
| 1986 | $C_2H_5$ | F | F | F | F | Bond | n-$C_3H_7$ |
| 1987 | $C_2H_5$ | F | F | F | F | Bond | n-$C_4H_9$ |
| 1988 | $C_2H_5$ | F | F | F | F | Bond | n-$C_5H_{11}$ |
| 1989 | $C_2H_5$ | F | F | F | F | Bond | n-$C_6H_{13}$ |
| 1990 | $C_2H_5$ | F | F | F | F | Bond | n-$C_7H_{15}$ |
| 1991 | n-$C_3H_7$ | F | F | F | F | Bond | $CH_3$ |
| 1992 | n-$C_3H_7$ | F | F | F | F | Bond | $C_2H_5$ |
| 1993 | n-$C_3H_7$ | F | F | F | F | Bond | n-$C_3H_7$ |
| 1994 | n-$C_3H_7$ | F | F | F | F | Bond | n-$C_4H_9$ |
| 1995 | n-$C_3H_7$ | F | F | F | F | Bond | n-$C_5H_{11}$ |
| 1996 | n-$C_3H_7$ | F | F | F | F | Bond | n-$C_6H_{13}$ |
| 1997 | n-$C_3H_7$ | F | F | F | F | Bond | n-$C_7H_{15}$ |
| 1998 | n-$C_4H_9$ | F | F | F | F | Bond | $CH_3$ |
| 1999 | n-$C_4H_9$ | F | F | F | F | Bond | $C_2H_5$ |
| 2000 | n-$C_4H_9$ | F | F | F | F | Bond | n-$C_3H_7$ |
| 2001 | n-$C_4H_9$ | F | F | F | F | Bond | n-$C_4H_9$ |
| 2002 | n-$C_4H_9$ | F | F | F | F | Bond | n-$C_5H_{11}$ |
| 2003 | n-$C_4H_9$ | F | F | F | F | Bond | n-$C_6H_{13}$ |
| 2004 | n-$C_4H_9$ | F | F | F | F | Bond | n-$C_7H_{15}$ |
| 2005 | n-$C_5H_{11}$ | F | F | F | F | Bond | $CH_3$ |
| 2006 | n-$C_5H_{11}$ | F | F | F | F | Bond | $C_2H_5$ |
| 2007 | n-$C_5H_{11}$ | F | F | F | F | Bond | n-$C_3H_7$ |
| 2008 | n-$C_5H_{11}$ | F | F | F | F | Bond | n-$C_4H_9$ |
| 2009 | n-$C_5H_{11}$ | F | F | F | F | Bond | n-$C_5H_{11}$ |
| 2010 | n-$C_5H_{11}$ | F | F | F | F | Bond | n-$C_6H_{13}$ |
| 2011 | n-$C_5H_{11}$ | F | F | F | F | Bond | n-$C_7H_{15}$ |

Examples 2012-2081

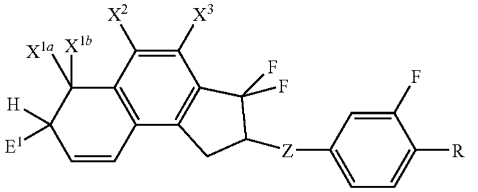

| Example | $E^1$ | $X^{1a}$ | $X^{1b}$ | $X^2$ | $X^3$ | Z | R |
|---|---|---|---|---|---|---|---|
| 2012 | H | F | F | F | F | Bond | $CH_3$ |
| 2013 | H | F | F | F | F | Bond | $C_2H_5$ |
| 2014 | H | F | F | F | F | Bond | n-$C_3H_7$ |
| 2015 | H | F | F | F | F | Bond | n-$C_4H_9$ |
| 2016 | H | F | F | F | F | Bond | n-$C_5H_{11}$ |
| 2017 | H | F | F | F | F | Bond | n-$C_6H_{13}$ |
| 2018 | H | F | F | F | F | Bond | n-$C_7H_{15}$ |
| 2019 | H | F | F | F | F | $CF_2CF_2$ | $CH_3$ |
| 2020 | H | F | F | F | F | $CF_2CF_2$ | $C_2H_5$ |
| 2021 | H | F | F | F | F | $CF_2CF_2$ | n-$C_3H_7$ |
| 2022 | H | F | F | F | F | $CF_2CF_2$ | n-$C_4H_9$ |
| 2023 | H | F | F | F | F | $CF_2CF_2$ | n-$C_5H_{11}$ |
| 2024 | H | F | F | F | F | $CF_2CF_2$ | n-$C_6H_{13}$ |
| 2025 | H | F | F | F | F | $CF_2CF_2$ | n-$C_7H_{15}$ |
| 2026 | H | F | F | F | F | $CF_2O$ | $CH_3$ |
| 2027 | H | F | F | F | F | $CF_2O$ | $C_2H_5$ |
| 2028 | H | F | F | F | F | $CF_2O$ | n-$C_3H_7$ |
| 2029 | H | F | F | F | F | $CF_2O$ | n-$C_4H_9$ |
| 2030 | H | F | F | F | F | $CF_2O$ | n-$C_5H_{11}$ |
| 2031 | H | F | F | F | F | $CF_2O$ | n-$C_6H_{13}$ |
| 2032 | H | F | F | F | F | $CF_2O$ | n-$C_7H_{15}$ |
| 2033 | $CH_3$ | F | F | F | F | Bond | $CH_3$ |
| 2034 | $CH_3$ | F | F | F | F | Bond | $C_2H_5$ |
| 2035 | $CH_3$ | F | F | F | F | Bond | n-$C_3H_7$ |
| 2036 | $CH_3$ | F | F | F | F | Bond | n-$C_4H_9$ |
| 2037 | $CH_3$ | F | F | F | F | Bond | n-$C_5H_{11}$ |
| 2038 | $CH_3$ | F | F | F | F | Bond | n-$C_6H_{13}$ |
| 2039 | $CH_3$ | F | F | F | F | Bond | n-$C_7H_{15}$ |
| 2040 | $CH_3$ | F | F | F | F | $CF_2CF_2$ | $CH_3$ |
| 2041 | $CH_3$ | F | F | F | F | $CF_2CF_2$ | $C_2H_5$ |
| 2042 | $CH_3$ | F | F | F | F | $CF_2CF_2$ | n-$C_3H_7$ |
| 2043 | $CH_3$ | F | F | F | F | $CF_2CF_2$ | n-$C_4H_9$ |
| 2044 | $CH_3$ | F | F | F | F | $CF_2CF_2$ | n-$C_5H_{11}$ |
| 2045 | $CH_3$ | F | F | F | F | $CF_2CF_2$ | n-$C_6H_{13}$ |
| 2046 | $CH_3$ | F | F | F | F | $CF_2CF_2$ | n-$C_7H_{15}$ |
| 2047 | $CH_3$ | F | F | F | F | $CF_2O$ | $CH_3$ |
| 2048 | $CH_3$ | F | F | F | F | $CF_2O$ | $C_2H_5$ |
| 2049 | $CH_3$ | F | F | F | F | $CF_2O$ | n-$C_3H_7$ |
| 2050 | $CH_3$ | F | F | F | F | $CF_2O$ | n-$C_4H_9$ |
| 2051 | $CH_3$ | F | F | F | F | $CF_2O$ | n-$C_5H_{11}$ |
| 2052 | $CH_3$ | F | F | F | F | $CF_2O$ | n-$C_6H_{13}$ |
| 2053 | $CH_3$ | F | F | F | F | $CF_2O$ | n-$C_7H_{15}$ |
| 2054 | $C_2H_5$ | F | F | F | F | Bond | $CH_3$ |
| 2055 | $C_2H_5$ | F | F | F | F | Bond | $C_2H_5$ |
| 2056 | $C_2H_5$ | F | F | F | F | Bond | n-$C_3H_7$ |
| 2057 | $C_2H_5$ | F | F | F | F | Bond | n-$C_4H_9$ |
| 2058 | $C_2H_5$ | F | F | F | F | Bond | n-$C_5H_{11}$ |
| 2059 | $C_2H_5$ | F | F | F | F | Bond | n-$C_6H_{13}$ |
| 2060 | $C_2H_5$ | F | F | F | F | Bond | n-$C_7H_{15}$ |
| 2061 | n-$C_3H_7$ | F | F | F | F | Bond | $CH_3$ |
| 2062 | n-$C_3H_7$ | F | F | F | F | Bond | $C_2H_5$ |
| 2063 | n-$C_3H_7$ | F | F | F | F | Bond | n-$C_3H_7$ |
| 2064 | n-$C_3H_7$ | F | F | F | F | Bond | n-$C_4H_9$ |
| 2065 | n-$C_3H_7$ | F | F | F | F | Bond | n-$C_5H_{11}$ |
| 2066 | n-$C_3H_7$ | F | F | F | F | Bond | n-$C_6H_{13}$ |
| 2067 | n-$C_3H_7$ | F | F | F | F | Bond | n-$C_7H_{15}$ |
| 2068 | n-$C_4H_9$ | F | F | F | F | Bond | $CH_3$ |
| 2069 | n-$C_4H_9$ | F | F | F | F | Bond | $C_2H_5$ |
| 2070 | n-$C_4H_9$ | F | F | F | F | Bond | n-$C_3H_7$ |
| 2071 | n-$C_4H_9$ | F | F | F | F | Bond | n-$C_4H_9$ |
| 2072 | n-$C_4H_9$ | F | F | F | F | Bond | n-$C_5H_{11}$ |
| 2073 | n-$C_4H_9$ | F | F | F | F | Bond | n-$C_6H_{13}$ |
| 2074 | n-$C_4H_9$ | F | F | F | F | Bond | n-$C_7H_{15}$ |
| 2075 | n-$C_5H_{11}$ | F | F | F | F | Bond | $CH_3$ |

-continued

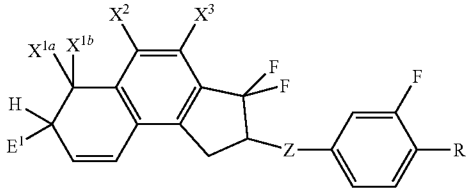

| Example | $E^1$ | $X^{1a}$ | $X^{1b}$ | $X^2$ | $X^3$ | Z | R |
|---|---|---|---|---|---|---|---|
| 2076 | n-$C_5H_{11}$ | F | F | F | F | Bond | $C_2H_5$ |
| 2077 | n-$C_5H_{11}$ | F | F | F | F | Bond | n-$C_3H_7$ |
| 2078 | n-$C_5H_{11}$ | F | F | F | F | Bond | n-$C_4H_9$ |
| 2079 | n-$C_5H_{11}$ | F | F | F | F | Bond | n-$C_5H_{11}$ |
| 2080 | n-$C_5H_{11}$ | F | F | F | F | Bond | n-$C_6H_{13}$ |
| 2081 | n-$C_5H_{11}$ | F | F | F | F | Bond | n-$C_7H_{15}$ |

Examples 2082-2130

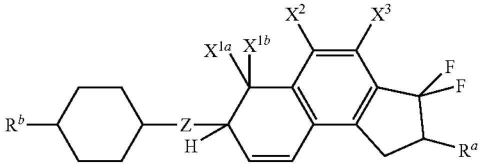

| Example | $R^b$ | $X^{1a}$ | $X^{1b}$ | $X^2$ | $X^3$ | Z | $R^a$ |
|---|---|---|---|---|---|---|---|
| 2082 | $CH_3$ | F | F | F | F | Bond | $CH_3$ |
| 2083 | $CH_3$ | F | F | F | F | Bond | $C_2H_5$ |
| 2084 | $CH_3$ | F | F | F | F | Bond | n-$C_3H_7$ |
| 2085 | $CH_3$ | F | F | F | F | Bond | n-$C_4H_9$ |
| 2086 | $CH_3$ | F | F | F | F | Bond | n-$C_5H_{11}$ |
| 2087 | $CH_3$ | F | F | F | F | Bond | n-$C_6H_{13}$ |
| 2088 | $CH_3$ | F | F | F | F | Bond | n-$C_7H_{15}$ |
| 2089 | $CH_3$ | F | F | F | F | $CF_2CF_2$ | $CH_3$ |
| 2090 | $CH_3$ | F | F | F | F | $CF_2CF_2$ | $C_2H_5$ |
| 2091 | $CH_3$ | F | F | F | F | $CF_2CF_2$ | n-$C_3H_7$ |
| 2092 | $CH_3$ | F | F | F | F | $CF_2CF_2$ | n-$C_4H_9$ |
| 2093 | $CH_3$ | F | F | F | F | $CF_2CF_2$ | n-$C_5H_{11}$ |
| 2094 | $CH_3$ | F | F | F | F | $CF_2CF_2$ | n-$C_6H_{13}$ |
| 2095 | $CH_3$ | F | F | F | F | $CF_2CF_2$ | n-$C_7H_{15}$ |
| 2096 | $C_2H_5$ | F | F | F | F | $CF_2CF_2$ | $CH_3$ |
| 2097 | $C_2H_5$ | F | F | F | F | $CF_2CF_2$ | $C_2H_5$ |
| 2098 | $C_2H_5$ | F | F | F | F | $CF_2CF_2$ | n-$C_3H_7$ |
| 2099 | $C_2H_5$ | F | F | F | F | $CF_2CF_2$ | n-$C_4H_9$ |
| 2100 | $C_2H_5$ | F | F | F | F | $CF_2CF_2$ | n-$C_5H_{11}$ |
| 2101 | $C_2H_5$ | F | F | F | F | $CF_2CF_2$ | n-$C_6H_{13}$ |
| 2102 | $C_2H_5$ | F | F | F | F | $CF_2CF_2$ | n-$C_7H_{15}$ |
| 2103 | $C_2H_5$ | F | F | F | F | Bond | $CH_3$ |
| 2104 | $C_2H_5$ | F | F | F | F | Bond | $C_2H_5$ |
| 2105 | $C_2H_5$ | F | F | F | F | Bond | n-$C_3H_7$ |
| 2106 | $C_2H_5$ | F | F | F | F | Bond | n-$C_4H_9$ |
| 2107 | $C_2H_5$ | F | F | F | F | Bond | n-$C_5H_{11}$ |
| 2108 | $C_2H_5$ | F | F | F | F | Bond | n-$C_6H_{13}$ |
| 2109 | $C_2H_5$ | F | F | F | F | Bond | n-$C_7H_{15}$ |
| 2110 | n-$C_3H_7$ | F | F | F | F | Bond | $CH_3$ |
| 2111 | n-$C_3H_7$ | F | F | F | F | Bond | $C_2H_5$ |
| 2112 | n-$C_3H_7$ | F | F | F | F | Bond | n-$C_3H_7$ |
| 2113 | n-$C_3H_7$ | F | F | F | F | Bond | n-$C_4H_9$ |
| 2114 | n-$C_3H_7$ | F | F | F | F | Bond | n-$C_5H_{11}$ |
| 2115 | n-$C_3H_7$ | F | F | F | F | Bond | n-$C_6H_{13}$ |
| 2116 | n-$C_3H_7$ | F | F | F | F | Bond | n-$C_7H_{15}$ |
| 2117 | n-$C_4H_9$ | F | F | F | F | Bond | $CH_3$ |
| 2118 | n-$C_4H_9$ | F | F | F | F | Bond | $C_2H_5$ |
| 2119 | n-$C_4H_9$ | F | F | F | F | Bond | n-$C_3H_7$ |
| 2120 | n-$C_4H_9$ | F | F | F | F | Bond | n-$C_4H_9$ |
| 2121 | n-$C_4H_9$ | F | F | F | F | Bond | n-$C_5H_{11}$ |
| 2122 | n-$C_4H_9$ | F | F | F | F | Bond | n-$C_6H_{13}$ |

-continued

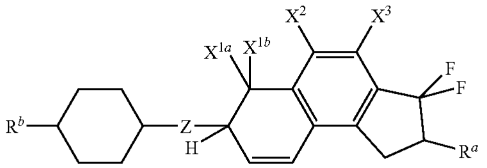

| Example | $R^b$ | $X^{1a}$ | $X^{1b}$ | $X^2$ | $X^3$ | Z | $R^a$ |
|---|---|---|---|---|---|---|---|
| 2123 | n-$C_4H_9$ | F | F | F | F | Bond | n-$C_7H_{15}$ |
| 2124 | n-$C_5H_{11}$ | F | F | F | F | Bond | $CH_3$ |
| 2125 | n-$C_5H_{11}$ | F | F | F | F | Bond | $C_2H_5$ |
| 2126 | n-$C_5H_{11}$ | F | F | F | F | Bond | n-$C_3H_7$ |
| 2127 | n-$C_5H_{11}$ | F | F | F | F | Bond | n-$C_4H_9$ |
| 2128 | n-$C_5H_{11}$ | F | F | F | F | Bond | n-$C_5H_{11}$ |
| 2129 | n-$C_5H_{11}$ | F | F | F | F | Bond | n-$C_6H_{13}$ |
| 2130 | n-$C_5H_{11}$ | F | F | F | F | Bond | n-$C_7H_{15}$ |

Examples 2131-2193

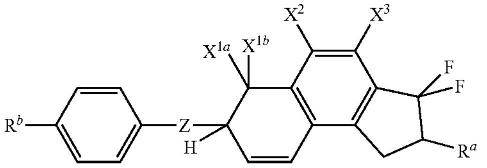

| Example | $R^b$ | $X^{1a}$ | $X^{1b}$ | $X^2$ | $X^3$ | Z | $R^a$ |
|---|---|---|---|---|---|---|---|
| 2131 | $CH_3$ | F | F | F | F | Bond | $CH_3$ |
| 2132 | $CH_3$ | F | F | F | F | Bond | $C_2H_5$ |
| 2133 | $CH_3$ | F | F | F | F | Bond | n-$C_3H_7$ |
| 2134 | $CH_3$ | F | F | F | F | Bond | n-$C_4H_9$ |
| 2135 | $CH_3$ | F | F | F | F | Bond | n-$C_5H_{11}$ |
| 2136 | $CH_3$ | F | F | F | F | Bond | n-$C_6H_{13}$ |
| 2137 | $CH_3$ | F | F | F | F | Bond | n-$C_7H_{15}$ |
| 2138 | $CH_3$ | F | F | F | F | $CF_2CF_2$ | $CH_3$ |
| 2139 | $CH_3$ | F | F | F | F | $CF_2CF_2$ | $C_2H_5$ |
| 2140 | $CH_3$ | F | F | F | F | $CF_2CF_2$ | n-$C_3H_7$ |
| 2141 | $CH_3$ | F | F | F | F | $CF_2CF_2$ | n-$C_4H_9$ |
| 2142 | $CH_3$ | F | F | F | F | $CF_2CF_2$ | n-$C_5H_{11}$ |
| 2143 | $CH_3$ | F | F | F | F | $CF_2CF_2$ | n-$C_6H_{13}$ |
| 2144 | $CH_3$ | F | F | F | F | $CF_2CF_2$ | n-$C_7H_{15}$ |
| 2145 | $CH_3$ | F | F | F | F | $OCF_2$ | $CH_3$ |
| 2146 | $CH_3$ | F | F | F | F | $OCF_2$ | $C_2H_5$ |
| 2147 | $CH_3$ | F | F | F | F | $OCF_2$ | n-$C_3H_7$ |
| 2148 | $CH_3$ | F | F | F | F | $OCF_2$ | n-$C_4H_9$ |
| 2149 | $CH_3$ | F | F | F | F | $OCF_2$ | n-$C_5H_{11}$ |
| 2150 | $CH_3$ | F | F | F | F | $OCF_2$ | n-$C_6H_{13}$ |
| 2151 | $CH_3$ | F | F | F | F | $OCF_2$ | n-$C_7H_{15}$ |
| 2152 | $C_2H_5$ | F | F | F | F | $CF_2CF_2$ | $CH_3$ |
| 2153 | $C_2H_5$ | F | F | F | F | $CF_2CF_2$ | $C_2H_5$ |
| 2154 | $C_2H_5$ | F | F | F | F | $CF_2CF_2$ | n-$C_3H_7$ |
| 2155 | $C_2H_5$ | F | F | F | F | $CF_2CF_2$ | n-$C_4H_9$ |
| 2156 | $C_2H_5$ | F | F | F | F | $CF_2CF_2$ | n-$C_5H_{11}$ |
| 2157 | $C_2H_5$ | F | F | F | F | $CF_2CF_2$ | n-$C_6H_{13}$ |
| 2158 | $C_2H_5$ | F | F | F | F | $CF_2CF_2$ | n-$C_7H_{15}$ |
| 2159 | $C_2H_5$ | F | F | F | F | $OCF_2$ | $CH_3$ |
| 2160 | $C_2H_5$ | F | F | F | F | $OCF_2$ | $C_2H_5$ |
| 2161 | $C_2H_5$ | F | F | F | F | $OCF_2$ | n-$C_3H_7$ |
| 2162 | $C_2H_5$ | F | F | F | F | $OCF_2$ | n-$C_4H_9$ |
| 2163 | $C_2H_5$ | F | F | F | F | $OCF_2$ | n-$C_5H_{11}$ |
| 2164 | $C_2H_5$ | F | F | F | F | $OCF_2$ | n-$C_6H_{13}$ |
| 2165 | $C_2H_5$ | F | F | F | F | $OCF_2$ | n-$C_7H_{15}$ |
| 2166 | $C_2H_5$ | F | F | F | F | Bond | $CH_3$ |
| 2167 | $C_2H_5$ | F | F | F | F | Bond | $C_2H_5$ |
| 2168 | $C_2H_5$ | F | F | F | F | Bond | n-$C_3H_7$ |
| 2169 | $C_2H_5$ | F | F | F | F | Bond | n-$C_4H_9$ |
| 2170 | $C_2H_5$ | F | F | F | F | Bond | n-$C_5H_{11}$ |

-continued

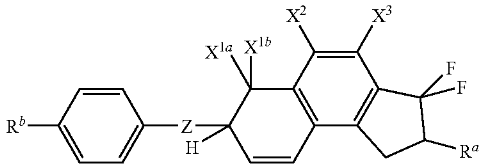

| Example | $R^b$ | $X^{1a}$ | $X^{1b}$ | $X^2$ | $X^3$ | Z | $R^a$ |
|---|---|---|---|---|---|---|---|
| 2171 | $C_2H_5$ | F | F | F | F | Bond | n-$C_6H_{13}$ |
| 2172 | $C_2H_5$ | F | F | F | F | Bond | n-$C_7H_{15}$ |
| 2173 | n-$C_3H_7$ | F | F | F | F | Bond | $CH_3$ |
| 2174 | n-$C_3H_7$ | F | F | F | F | Bond | $C_2H_5$ |
| 2175 | n-$C_3H_7$ | F | F | F | F | Bond | n-$C_3H_7$ |
| 2176 | n-$C_3H_7$ | F | F | F | F | Bond | n-$C_4H_9$ |
| 2177 | n-$C_3H_7$ | F | F | F | F | Bond | n-$C_5H_{11}$ |
| 2178 | n-$C_3H_7$ | F | F | F | F | Bond | n-$C_6H_{13}$ |
| 2179 | n-$C_3H_7$ | F | F | F | F | Bond | n-$C_7H_{15}$ |
| 2180 | n-$C_4H_9$ | F | F | F | F | Bond | $CH_3$ |
| 2181 | n-$C_4H_9$ | F | F | F | F | Bond | $C_2H_5$ |
| 2182 | n-$C_4H_9$ | F | F | F | F | Bond | n-$C_3H_7$ |
| 2183 | n-$C_4H_9$ | F | F | F | F | Bond | n-$C_4H_9$ |
| 2184 | n-$C_4H_9$ | F | F | F | F | Bond | n-$C_5H_{11}$ |
| 2185 | n-$C_4H_9$ | F | F | F | F | Bond | n-$C_6H_{13}$ |
| 2186 | n-$C_4H_9$ | F | F | F | F | Bond | n-$C_7H_{15}$ |
| 2187 | n-$C_5H_{11}$ | F | F | F | F | Bond | $CH_3$ |
| 2188 | n-$C_5H_{11}$ | F | F | F | F | Bond | $C_2H_5$ |
| 2189 | n-$C_5H_{11}$ | F | F | F | F | Bond | n-$C_3H_7$ |
| 2190 | n-$C_5H_{11}$ | F | F | F | F | Bond | n-$C_4H_9$ |
| 2191 | n-$C_5H_{11}$ | F | F | F | F | Bond | n-$C_5H_{11}$ |
| 2192 | n-$C_5H_{11}$ | F | F | F | F | Bond | n-$C_6H_{13}$ |
| 2193 | n-$C_5H_{11}$ | F | F | F | F | Bond | n-$C_7H_{15}$ |

Examples 2194-2235

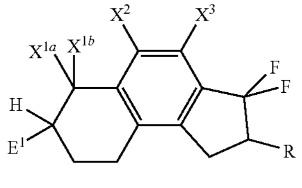

| Example | $E^1$ | $X^{1a}$ | $X^{1b}$ | $X^2$ | $X^3$ | R |
|---|---|---|---|---|---|---|
| 2194 | H | F | F | F | F | $CH_3$ |
| 2195 | H | F | F | F | F | $C_2H_5$ |
| 2196 | H | F | F | F | F | n-$C_3H_7$ |
| 2197 | H | F | F | F | F | n-$C_4H_9$ |
| 2198 | H | F | F | F | F | n-$C_5H_{11}$ |
| 2199 | H | F | F | F | F | n-$C_6H_{13}$ |
| 2200 | H | F | F | F | F | n-$C_7H_{15}$ |
| 2201 | $CH_3$ | F | F | F | F | $CH_3$ |
| 2202 | $CH_3$ | F | F | F | F | $C_2H_5$ |
| 2203 | $CH_3$ | F | F | F | F | n-$C_3H_7$ |
| 2204 | $CH_3$ | F | F | F | F | n-$C_4H_9$ |
| 2205 | $CH_3$ | F | F | F | F | n-$C_5H_{11}$ |
| 2206 | $CH_3$ | F | F | F | F | n-$C_6H_{13}$ |
| 2207 | $CH_3$ | F | F | F | F | n-$C_7H_{15}$ |
| 2208 | $C_2H_5$ | F | F | F | F | $CH_3$ |
| 2209 | $C_2H_5$ | F | F | F | F | $C_2H_5$ |
| 2210 | $C_2H_5$ | F | F | F | F | n-$C_3H_7$ |
| 2211 | $C_2H_5$ | F | F | F | F | n-$C_4H_9$ |
| 2212 | $C_2H_5$ | F | F | F | F | n-$C_5H_{11}$ |
| 2213 | $C_2H_5$ | F | F | F | F | n-$C_6H_{13}$ |
| 2214 | $C_2H_5$ | F | F | F | F | n-$C_7H_{15}$ |
| 2215 | n-$C_3H_7$ | F | F | F | F | $CH_3$ |
| 2216 | n-$C_3H_7$ | F | F | F | F | $C_2H_5$ |
| 2217 | n-$C_3H_7$ | F | F | F | F | n-$C_3H_7$ |
| 2218 | n-$C_3H_7$ | F | F | F | F | n-$C_4H_9$ |

-continued

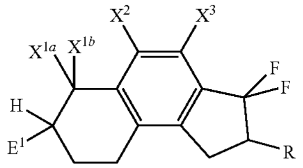

| Example | $E^1$ | $X^{1a}$ | $X^{1b}$ | $X^2$ | $X^3$ | R |
|---|---|---|---|---|---|---|
| 2219 | n-$C_3H_7$ | F | F | F | F | n-$C_5H_{11}$ |
| 2220 | n-$C_3H_7$ | F | F | F | F | n-$C_6H_{13}$ |
| 2221 | n-$C_3H_7$ | F | F | F | F | n-$C_7H_{15}$ |
| 2222 | n-$C_4H_9$ | F | F | F | F | $CH_3$ |
| 2223 | n-$C_4H_9$ | F | F | F | F | $C_2H_5$ |
| 2224 | n-$C_4H_9$ | F | F | F | F | n-$C_3H_7$ |
| 2225 | n-$C_4H_9$ | F | F | F | F | n-$C_4H_9$ |
| 2226 | n-$C_4H_9$ | F | F | F | F | n-$C_5H_{11}$ |
| 2227 | n-$C_4H_9$ | F | F | F | F | n-$C_6H_{13}$ |
| 2228 | n-$C_4H_9$ | F | F | F | F | n-$C_7H_{15}$ |
| 2229 | n-$C_5H_{11}$ | F | F | F | F | $CH_3$ |
| 2230 | n-$C_5H_{11}$ | F | F | F | F | $C_2H_5$ |
| 2231 | n-$C_5H_{11}$ | F | F | F | F | n-$C_3H_7$ |
| 2232 | n-$C_5H_{11}$ | F | F | F | F | n-$C_4H_9$ |
| 2233 | n-$C_5H_{11}$ | F | F | F | F | n-$C_5H_{11}$ |
| 2234 | n-$C_5H_{11}$ | F | F | F | F | n-$C_6H_{13}$ |
| 2235 | n-$C_5H_{11}$ | F | F | F | F | n-$C_7H_{15}$ |

Examples 2236-2305

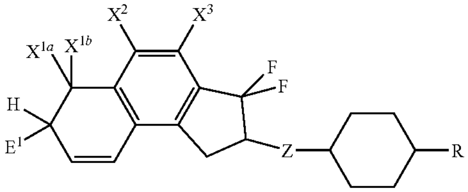

| Example | $E^1$ | $X^{1a}$ | $X^{1b}$ | $X^2$ | $X^3$ | Z | R |
|---|---|---|---|---|---|---|---|
| 2236 | H | F | F | F | F | Bond | $CH_3$ |
| 2237 | H | F | F | F | F | Bond | $C_2H_5$ |
| 2238 | H | F | F | F | F | Bond | n-$C_3H_7$ |
| 2239 | H | F | F | F | F | Bond | n-$C_4H_9$ |
| 2240 | H | F | F | F | F | Bond | n-$C_5H_{11}$ |
| 2241 | H | F | F | F | F | Bond | n-$C_6H_{13}$ |
| 2242 | H | F | F | F | F | Bond | n-$C_7H_{15}$ |
| 2243 | H | F | F | F | F | $CF_2CF_2$ | $CH_3$ |
| 2244 | H | F | F | F | F | $CF_2CF_2$ | $C_2H_5$ |
| 2245 | H | F | F | F | F | $CF_2CF_2$ | n-$C_3H_7$ |
| 2246 | H | F | F | F | F | $CF_2CF_2$ | n-$C_4H_9$ |
| 2247 | H | F | F | F | F | $CF_2CF_2$ | n-$C_5H_{11}$ |
| 2248 | H | F | F | F | F | $CF_2CF_2$ | n-$C_6H_{13}$ |
| 2249 | H | F | F | F | F | $CF_2CF_2$ | n-$C_7H_{15}$ |
| 2250 | H | F | F | F | F | $OCF_2$ | $CH_3$ |
| 2251 | H | F | F | F | F | $OCF_2$ | $C_2H_5$ |
| 2252 | H | F | F | F | F | $OCF_2$ | n-$C_3H_7$ |
| 2253 | H | F | F | F | F | $OCF_2$ | n-$C_4H_9$ |
| 2254 | H | F | F | F | F | $OCF_2$ | n-$C_5H_{11}$ |
| 2255 | H | F | F | F | F | $OCF_2$ | n-$C_6H_{13}$ |
| 2256 | H | F | F | F | F | $OCF_2$ | n-$C_7H_{15}$ |
| 2257 | $CH_3$ | F | F | F | F | Bond | $CH_3$ |
| 2258 | $CH_3$ | F | F | F | F | Bond | $C_2H_5$ |
| 2259 | $CH_3$ | F | F | F | F | Bond | n-$C_3H_7$ |
| 2260 | $CH_3$ | F | F | F | F | Bond | n-$C_4H_9$ |
| 2261 | $CH_3$ | F | F | F | F | Bond | n-$C_5H_{11}$ |
| 2262 | $CH_3$ | F | F | F | F | Bond | n-$C_6H_{13}$ |
| 2263 | $CH_3$ | F | F | F | F | Bond | n-$C_7H_{15}$ |
| 2264 | $CH_3$ | F | F | F | F | $CF_2CF_2$ | $CH_3$ |
| 2265 | $CH_3$ | F | F | F | F | $CF_2CF_2$ | $C_2H_5$ |

-continued

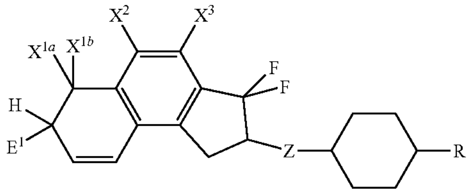

| Example | $E^1$ | $X^{1a}$ | $X^{1b}$ | $X^2$ | $X^3$ | Z | R |
|---|---|---|---|---|---|---|---|
| 2266 | $CH_3$ | F | F | F | F | $CF_2CF_2$ | n-$C_3H_7$ |
| 2267 | $CH_3$ | F | F | F | F | $CF_2CF_2$ | n-$C_4H_9$ |
| 2268 | $CH_3$ | F | F | F | F | $CF_2CF_2$ | n-$C_5H_{11}$ |
| 2269 | $CH_3$ | F | F | F | F | $CF_2CF_2$ | n-$C_6H_{13}$ |
| 2270 | $CH_3$ | F | F | F | F | $CF_2CF_2$ | n-$C_7H_{15}$ |
| 2271 | $CH_3$ | F | F | F | F | $OCF_2$ | $CH_3$ |
| 2272 | $CH_3$ | F | F | F | F | $OCF_2$ | $C_2H_5$ |
| 2273 | $CH_3$ | F | F | F | F | $OCF_2$ | n-$C_3H_7$ |
| 2274 | $CH_3$ | F | F | F | F | $OCF_2$ | n-$C_4H_9$ |
| 2275 | $CH_3$ | F | F | F | F | $OCF_2$ | n-$C_5H_{11}$ |
| 2276 | $CH_3$ | F | F | F | F | $OCF_2$ | n-$C_6H_{13}$ |
| 2277 | $CH_3$ | F | F | F | F | $OCF_2$ | n-$C_7H_{15}$ |
| 2278 | $C_2H_5$ | F | F | F | F | Bond | $CH_3$ |
| 2279 | $C_2H_5$ | F | F | F | F | Bond | $C_2H_5$ |
| 2280 | $C_2H_5$ | F | F | F | F | Bond | n-$C_3H_7$ |
| 2281 | $C_2H_5$ | F | F | F | F | Bond | n-$C_4H_9$ |
| 2282 | $C_2H_5$ | F | F | F | F | Bond | n-$C_5H_{11}$ |
| 2283 | $C_2H_5$ | F | F | F | F | Bond | n-$C_6H_{13}$ |
| 2284 | $C_2H_5$ | F | F | F | F | Bond | n-$C_7H_{15}$ |
| 2285 | n-$C_3H_7$ | F | F | F | F | Bond | $CH_3$ |
| 2286 | n-$C_3H_7$ | F | F | F | F | Bond | $C_2H_5$ |
| 2287 | n-$C_3H_7$ | F | F | F | F | Bond | n-$C_3H_7$ |
| 2288 | n-$C_3H_7$ | F | F | F | F | Bond | n-$C_4H_9$ |
| 2289 | n-$C_3H_7$ | F | F | F | F | Bond | n-$C_5H_{11}$ |
| 2290 | n-$C_3H_7$ | F | F | F | F | Bond | n-$C_6H_{13}$ |
| 2291 | n-$C_3H_7$ | F | F | F | F | Bond | n-$C_7H_{15}$ |
| 2292 | n-$C_4H_9$ | F | F | F | F | Bond | $CH_3$ |
| 2293 | n-$C_4H_9$ | F | F | F | F | Bond | $C_2H_5$ |
| 2294 | n-$C_4H_9$ | F | F | F | F | Bond | n-$C_3H_7$ |
| 2295 | n-$C_4H_9$ | F | F | F | F | Bond | n-$C_4H_9$ |
| 2296 | n-$C_4H_9$ | F | F | F | F | Bond | n-$C_5H_{11}$ |
| 2297 | n-$C_4H_9$ | F | F | F | F | Bond | n-$C_6H_{13}$ |
| 2298 | n-$C_4H_9$ | F | F | F | F | Bond | n-$C_7H_{15}$ |
| 2299 | n-$C_5H_{11}$ | F | F | F | F | Bond | $CH_3$ |
| 2300 | n-$C_5H_{11}$ | F | F | F | F | Bond | $C_2H_5$ |
| 2301 | n-$C_5H_{11}$ | F | F | F | F | Bond | n-$C_3H_7$ |
| 2302 | n-$C_5H_{11}$ | F | F | F | F | Bond | n-$C_4H_9$ |
| 2303 | n-$C_5H_{11}$ | F | F | F | F | Bond | n-$C_5H_{11}$ |
| 2304 | n-$C_5H_{11}$ | F | F | F | F | Bond | n-$C_6H_{13}$ |
| 2305 | n-$C_5H_{11}$ | F | F | F | F | Bond | n-$C_7H_{15}$ |

Examples 2306-2375

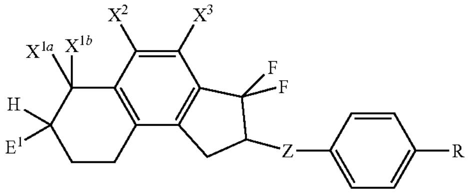

| Example | $E^1$ | $X^{1a}$ | $X^{1b}$ | $X^2$ | $X^3$ | Z | R |
|---|---|---|---|---|---|---|---|
| 2306 | H | F | F | F | F | Bond | $CH_3$ |
| 2307 | H | F | F | F | F | Bond | $C_2H_5$ |
| 2308 | H | F | F | F | F | Bond | n-$C_3H_7$ |
| 2309 | H | F | F | F | F | Bond | n-$C_4H_9$ |
| 2310 | H | F | F | F | F | Bond | n-$C_5H_{11}$ |
| 2311 | H | F | F | F | F | Bond | n-$C_6H_{13}$ |

-continued

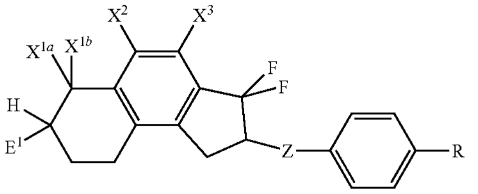

| Example | $E^1$ | $X^{1a}$ | $X^{1b}$ | $X^2$ | $X^3$ | Z | R |
|---|---|---|---|---|---|---|---|
| 2312 | H | F | F | F | F | Bond | $n-C_7H_{15}$ |
| 2313 | H | F | F | F | F | $CF_2CF_2$ | $CH_3$ |
| 2314 | H | F | F | F | F | $CF_2CF_2$ | $C_2H_5$ |
| 2315 | H | F | F | F | F | $CF_2CF_2$ | $n-C_3H_7$ |
| 2316 | H | F | F | F | F | $CF_2CF_2$ | $n-C_4H_9$ |
| 2317 | H | F | F | F | F | $CF_2CF_2$ | $n-C_5H_{11}$ |
| 2318 | H | F | F | F | F | $CF_2CF_2$ | $n-C_6H_{13}$ |
| 2319 | H | F | F | F | F | $CF_2CF_2$ | $n-C_7H_{15}$ |
| 2320 | H | F | F | F | F | $CF_2O$ | $CH_3$ |
| 2321 | H | F | F | F | F | $CF_2O$ | $C_2H_5$ |
| 2322 | H | F | F | F | F | $CF_2O$ | $n-C_3H_7$ |
| 2323 | H | F | F | F | F | $CF_2O$ | $n-C_4H_9$ |
| 2324 | H | F | F | F | F | $CF_2O$ | $n-C_5H_{11}$ |
| 2325 | H | F | F | F | F | $CF_2O$ | $n-C_6H_{13}$ |
| 2326 | H | F | F | F | F | $CF_2O$ | $n-C_7H_{15}$ |
| 2327 | $CH_3$ | F | F | F | F | Bond | $CH_3$ |
| 2328 | $CH_3$ | F | F | F | F | Bond | $C_2H_5$ |
| 2329 | $CH_3$ | F | F | F | F | Bond | $n-C_3H_7$ |
| 2330 | $CH_3$ | F | F | F | F | Bond | $n-C_4H_9$ |
| 2331 | $CH_3$ | F | F | F | F | Bond | $n-C_5H_{11}$ |
| 2332 | $CH_3$ | F | F | F | F | Bond | $n-C_6H_{13}$ |
| 2333 | $CH_3$ | F | F | F | F | Bond | $n-C_7H_{15}$ |
| 2334 | $CH_3$ | F | F | F | F | $CF_2CF_2$ | $CH_3$ |
| 2335 | $CH_3$ | F | F | F | F | $CF_2CF_2$ | $C_2H_5$ |
| 2336 | $CH_3$ | F | F | F | F | $CF_2CF_2$ | $n-C_3H_7$ |
| 2337 | $CH_3$ | F | F | F | F | $CF_2CF_2$ | $n-C_4H_9$ |
| 2338 | $CH_3$ | F | F | F | F | $CF_2CF_2$ | $n-C_5H_{11}$ |
| 2339 | $CH_3$ | F | F | F | F | $CF_2CF_2$ | $n-C_6H_{13}$ |
| 2340 | $CH_3$ | F | F | F | F | $CF_2CF_2$ | $n-C_7H_{15}$ |
| 2341 | $CH_3$ | F | F | F | F | $CF_2O$ | $CH_3$ |
| 2342 | $CH_3$ | F | F | F | F | $CF_2O$ | $C_2H_5$ |
| 2343 | $CH_3$ | F | F | F | F | $CF_2O$ | $n-C_3H_7$ |
| 2344 | $CH_3$ | F | F | F | F | $CF_2O$ | $n-C_4H_9$ |
| 2345 | $CH_3$ | F | F | F | F | $CF_2O$ | $n-C_5H_{11}$ |
| 2346 | $CH_3$ | F | F | F | F | $CF_2O$ | $n-C_6H_{13}$ |
| 2347 | $CH_3$ | F | F | F | F | $CF_2O$ | $n-C_7H_{15}$ |
| 2348 | $C_2H_5$ | F | F | F | F | Bond | $CH_3$ |
| 2349 | $C_2H_5$ | F | F | F | F | Bond | $C_2H_5$ |
| 2350 | $C_2H_5$ | F | F | F | F | Bond | $n-C_3H_7$ |
| 2351 | $C_2H_5$ | F | F | F | F | Bond | $n-C_4H_9$ |
| 2352 | $C_2H_5$ | F | F | F | F | Bond | $n-C_5H_{11}$ |
| 2353 | $C_2H_5$ | F | F | F | F | Bond | $n-C_6H_{13}$ |
| 2354 | $C_2H_5$ | F | F | F | F | Bond | $n-C_7H_{15}$ |
| 2355 | $n-C_3H_7$ | F | F | F | F | Bond | $CH_3$ |
| 2356 | $n-C_3H_7$ | F | F | F | F | Bond | $C_2H_5$ |
| 2357 | $n-C_3H_7$ | F | F | F | F | Bond | $n-C_3H_7$ |
| 2358 | $n-C_3H_7$ | F | F | F | F | Bond | $n-C_4H_9$ |
| 2359 | $n-C_3H_7$ | F | F | F | F | Bond | $n-C_5H_{11}$ |
| 2360 | $n-C_3H_7$ | F | F | F | F | Bond | $n-C_6H_{13}$ |
| 2361 | $n-C_3H_7$ | F | F | F | F | Bond | $n-C_7H_{15}$ |
| 2362 | $n-C_4H_9$ | F | F | F | F | Bond | $CH_3$ |
| 2363 | $n-C_4H_9$ | F | F | F | F | Bond | $C_2H_5$ |
| 2364 | $n-C_4H_9$ | F | F | F | F | Bond | $n-C_3H_7$ |
| 2365 | $n-C_4H_9$ | F | F | F | F | Bond | $n-C_4H_9$ |
| 2366 | $n-C_4H_9$ | F | F | F | F | Bond | $n-C_5H_{11}$ |
| 2367 | $n-C_4H_9$ | F | F | F | F | Bond | $n-C_6H_{13}$ |
| 2368 | $n-C_4H_9$ | F | F | F | F | Bond | $n-C_7H_{15}$ |
| 2369 | $n-C_5H_{11}$ | F | F | F | F | Bond | $CH_3$ |
| 2370 | $n-C_5H_{11}$ | F | F | F | F | Bond | $C_2H_5$ |
| 2371 | $n-C_5H_{11}$ | F | F | F | F | Bond | $n-C_3H_7$ |
| 2372 | $n-C_5H_{11}$ | F | F | F | F | Bond | $n-C_4H_9$ |
| 2373 | $n-C_5H_{11}$ | F | F | F | F | Bond | $n-C_5H_{11}$ |
| 2374 | $n-C_5H_{11}$ | F | F | F | F | Bond | $n-C_6H_{13}$ |
| 2375 | $n-C_5H_{11}$ | F | F | F | F | Bond | $n-C_7H_{15}$ |

Examples 2376-2445

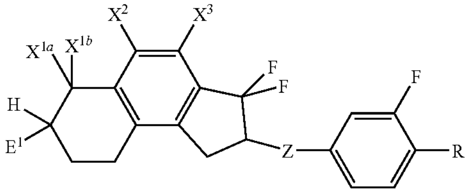

| Example | $E^1$ | $X^{1a}$ | $X^{1b}$ | $X^2$ | $X^3$ | Z | R |
|---|---|---|---|---|---|---|---|
| 2376 | H | F | F | F | F | Bond | $CH_3$ |
| 2377 | H | F | F | F | F | Bond | $C_2H_5$ |
| 2378 | H | F | F | F | F | Bond | $n-C_3H_7$ |
| 2379 | H | F | F | F | F | Bond | $n-C_4H_9$ |
| 2380 | H | F | F | F | F | Bond | $n-C_5H_{11}$ |
| 2381 | H | F | F | F | F | Bond | $n-C_6H_{13}$ |
| 2382 | H | F | F | F | F | Bond | $n-C_7H_{15}$ |
| 2383 | H | F | F | F | F | $CF_2CF_2$ | $CH_3$ |
| 2384 | H | F | F | F | F | $CF_2CF_2$ | $C_2H_5$ |
| 2385 | H | F | F | F | F | $CF_2CF_2$ | $n-C_3H_7$ |
| 2386 | H | F | F | F | F | $CF_2CF_2$ | $n-C_4H_9$ |
| 2387 | H | F | F | F | F | $CF_2CF_2$ | $n-C_5H_{11}$ |
| 2388 | H | F | F | F | F | $CF_2CF_2$ | $n-C_6H_{13}$ |
| 2389 | H | F | F | F | F | $CF_2CF_2$ | $n-C_7H_{15}$ |
| 2390 | H | F | F | F | F | $CF_2O$ | $CH_3$ |
| 2391 | H | F | F | F | F | $CF_2O$ | $C_2H_5$ |
| 2392 | H | F | F | F | F | $CF_2O$ | $n-C_3H_7$ |
| 2393 | H | F | F | F | F | $CF_2O$ | $n-C_4H_9$ |
| 2394 | H | F | F | F | F | $CF_2O$ | $n-C_5H_{11}$ |
| 2395 | H | F | F | F | F | $CF_2O$ | $n-C_6H_{13}$ |
| 2396 | H | F | F | F | F | $CF_2O$ | $n-C_7H_{15}$ |
| 2397 | $CH_3$ | F | F | F | F | Bond | $CH_3$ |
| 2398 | $CH_3$ | F | F | F | F | Bond | $C_2H_5$ |
| 2399 | $CH_3$ | F | F | F | F | Bond | $n-C_3H_7$ |
| 2400 | $CH_3$ | F | F | F | F | Bond | $n-C_4H_9$ |
| 2401 | $CH_3$ | F | F | F | F | Bond | $n-C_5H_{11}$ |
| 2402 | $CH_3$ | F | F | F | F | Bond | $n-C_6H_{13}$ |
| 2403 | $CH_3$ | F | F | F | F | Bond | $n-C_7H_{15}$ |
| 2404 | $CH_3$ | F | F | F | F | $CF_2CF_2$ | $CH_3$ |
| 2405 | $CH_3$ | F | F | F | F | $CF_2CF_2$ | $C_2H_5$ |
| 2406 | $CH_3$ | F | F | F | F | $CF_2CF_2$ | $n-C_3H_7$ |
| 2407 | $CH_3$ | F | F | F | F | $CF_2CF_2$ | $n-C_4H_9$ |
| 2408 | $CH_3$ | F | F | F | F | $CF_2CF_2$ | $n-C_5H_{11}$ |
| 2409 | $CH_3$ | F | F | F | F | $CF_2CF_2$ | $n-C_6H_{13}$ |
| 2410 | $CH_3$ | F | F | F | F | $CF_2CF_2$ | $n-C_7H_{15}$ |
| 2411 | $CH_3$ | F | F | F | F | $CF_2O$ | $CH_3$ |
| 2412 | $CH_3$ | F | F | F | F | $CF_2O$ | $C_2H_5$ |
| 2413 | $CH_3$ | F | F | F | F | $CF_2O$ | $n-C_3H_7$ |
| 2414 | $CH_3$ | F | F | F | F | $CF_2O$ | $n-C_4H_9$ |
| 2415 | $CH_3$ | F | F | F | F | $CF_2O$ | $n-C_5H_{11}$ |
| 2416 | $CH_3$ | F | F | F | F | $CF_2O$ | $n-C_6H_{13}$ |
| 2417 | $CH_3$ | F | F | F | F | $CF_2O$ | $n-C_7H_{15}$ |
| 2418 | $C_2H_5$ | F | F | F | F | Bond | $CH_3$ |
| 2419 | $C_2H_5$ | F | F | F | F | Bond | $C_2H_5$ |
| 2420 | $C_2H_5$ | F | F | F | F | Bond | $n-C_3H_7$ |
| 2421 | $C_2H_5$ | F | F | F | F | Bond | $n-C_4H_9$ |
| 2422 | $C_2H_5$ | F | F | F | F | Bond | $n-C_5H_{11}$ |
| 2423 | $C_2H_5$ | F | F | F | F | Bond | $n-C_6H_{13}$ |
| 2424 | $C_2H_5$ | F | F | F | F | Bond | $n-C_7H_{15}$ |
| 2425 | $n-C_3H_7$ | F | F | F | F | Bond | $CH_3$ |
| 2426 | $n-C_3H_7$ | F | F | F | F | Bond | $C_2H_5$ |
| 2427 | $n-C_3H_7$ | F | F | F | F | Bond | $n-C_3H_7$ |
| 2428 | $n-C_3H_7$ | F | F | F | F | Bond | $n-C_4H_9$ |
| 2429 | $n-C_3H_7$ | F | F | F | F | Bond | $n-C_5H_{11}$ |
| 2430 | $n-C_3H_7$ | F | F | F | F | Bond | $n-C_6H_{13}$ |
| 2431 | $n-C_3H_7$ | F | F | F | F | Bond | $n-C_7H_{15}$ |
| 2432 | $n-C_4H_9$ | F | F | F | F | Bond | $CH_3$ |
| 2433 | $n-C_4H_9$ | F | F | F | F | Bond | $C_2H_5$ |
| 2434 | $n-C_4H_9$ | F | F | F | F | Bond | $n-C_3H_7$ |
| 2435 | $n-C_4H_9$ | F | F | F | F | Bond | $n-C_4H_9$ |
| 2436 | $n-C_4H_9$ | F | F | F | F | Bond | $n-C_5H_{11}$ |
| 2437 | $n-C_4H_9$ | F | F | F | F | Bond | $n-C_6H_{13}$ |
| 2438 | $n-C_4H_9$ | F | F | F | F | Bond | $n-C_7H_{15}$ |
| 2439 | $n-C_5H_{11}$ | F | F | F | F | Bond | $CH_3$ |

-continued

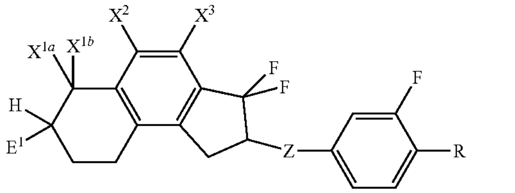

| Example | $E^1$ | $X^{1a}$ | $X^{1b}$ | $X^2$ | $X^3$ | Z | R |
|---|---|---|---|---|---|---|---|
| 2440 | $n-C_5H_{11}$ | F | F | F | F | Bond | $C_2H_5$ |
| 2441 | $n-C_5H_{11}$ | F | F | F | F | Bond | $n-C_3H_7$ |
| 2442 | $n-C_5H_{11}$ | F | F | F | F | Bond | $n-C_4H_9$ |
| 2443 | $n-C_5H_{11}$ | F | F | F | F | Bond | $n-C_5H_{11}$ |
| 2444 | $n-C_5H_{11}$ | F | F | F | F | Bond | $n-C_6H_{13}$ |
| 2445 | $n-C_5H_{11}$ | F | F | F | F | Bond | $n-C_7H_{15}$ |

Examples 2446-2494

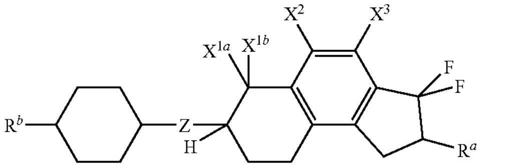

| Example | $R^b$ | $X^{1a}$ | $X^{1b}$ | $X^2$ | $X^3$ | Z | $R^a$ |
|---|---|---|---|---|---|---|---|
| 2446 | $CH_3$ | F | F | F | F | Bond | $CH_3$ |
| 2447 | $CH_3$ | F | F | F | F | Bond | $C_2H_5$ |
| 2448 | $CH_3$ | F | F | F | F | Bond | $n-C_3H_7$ |
| 2449 | $CH_3$ | F | F | F | F | Bond | $n-C_4H_9$ |
| 2450 | $CH_3$ | F | F | F | F | Bond | $n-C_5H_{11}$ |
| 2451 | $CH_3$ | F | F | F | F | Bond | $n-C_6H_{13}$ |
| 2452 | $CH_3$ | F | F | F | F | Bond | $n-C_7H_{15}$ |
| 2453 | $CH_3$ | F | F | F | F | $CF_2CF_2$ | $CH_3$ |
| 2454 | $CH_3$ | F | F | F | F | $CF_2CF_2$ | $C_2H_5$ |
| 2455 | $CH_3$ | F | F | F | F | $CF_2CF_2$ | $n-C_3H_7$ |
| 2456 | $CH_3$ | F | F | F | F | $CF_2CF_2$ | $n-C_4H_9$ |
| 2457 | $CH_3$ | F | F | F | F | $CF_2CF_2$ | $n-C_5H_{11}$ |
| 2458 | $CH_3$ | F | F | F | F | $CF_2CF_2$ | $n-C_6H_{13}$ |
| 2459 | $CH_3$ | F | F | F | F | $CF_2CF_2$ | $n-C_7H_{15}$ |
| 2460 | $C_2H_5$ | F | F | F | F | $CF_2CF_2$ | $CH_3$ |
| 2461 | $C_2H_5$ | F | F | F | F | $CF_2CF_2$ | $C_2H_5$ |
| 2462 | $C_2H_5$ | F | F | F | F | $CF_2CF_2$ | $n-C_3H_7$ |
| 2463 | $C_2H_5$ | F | F | F | F | $CF_2CF_2$ | $n-C_4H_9$ |
| 2464 | $C_2H_5$ | F | F | F | F | $CF_2CF_2$ | $n-C_5H_{11}$ |
| 2465 | $C_2H_5$ | F | F | F | F | $CF_2CF_2$ | $n-C_6H_{13}$ |
| 2466 | $C_2H_5$ | F | F | F | F | $CF_2CF_2$ | $n-C_7H_{15}$ |
| 2467 | $C_2H_5$ | F | F | F | F | Bond | $CH_3$ |
| 2468 | $C_2H_5$ | F | F | F | F | Bond | $C_2H_5$ |
| 2469 | $C_2H_5$ | F | F | F | F | Bond | $n-C_3H_7$ |
| 2470 | $C_2H_5$ | F | F | F | F | Bond | $n-C_4H_9$ |
| 2471 | $C_2H_5$ | F | F | F | F | Bond | $n-C_5H_{11}$ |
| 2472 | $C_2H_5$ | F | F | F | F | Bond | $n-C_6H_{13}$ |
| 2473 | $C_2H_5$ | F | F | F | F | Bond | $n-C_7H_{15}$ |
| 2474 | $n-C_3H_7$ | F | F | F | F | Bond | $CH_3$ |
| 2475 | $n-C_3H_7$ | F | F | F | F | Bond | $C_2H_5$ |
| 2476 | $n-C_3H_7$ | F | F | F | F | Bond | $n-C_3H_7$ |
| 2477 | $n-C_3H_7$ | F | F | F | F | Bond | $n-C_4H_9$ |
| 2478 | $n-C_3H_7$ | F | F | F | F | Bond | $n-C_5H_{11}$ |
| 2479 | $n-C_3H_7$ | F | F | F | F | Bond | $n-C_6H_{13}$ |
| 2480 | $n-C_3H_7$ | F | F | F | F | Bond | $n-C_7H_{15}$ |
| 2481 | $n-C_4H_9$ | F | F | F | F | Bond | $CH_3$ |
| 2482 | $n-C_4H_9$ | F | F | F | F | Bond | $C_2H_5$ |
| 2483 | $n-C_4H_9$ | F | F | F | F | Bond | $n-C_3H_7$ |
| 2484 | $n-C_4H_9$ | F | F | F | F | Bond | $n-C_4H_9$ |
| 2485 | $n-C_4H_9$ | F | F | F | F | Bond | $n-C_5H_{11}$ |
| 2486 | $n-C_4H_9$ | F | F | F | F | Bond | $n-C_6H_{13}$ |

-continued

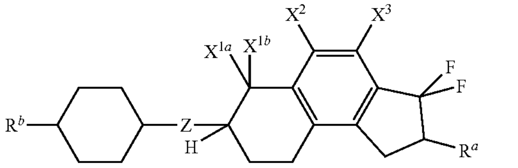

| Example | $R^b$ | $X^{1a}$ | $X^{1b}$ | $X^2$ | $X^3$ | Z | $R^a$ |
|---|---|---|---|---|---|---|---|
| 2487 | $n-C_4H_9$ | F | F | F | F | Bond | $n-C_7H_{15}$ |
| 2488 | $n-C_5H_{11}$ | F | F | F | F | Bond | $CH_3$ |
| 2489 | $n-C_5H_{11}$ | F | F | F | F | Bond | $C_2H_5$ |
| 2490 | $n-C_5H_{11}$ | F | F | F | F | Bond | $n-C_3H_7$ |
| 2491 | $n-C_5H_{11}$ | F | F | F | F | Bond | $n-C_4H_9$ |
| 2492 | $n-C_5H_{11}$ | F | F | F | F | Bond | $n-C_5H_{11}$ |
| 2493 | $n-C_5H_{11}$ | F | F | F | F | Bond | $n-C_6H_{13}$ |
| 2494 | $n-C_5H_{11}$ | F | F | F | F | Bond | $n-C_7H_{15}$ |

Examples 2495-2557

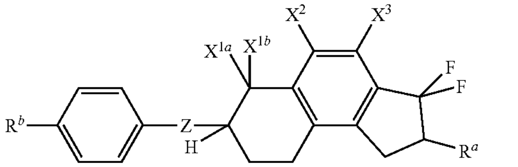

| Example | $R^b$ | $X^{1a}$ | $X^{1b}$ | $X^2$ | $X^3$ | Z | $R^a$ |
|---|---|---|---|---|---|---|---|
| 2495 | $CH_3$ | F | F | F | F | Bond | $CH_3$ |
| 2496 | $CH_3$ | F | F | F | F | Bond | $C_2H_5$ |
| 2497 | $CH_3$ | F | F | F | F | Bond | $n-C_3H_7$ |
| 2498 | $CH_3$ | F | F | F | F | Bond | $n-C_4H_9$ |
| 2499 | $CH_3$ | F | F | F | F | Bond | $n-C_5H_{11}$ |
| 2500 | $CH_3$ | F | F | F | F | Bond | $n-C_6H_{13}$ |
| 2501 | $CH_3$ | F | F | F | F | Bond | $n-C_7H_{15}$ |
| 2502 | $CH_3$ | F | F | F | F | $CF_2CF_2$ | $CH_3$ |
| 2503 | $CH_3$ | F | F | F | F | $CF_2CF_2$ | $C_2H_5$ |
| 2504 | $CH_3$ | F | F | F | F | $CF_2CF_2$ | $n-C_3H_7$ |
| 2505 | $CH_3$ | F | F | F | F | $CF_2CF_2$ | $n-C_4H_9$ |
| 2506 | $CH_3$ | F | F | F | F | $CF_2CF_2$ | $n-C_5H_{11}$ |
| 2507 | $CH_3$ | F | F | F | F | $CF_2CF_2$ | $n-C_6H_{13}$ |
| 2508 | $CH_3$ | F | F | F | F | $CF_2CF_2$ | $n-C_7H_{15}$ |
| 2509 | $CH_3$ | F | F | F | F | $OCF_2$ | $CH_3$ |
| 2510 | $CH_3$ | F | F | F | F | $OCF_2$ | $C_2H_5$ |
| 2511 | $CH_3$ | F | F | F | F | $OCF_2$ | $n-C_3H_7$ |
| 2512 | $CH_3$ | F | F | F | F | $OCF_2$ | $n-C_4H_9$ |
| 2513 | $CH_3$ | F | F | F | F | $OCF_2$ | $n-C_5H_{11}$ |
| 2514 | $CH_3$ | F | F | F | F | $OCF_2$ | $n-C_6H_{13}$ |
| 2515 | $CH_3$ | F | F | F | F | $OCF_2$ | $n-C_7H_{15}$ |
| 2516 | $C_2H_5$ | F | F | F | F | $CF_2CF_2$ | $CH_3$ |
| 2517 | $C_2H_5$ | F | F | F | F | $CF_2CF_2$ | $C_2H_5$ |
| 2518 | $C_2H_5$ | F | F | F | F | $CF_2CF_2$ | $n-C_3H_7$ |
| 2519 | $C_2H_5$ | F | F | F | F | $CF_2CF_2$ | $n-C_4H_9$ |
| 2520 | $C_2H_5$ | F | F | F | F | $CF_2CF_2$ | $n-C_5H_{11}$ |
| 2521 | $C_2H_5$ | F | F | F | F | $CF_2CF_2$ | $n-C_6H_{13}$ |
| 2522 | $C_2H_5$ | F | F | F | F | $CF_2CF_2$ | $n-C_7H_{15}$ |
| 2523 | $C_2H_5$ | F | F | F | F | $OCF_2$ | $CH_3$ |
| 2524 | $C_2H_5$ | F | F | F | F | $OCF_2$ | $C_2H_5$ |
| 2525 | $C_2H_5$ | F | F | F | F | $OCF_2$ | $n-C_3H_7$ |
| 2526 | $C_2H_5$ | F | F | F | F | $OCF_2$ | $n-C_4H_9$ |
| 2527 | $C_2H_5$ | F | F | F | F | $OCF_2$ | $n-C_5H_{11}$ |
| 2528 | $C_2H_5$ | F | F | F | F | $OCF_2$ | $n-C_6H_{13}$ |
| 2529 | $C_2H_5$ | F | F | F | F | $OCF_2$ | $n-C_7H_{15}$ |
| 2530 | $C_2H_5$ | F | F | F | F | Bond | $CH_3$ |
| 2531 | $C_2H_5$ | F | F | F | F | Bond | $C_2H_5$ |
| 2532 | $C_2H_5$ | F | F | F | F | Bond | $n-C_3H_7$ |
| 2533 | $C_2H_5$ | F | F | F | F | Bond | $n-C_4H_9$ |
| 2534 | $C_2H_5$ | F | F | F | F | Bond | $n-C_5H_{11}$ |

-continued

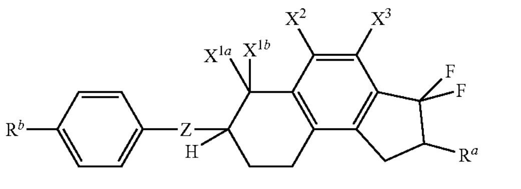

| Example | $R^b$ | $X^{1a}$ | $X^{1b}$ | $X^2$ | $X^3$ | Z | $R^a$ |
|---|---|---|---|---|---|---|---|
| 2535 | $C_2H_5$ | F | F | F | F | Bond | n-$C_6H_{13}$ |
| 2536 | $C_2H_5$ | F | F | F | F | Bond | n-$C_7H_{15}$ |
| 2537 | n-$C_3H_7$ | F | F | F | F | Bond | $CH_3$ |
| 2538 | n-$C_3H_7$ | F | F | F | F | Bond | $C_2H_5$ |
| 2539 | n-$C_3H_7$ | F | F | F | F | Bond | n-$C_3H_7$ |
| 2540 | n-$C_3H_7$ | F | F | F | F | Bond | n-$C_4H_9$ |
| 2541 | n-$C_3H_7$ | F | F | F | F | Bond | n-$C_5H_{11}$ |
| 2542 | n-$C_3H_7$ | F | F | F | F | Bond | n-$C_6H_{13}$ |
| 2543 | n-$C_3H_7$ | F | F | F | F | Bond | n-$C_7H_{15}$ |
| 2544 | n-$C_4H_9$ | F | F | F | F | Bond | $CH_3$ |
| 2545 | n-$C_4H_9$ | F | F | F | F | Bond | $C_2H_5$ |
| 2546 | n-$C_4H_9$ | F | F | F | F | Bond | n-$C_3H_7$ |
| 2547 | n-$C_4H_9$ | F | F | F | F | Bond | n-$C_4H_9$ |
| 2548 | n-$C_4H_9$ | F | F | F | F | Bond | n-$C_5H_{11}$ |
| 2549 | n-$C_4H_9$ | F | F | F | F | Bond | n-$C_6H_{13}$ |
| 2550 | n-$C_4H_9$ | F | F | F | F | Bond | n-$C_7H_{15}$ |
| 2551 | n-$C_5H_{11}$ | F | F | F | F | Bond | $CH_3$ |
| 2552 | n-$C_5H_{11}$ | F | F | F | F | Bond | $C_2H_5$ |
| 2553 | n-$C_5H_{11}$ | F | F | F | F | Bond | n-$C_3H_7$ |
| 2554 | n-$C_5H_{11}$ | F | F | F | F | Bond | n-$C_4H_9$ |
| 2555 | n-$C_5H_{11}$ | F | F | F | F | Bond | n-$C_5H_{11}$ |
| 2556 | n-$C_5H_{11}$ | F | F | F | F | Bond | n-$C_6H_{13}$ |
| 2557 | n-$C_5H_{11}$ | F | F | F | F | Bond | n-$C_7H_{15}$ |

TABLE 1

Δε- and Δn values for substances of individual examples

| Example No. | Δε | Δn |
|---|---|---|
| 10 (Comp. 33) | −7.4 | 0.186 |
| 80 | −9.0 | 0.116 |
| 126 | −8.4 | 0.100 |
| 154 | −9.7 | 0.107 |
| 504 | −8.5 | 0.124 |
| 2198 | −10.7 | 0.067 |
| 2238 | −6.0 | 0.070 |

The invention claimed is:

1. A cyclopenta[a]naphthalene compound of formula I, II, Ill, IV or V

I

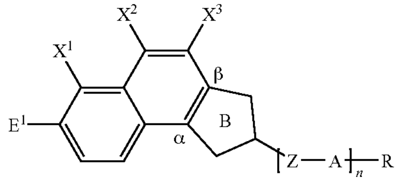

II

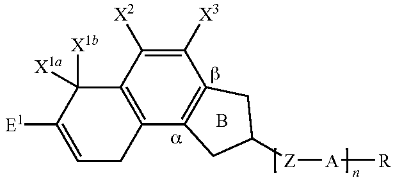

-continued

III

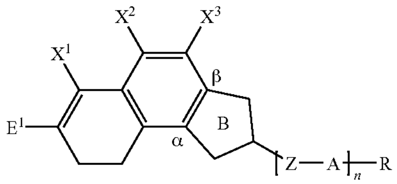

IV

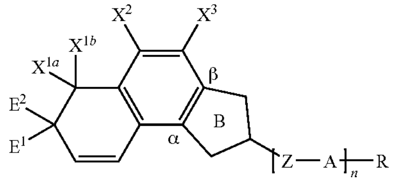

V

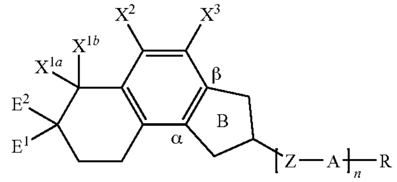

in which:

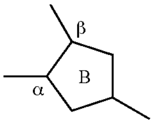

is a

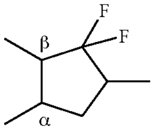

, b

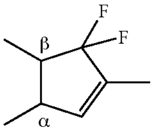

, c

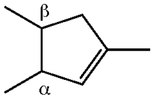

, d

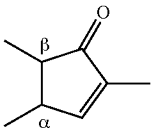

, f

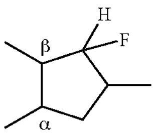

, g

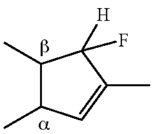

,

-continued h

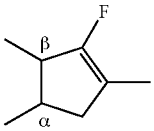

, or i

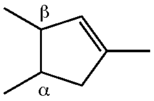

;

A is in each case, independently of one another, 1,4-phenylene, in which =CH— may be replaced once or twice by =N—, and which may be monosubstituted to tetrasubstituted, independently of one another, by halogen (—F, —Cl, —Br, —I), —CN, —$CH_3$, —$CH_2F$, —$CHF_2$, —$CF_3$, —$OCH_3$, —$OCH_2F$, —$OCHF_2$ or —$OCF_3$, 1,4-cyclohexylene, 1,4-cyclohexenylene or 1,4-cyclohexadienylene, in which —$CH_2$— may in each case be replaced once or twice, independently of one another, by —O— or —S— in such a way that heteroatoms are not linked directly, and which all may be monosubstituted or polysubstituted by halogen;

Z is in each case, independently of one another, a single bond, a double bond, —$CF_2O$—, —$OCF_2$—, —$CH_2CH_2$—, —$CF_2CF_2$—, —$CF_2$—$CH_2$—, —$CH_2$—$CF_2$—, —CHF—CHF—, —C(O)O—, —OC(O)—, —$CH_2O$—, —$OCH_2$—, —CF=CH—, —CH=CF—, —CF=CF—, —CH=CH—or —C≡C—;

R is hydrogen, an alkyl, alkoxy, alkenyl or alkynyl radical having from 1 to 15 or 2 to 15 carbon atoms respectively which is unsubstituted, monosubstituted by —CN or —$CF_3$ or at least monosubstituted by halogen, where, in addition, one or more $CH_2$ groups in these radicals may each, independently of one another, be replaced by —O—, —S—, —CO—, —COO—, —OCO—or —OCO—O— in such a way that heteroatoms are not linked directly, halogen, —CN, —SCN, —NCS, —$SF_5$, —$CF_3$, —$OCF_3$, —$OCHF_2$ or —$OCH_2F$;

$X^1$, $X^{1a}$, $X^{1b}$, $X^2$ and $X^3$ are each, independently of one another, hydrogen, an alkyl, alkoxy, alkenyl or alkynyl radical having from 1 to 15 or 2 to 15 carbon atoms respectively which is unsubstituted or at least monosubstituted by halogen, where, in addition, one or more $CH_2$ groups in these radicals may each, independently of one another, be replaced by —O—, —S—, —CO—, —COO—, —OCO—or —OCO—O—in such a way that heteroatoms are not linked directly, halogen, —CN, —$SF_5$, —SCN, —NCS, —$CF_3$, —$OCF_3$, —$OCHF_2$ or —$OCH_2F$;

$E^1$ and $E^2$ are each, independently of one another, hydrogen, an alkyl, alkoxy, alkenyl or alkynyl radical having from 1 to 15 or 2 to 15 carbon atoms respectively which is unsubstituted, monosubstituted by —CN or —$CF_3$ or at least monosubstituted by halogen, where, in addition, one or more $CH_2$ groups in these radicals may each, independently of one another, be replaced by —O—, —S—, —CO—, —COO—, —OCO—or —OCO—O— in such a way that heteroatoms are not linked directly, halogen, —CN, —SCN, —NCS, —$SF_5$, —$CF_3$, —$OCF_3$, —$OCHF_2$, —$OCH_2F$ or —(—Z—A—)$_n$—R; and n is 1, 2 or 3;

where in the formula I, ring B does not stand for the formula c if $X^1$, $X^2$ and $X^3$ are simultaneously hydrogen.

2. A cyclopenta[a]naphthalene compound according to claim 1, wherein

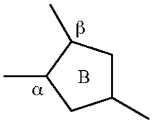

is a

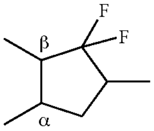

, b

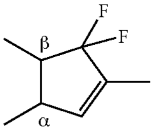

, f

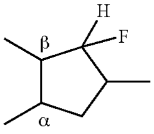

, g

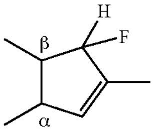

, or h

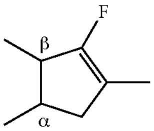

.

3. A cyclopenta[a]naphthalene compound according to claim 1, wherein

Z is a single bond, —$CF_2O$—, —$OCF_2$—, —$CF_2CF_2$—, —CH=CH—, —CF=CH—, —CH=CF—or —CF=CF—.

4. A cyclopenta[a]naphthalene compound according to claim 1, wherein

A is

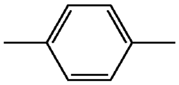

,

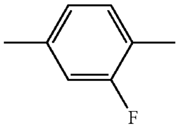

,

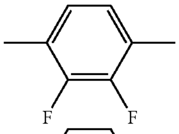

,

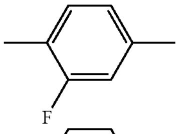

,

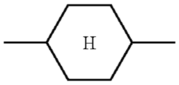

,

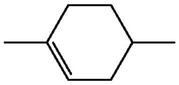

,

-continued

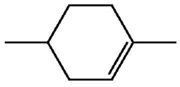, 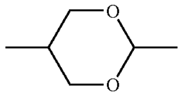, 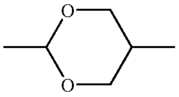, 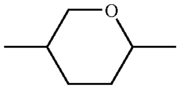 or 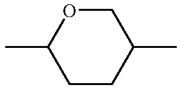.

5. A cyclopenta[a]naphthalene compound according to claim 1, wherein

R is an alkyl radical, alkoxy radical or alkenyl radical having from 1 to 7 or 2 to 7 carbon atoms respectively.

6. A cyclopenta[a]naphthalene compound according to claim 1, wherein $E^1$ and $E^2$, independently of one another, are hydrogen, an alkyl radical or alkoxy radical having from 1 to 7 carbon atoms, fluorine, chlorine or —(-Z-A-)$_n$—R, in which n is 1, Z is a single bond, A is 1,4-cyclohexylene or optionally mono- or poly-fluorine-substituted 1,4-phenylene, and R is alkyl, alkoxy or alkenyl having from 1 to 7 or 2 to 7 carbon atoms respectively.

7. A cyclopenta[a]naphthalene compound according to claim 1, wherein at least one of $X^1$, $X^2$ and $X^3$ or at least one of $X^{1a}$, $X^{1b}$, $X^3$ and $X^3$ is —$CF_3$, fluorine or chlorine.

8. A cyclopenta[a]naphthalene compound according to claim 1, wherein $X^1$, $X^2$ and $X^3$ or $X^{1a}$, $X^{1b}$, $X^2$ and $X^3$ are —$CF_3$, fluorine and/or chlorine.

9. A cyclopenta[a]naphthalene compound according to claim 1, wherein $X^1$, $X^2$ and $X^3$ or $X^{1a}$, $X^{1b}$, $X^2$ and $X^3$ are fluorine.

10. A liquid-crystalline medium comprising at least two liquid-crystalline compounds, wherein at least one liquid-crystalline compound is a cyclopenta[a]naphthalene compound according to claim 1.

11. An electro-optical display element containing a liquid-crystalline medium according to claim 10.

12. A cyclopenta[a]naphthalene compound of formula VI, VII, VIII, IX or X,

VI

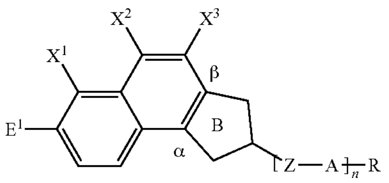

VII

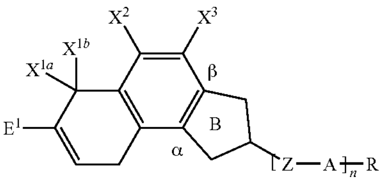

-continued

VIII

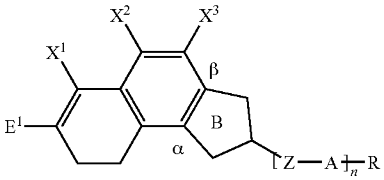

IX

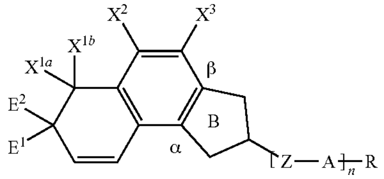

X

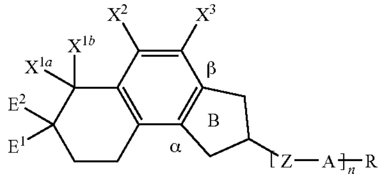

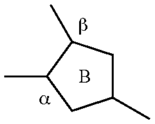 is 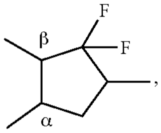, a 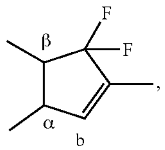, b

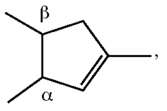, c 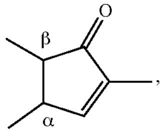, d 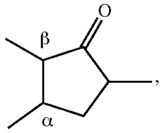, e

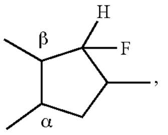, f 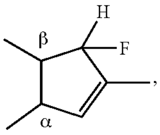, g 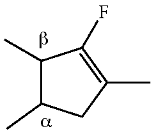 or h

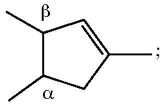; i

A is in each case, independently of one another, 1,4-phenylene, in which =CH— may be replaced once or twice by =N—, and which may be monosubstituted to tetrasubstituted, independently of one another, by halogen (—F, —Cl, —Br, —I), —CN, —$CH_3$, —$CH_2F$, —$CHF_2$, —$CF_3$, —$OCH_3$, —$OCH_2F$, —$OCHF_2$ or —$OCF_3$, 1,4-cyclohexylene, 1,4-cyclohexenylene or 1,4-cyclohexadienylene, in which —$CH_2$— may in each case be replaced once or twice, independently of one another, by —O— or —S— in such a way that heteroatoms are not linked directly, and which all may be monosubstituted or polysubstituted by halogen;

Z is in each case, independently of one another, a single bond, a double bond, $-CF_2O-$, $-OCF_2-$, $-CH_2CH_2-$, $-CF_2CF_2-$, $-CF_2-CH_2-$, $-CH_2-CF_2-$, $-CHF-CHF-$, $-C(O)O-$, $-OC(O)-$, $-CH_2O-$, $-OCH_2-$, $-CF{=}CH-$, $-CH{=}CF-$, $-CF{=}CF-$, $-CH{=}CH-$ or $C{\equiv}C-$;

R is an alkyl, alkoxy, alkenyl or alkynyl radical having from 1 to 15 or 2 to 15 carbon atoms respectively which is unsubstituted, monosubstituted by $-CN$ or $-CF_3$ or at least monosubstituted by halogen, where, in addition, one or more $CH_2$ groups in these radicals may each, independently of one another, be replaced by $-O-$, $-S-$, $-CO-$, $-COO-$, $-OCO-$ or $-OCO-O-$ in such a way that heteroatoms are not linked directly, halogen, $-CN$, $-SCN$, $-NCS$, $-SF_5$, $-CF_3$, $-OCF_3$, $-OCHF_2$ or $-OCH_2F$;

$X^1$, $X^{1a}$, $X^{1b}$, $X^2$ and $X^3$ are each, independently of one another, hydrogen, an alkyl, alkoxy, alkenyl or alkynyl radical having from 1 to 15 or 2 to 15 carbon atoms respectively which is unsubstituted or at least monosubstituted by halogen, where, in addition, one or more $CH_2$ groups in these radicals may each, independently of one another, be replaced by $-O-$, $-S-$, $-CO-$, $-COO-$, $-OCO-$ or $-OCO-O-$ in such a way that heteroatoms are not linked directly, halogen, $-CN$, $-SF_5$, $-SCN$, $-NCS$, $-CF_3$, $-OCF_3$, $-OCHF_2$ or $-OCH_2F$;

$E^1$ and $E^2$ are each, independently of one another, hydrogen, an alkyl, alkoxy, alkenyl or alkynyl radical having from 1 to 15 or 2 to 15 carbon atoms respectively which is unsubstituted, monosubstituted by $-CN$ or $-CF_3$ or at least monosubstituted by halogen, where, in addition, one or more $CH_2$ groups in these radicals may each, independently of one another, be replaced by $-O-$, $-S-$, $-CO-$, $-COO-$, $-OCO-$ or $-OCO-O-$ in such a way that heteroatoms are not linked directly, halogen, $-CN$, $-SCN$, $-NCS$, $-SF_5$, $-CF_3$, $-OCF_3$, $-OCHF_2$, $-OCH_2F$ or $-(\text{-Z-A-})_n-R$; and n is 0, 1, 2 or 3;

where in formula VI, ring B does not stand for formula e if $X^2$ and $X^3$ are simultaneously fluorine or if $E^1$ is hydrogen and simultaneously $X^1$ and $X^2$ are fluorine and at least one of $X^1$, $X^2$ and $X^3$ or at least one of $X^{1a}$, $X^{1b}$ and $X^2$ and $X^3$ is $-CF_3$, fluorine and/or chlorine.

13. A cyclopenta[a]naphthalene compound according to claim 12, wherein

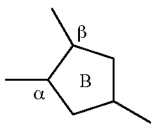

is a

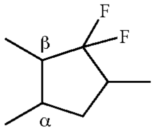

,

-continued b

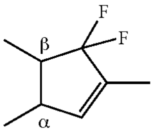

, f

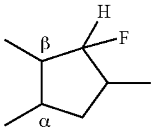

, g

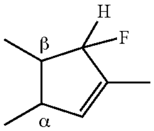

, or h

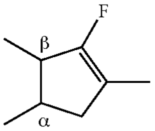

.

14. A cyclopenta[a]naphthalene compound according to claim 12, wherein

Z is a single bond, $-CF_2O-$, $-OCF_2-$, $-CF_2CF_2-$, $-CH{=}CH-$, $-CF{=}CH-$, $-CH{=}CF-$ or $-CF{=}CF-$.

15. A cyclopenta[a]naphthalene compound according to claim 12, wherein

A is

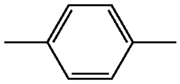, 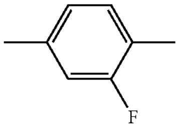, 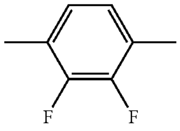, 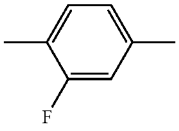, 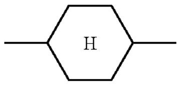, 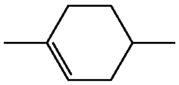, 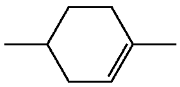, 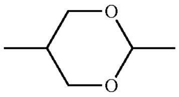, 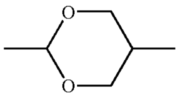, 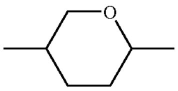 or 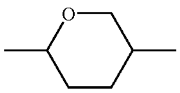.

16. A cyclopenta[a]naphthalene compound according to claim 12, wherein

R is an alkyl radical, alkoxy radical or alkenyl radical having from 1 to 7 or 2 to 7 carbon atoms respectively.

17. A cyclopenta[a]naphthalene compound according to claim 1, wherein $E^1$ and $E^2$, independently of one another, are hydrogen, an alkyl radical or alkoxy radical having from 1 to 7 carbon atoms, fluorine, chlorine or $-(-Z-A-)_n$—R, in which n is 1, Z is a single bond, A is 1,4-cyclohexylene or optionally mono- or poly-fluorine-substituted 1,4-phenylene, and R is alkyl, alkoxy or alkenyl having from 1 to 7 or 2 to 7 carbon atoms respectively.

18. A liquid-crystalline medium comprising at least two liquid-crystalline compounds, wherein at least one liquid-crystalline compound is a cyclopenta[a]naphthalene derivative according to claim 12.

19. An electro-optical display element containing a liquid-crystalline medium according to claim 18.

* * * * *

UNITED STATES PATENT AND TRADEMARK OFFICE

CERTIFICATE OF CORRECTION

PATENT NO. : 7,575,785 B2
APPLICATION NO. : 10/568783
DATED : August 18, 2009
INVENTOR(S) : Lietzau et al.

It is certified that error appears in the above-identified patent and that said Letters Patent is hereby corrected as shown below:

Column 83, line 31 reads "at least one of $X^1$, $X^2$ and $X^3$ or at least one of $X^{1a}$, $X^{1b}$, $X^3$", should read --at least one of $X^1$, $X^2$ and $X^3$ or at least one of $X^{1a}$, $X^{1b}$, $X^2$--.

Column 84, after line 28, insert --in which--.

Signed and Sealed this

Twenty-seventh Day of October, 2009

David J. Kappos

*Director of the United States Patent and Trademark Office*